United States Patent
Redmond

(10) Patent No.: US 9,717,248 B2
(45) Date of Patent: Aug. 1, 2017

(54) ANTIBACTERIAL MICRO- AND NANOPARTICLES COMPRISING A CHLORHEXIDINE SALT, METHOD OF PRODUCTION AND USES THEREOF

(71) Applicant: The University of Bristol, Bristol (GB)

(72) Inventor: Michele Emily Redmond, Gloucestershire (GB)

(73) Assignee: The University of Bristol, Bristol (GB)

( * ) Notice: Subject to any disclaimer, the term of this patent is extended or adjusted under 35 U.S.C. 154(b) by 0 days.

(21) Appl. No.: 14/891,951

(22) PCT Filed: May 16, 2014

(86) PCT No.: PCT/GB2014/051515
§ 371 (c)(1),
(2) Date: Nov. 17, 2015

(87) PCT Pub. No.: WO2014/184582
PCT Pub. Date: Nov. 20, 2014

(65) Prior Publication Data
US 2016/0128332 A1  May 12, 2016

(30) Foreign Application Priority Data

May 17, 2013  (GB) .................................. 1308926.3

(51) Int. Cl.
| | |
|---|---|
| *A01N 47/44* | (2006.01) |
| *A01N 25/12* | (2006.01) |
| *A01N 25/22* | (2006.01) |
| *A61K 8/43* | (2006.01) |
| *A61K 8/02* | (2006.01) |
| *A61L 15/20* | (2006.01) |
| *A61L 15/44* | (2006.01) |
| *A61L 29/08* | (2006.01) |
| *A61L 29/16* | (2006.01) |
| *A61Q 11/00* | (2006.01) |
| *A01N 25/34* | (2006.01) |
| *A61K 6/00* | (2006.01) |
| *C09D 5/14* | (2006.01) |
| *C09D 7/12* | (2006.01) |

(52) U.S. Cl.
CPC .............. *A01N 47/44* (2013.01); *A01N 25/12* (2013.01); *A01N 25/22* (2013.01); *A01N 25/34* (2013.01); *A61K 6/0008* (2013.01); *A61K 6/0067* (2013.01); *A61K 8/0245* (2013.01); *A61K 8/43* (2013.01); *A61L 15/20* (2013.01); *A61L 15/44* (2013.01); *A61L 29/08* (2013.01); *A61L 29/16* (2013.01); *A61Q 11/00* (2013.01); *C09D 5/14* (2013.01); *C09D 7/1233* (2013.01); *C09D 7/1275* (2013.01); *A61K 2800/413* (2013.01); *A61K 2800/74* (2013.01); *A61L 2300/206* (2013.01); *A61L 2300/404* (2013.01); *A61L 2300/602* (2013.01); *A61L 2300/606* (2013.01); *A61L 2420/00* (2013.01)

(58) Field of Classification Search
CPC ............... A61K 9/14; A61K 9/51; A61K 9/70
See application file for complete search history.

(56) References Cited

U.S. PATENT DOCUMENTS

| | | | |
|---|---|---|---|
| 4,980,150 A | 12/1990 | Keith | |
| 2007/0212419 A1 | 9/2007 | Bako et al. | |
| 2008/0085949 A1 | 4/2008 | McGhee | |
| 2011/0293690 A1* | 12/2011 | Griffin | ................. A61K 9/1641 424/443 |

FOREIGN PATENT DOCUMENTS

| | | |
|---|---|---|
| BR | PI 0802906 | 6/2011 |
| EP | 2462960 A2 | 6/2012 |
| FR | 2792532 | 10/2000 |
| WO | 2011009083 | 1/2011 |
| WO | 2012/119155 | 9/2012 |

OTHER PUBLICATIONS

Barbour et al., Synthesis, characterisation, and efficacy of antimicrobial chlorhexidine hexametaphosphate nanoparticles for applications in biomedical materials and consumer products; International Journal of Nanomedicine, Sep. 1, 2013, 3507.
Hatch et al., Surface-active properties of hexametaphosphate; Industrial and Engineering Chemistry, vol. 31, No. 1, 51-58, Jan. 1939.
Thomson; Some properties of sodium hexametaphosphate; The Analyst, vol. 61, No. 722, 320, Nov. 1935.
Piani et al., Sodium tripolyphosphate and polyphosphate as dispersing agents for alumina suspensions: rheological characterization; Journal of Engineering, vol. 101, No. 41, 8264, 2013.

* cited by examiner

*Primary Examiner* — Walter Webb
(74) *Attorney, Agent, or Firm* — Stites & Harbison PLLC; Richard S. Myers, Jr.

(57) ABSTRACT

Antimicrobial micro- or nanoparticles comprising a chlorhexidine salt and an anion, and a method of making the antimicrobial micro- or nanoparticle, are disclosed. The anion in the salt is selected form oxoanions and partially hydrogenated oxoanions of phosphorus, carbon, nitrogen, and sulfur.

14 Claims, 28 Drawing Sheets

ANTIBACTERIAL MICRO- AND NANOPARTICLES COMPRISING A CHLORHEXIDINE SALT, METHOD OF PRODUCTION AND USES THEREOF

CROSS REFERENCE TO RELATED APPLICATIONS

This application is a §371 National State Application of PCT/GB2014/051515 filed May 16, 2014 which claims priority to GB 1308926.3 filed May 17, 2013.

TECHNICAL FIELD

The present invention relates to the field of antimicrobial micro- or nanoparticle (MNPs). More specifically, the present invention relates to an antimicrobial micro- or nanoparticle comprising a chlorhexidine salt and methods of making and using the same; medical articles and composite materials comprising such antimicrobial MNPs for controlling the delivery of chlorhexidine.

BACKGROUND

Chlorhexidine (CHX) is a well-known antimicrobial which finds use in various medical applications. These include skin cleansing preparations, hand disinfectants and mouthrinses. CHX is a useful antimicrobial due to its efficacy against both Gram-positive and Gram-negative bacteria and many species of yeast. A further advantage over other antimicrobials is the desirable antibiotic resistance properties associated with CHX. Although individual microbe populations can become less sensitive to CHX when subjected to increasing environmental concentrations, studies have shown that this resistance is temporary and falls when the CHX stimulus is removed.

The systematic name for CHX is N',N'''''-hexane-1,6-diylbis[N-(4-chlorophenyl)(imidodicarbonimidic diamide)] and it has the following chemical formula.

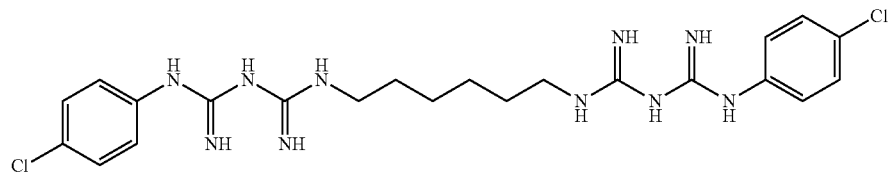 [SMILES: N=C(NCCCCCCNC(=N)NC(=N)Nc1ccc(Cl)cc1)NC(=N)Nc1ccc(Cl)cc1]

The most common CHX antimicrobial is an aqueous solution of the readily soluble salt CHX digluconate. The slightly less soluble salt CHX diacetate (CHA) has also been used, sometimes as a dry crystalline powder which is added to materials in order to confer some antimicrobial properties on those materials.

A problem with these CHX compounds is that when used in antimicrobial compositions they provide only very short-term delivery of aqueous CHX to the target areas. For example, in oral hygiene applications CHX digluconate may be delivered to the oral cavity in a mouthrinse, but within minutes the levels of CHX in this aqueous solution are severely depleted. A repeat of the treatment is necessary in order to maintain the delivery of sufficient levels of antimicrobial to the target area.

A further limitation is that the amount of CHX (e.g. the amount per unit surface area) that can be released from a treated substrate is limited and linked to the concentration of the CHX solution when surface treating with soluble CHX salts in solution, and therefore the antimicrobial efficacy of these solutions is also limited, not easily controllable, and may not be sufficient.

EP 2462960 A2 discloses a medical indwelling device such as a catheter having an antimicrobial agent. The device includes a base material which is a silicone-urethane copolymer and a bioactive agent such as CHX or a suitable pharmacological salt thereof, such as CHA. CHX is released from the base material at a rate dependent on the specific copolymer composition. Slow release of CHX is observed over a period of 14 days. However, the applications are limited to coatings on polymeric catheters because the base polymer is required to retain the CHX. Additionally, it would be desirable to provide extended release of CHX to an even greater extent.

US 2007/0212419 A1 discloses a nanocomposite biocompatible hydrogel (NCHG) containing a matrix gel, nanoparticles (NPs) and CHX for use in the treatment of periodontal infections. The NPs are polymeric, made from copolymerised 2-hydroxyethyl methacrylate (HEMA) and polyethyleneglycol dimethacrylate (PEGDMA). The same monomers are used to produce the crosslinked matrix. CHX digluconate is used as the active agent. The NPs absorb CHX and extended release over 200 hours is observed. Again, applications are limited by the presence of the matrix gel, and the release profile of the CHX is still unsatisfactory for some applications. The NCHG cannot be used to confer antimicrobial properties on existing medical articles or compositions.

The present invention addresses the problems discussed above by providing an antimicrobial micro- or nanoparticle (MNP) comprising a CHX salt. Some of the particular CHX salts proposed herein provide sparingly soluble MNPs which in some aspects display an excellent release profile for CHX over an extended period of months rather than simply days or weeks. In some embodiments the CHX MNPs described herein can release CHX gradually for longer than 80 days. Other CHX salts proposed herein have a shorter CHX release period but, over a few hours or days, release a very high dose of soluble CHX. In some aspects, the release of CHX from samples treated with MNPs of these CHX salts is faster and in larger amount than is achieved from samples treated only with a CHX solution. These faster-release aspects may be useful in decontamination applications or to treat particularly stubborn or acute infections or outbreaks. Furthermore, the MNPs can find use in a wide variety of applications such as coatings on or embedded within medical articles to confer additional antimicrobial properties, or as a component of a composite material which can be used to deliver steady doses of antimicrobial CHX to target areas over a long period of time by means of the gradual leaching of soluble CHX out of the antimicrobial MNPs, or to deliver higher doses of CHX much more quickly than is possible from samples treated with CHX solution. Additionally, the MNPs of the present invention may also exhibit delayed release profiles, or profiles where the release of CHX is triggered by changes in environmental conditions.

SUMMARY

In certain aspects, the present invention provides an antimicrobial micro- or nanoparticle comprising a CHX salt. In particular, the present invention provides antimicrobial micro- or nanoparticles comprising a CHX salt wherein the anion in the salt is selected from oxoanions and partially hydrogenated oxoanions of phosphorus, carbon, nitrogen, and sulphur. Preferably the anion is selected from oxoanions of phosphorus, carbon, nitrogen, and sulphur, and more preferably the anion is at least one selected from phosphates, carbonate, nitrate or sulphate. More preferably, the anion is selected from phosphates chosen from the homologous series of polyphosphates which begins with pyrophosphate and the homologous series of cyclic metaphosphates which begins with trimetaphosphate, and oxoanions and partially hydrogenated oxoanions of nitrogen and sulphur. More preferably, the anion is selected from phosphates chosen from the homologous series of polyphosphates which begins with pyrophosphate and the homologous series of cyclic metaphosphates which begins with trimetaphosphate. Most preferably, the anion is selected from the homologous series of cyclic metaphosphates which begins with trimetaphosphate, especially hexametaphosphate.

In preferred aspects the MNPs are nanosized, i.e. the structures have at least one dimension in the range 1 nm-1 $\mu$m.

The present invention also provides a colloidal suspension of antimicrobial MNPs as described herein.

These proposals also provide a medical article comprising antimicrobial MNPs as described herein and a composite material comprising antimicrobial MNPs as described herein.

The present invention also contemplates methods of making and using antimicrobial MNPs as described herein.

By 'antimicrobial' is meant a substance which acts to kill microorganisms or at least inhibits their growth. The term. 'microbe' is used to describe a microscopic organism such as bacteria, archaea and/or fungi for example. Therefore, antimicrobial compounds and compositions herein may kill these microscopic organisms or at least inhibit their growth.

The term 'phosphates' as used herein refers to any phosphorus and oxygen based anion. Phosphates are usually made up of tetrahedrally coordinated orthophosphorus residues. Phosphates may be linear, branched or cyclic. Exemplary phosphates include phosphates of the homologous series of linear phosphates and polyphosphates which begins with orthophosphate and pyrophosphate, and the homologous series of cyclic metaphosphates which begins with trimetaphosphate. Organophosphates are also included within this definition. Exemplary organophosphates include alkyl phosphates, such as $C_{1-6}$ alkyl phosphates.

By 'micro- or nanoparticle' is meant particles sized between around 1 nm and 100 $\mu$m.

In the present description, 'micro- or nanoparticle' is also intended to encompass other suitable micro- and nanostructures, such as tubes (both single- and multi-walled), scrolls, rods, cones, "hedgehog" forms, crystals (such as elongate crystals) and amorphous forms. Such structures exhibit at least one spatial dimension from around 1 nm to 100 $\mu$m, preferably from 1 nm to 10 $\mu$m, preferably from 1 nm to less than 1 $\mu$m (i.e. "nanostructures" or "nanoscale" dimensions), more preferably from 5 nm to 500 nm, more preferably from 20 to 200 nm, even more preferably from 20 to 140 nm. All three dimensions of the structure may fall within this size range.

BRIEF DESCRIPTION OF THE FIGURES

Note—Scale bar size and image magnification given in square brackets for each SEM.

DETAILED DESCRIPTION

Antimicrobial Nanoparticles

Figure 1:
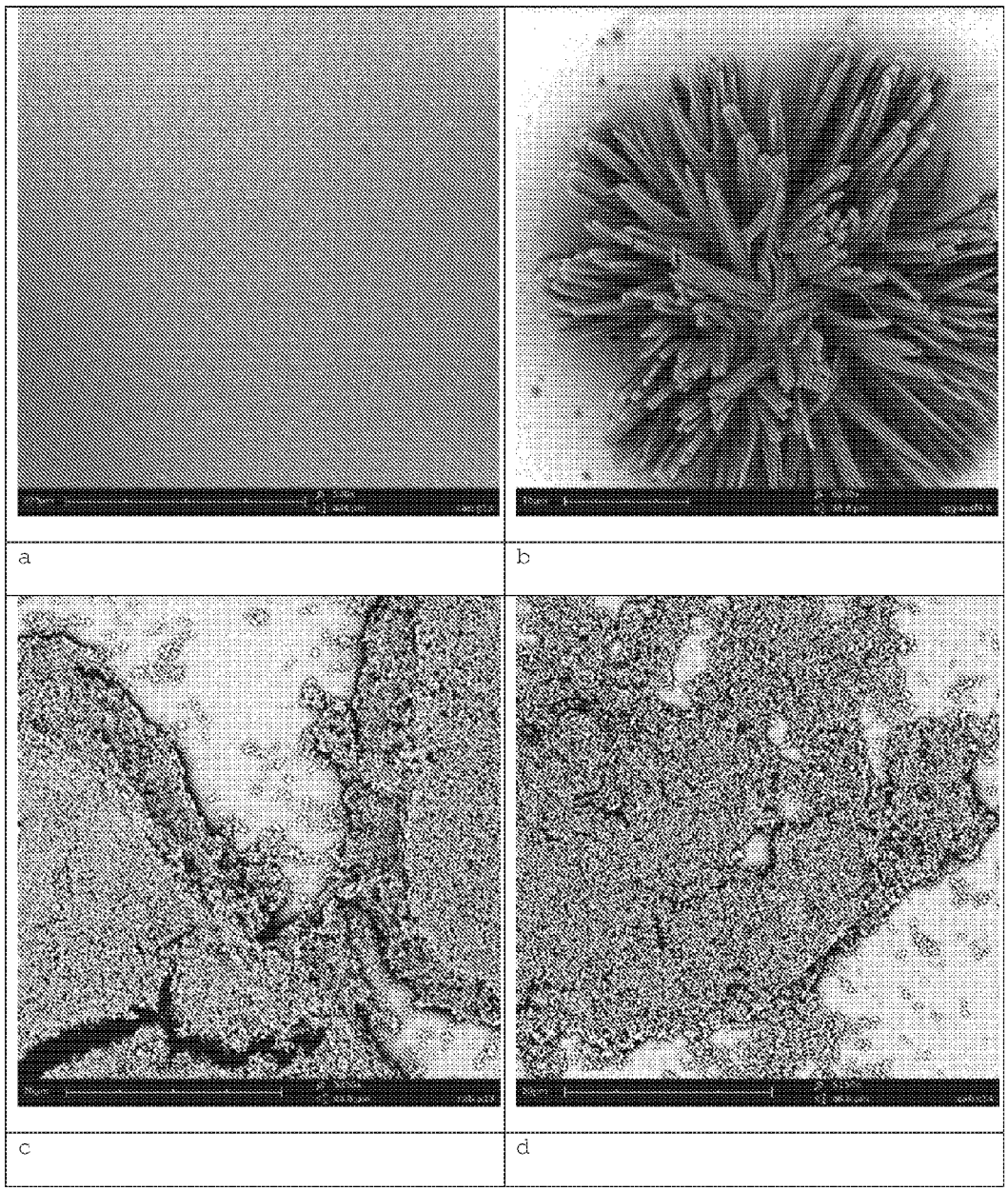
FIG. 1 shows SEM micrographs of borosilicate glass coverslips after immersion in the following compositions. (a) water or aqueous CHX (25 $\mu$M and 5 mM) [220 $\mu$m, 540×]; (b) 5/5 CHX-orthophosphate [10 $\mu$m, 6200×]; (c) 5/5 CHX-pyrophosphate [20 $\mu$m, 5350×]; (d) 5/5 CHX-triphosphate [20 $\mu$m, 5150×].

According to a first aspect of the invention, there is provided antimicrobial micro- or nanoparticles comprising a chlorhexidine salt, wherein the anion in the salt is selected from (oxoanions and partially hydrogenated oxoanions of phosphorus, carbon, nitrogen, and sulphur. Preferably the anion is selected from oxoanions of phosphorus, carbon, nitrogen, and sulphur, and more preferably the anion is at least one selected from phosphates, carbonate, nitrate or sulphate. When at least one anion selected from this list is used in a compound with CHX, MNPs can be formed which are sparingly soluble. This sparing solubility means that the MNPs of the present invention can demonstrate a tailored release profile. In some aspects the profile is an extended release profile, releasing a steady level of CHX into a surrounding liquid environment over an extended period. In other aspects the release of CHX is faster and/or in larger amounts as noted above, e.g. in some cases faster and in larger amount than is achievable from a surface treated with a solution of only CHX.

In the present invention 'phosphates' includes any phosphorus-based anion composed of tetrahedrally coordinated orthophosphorus residues linked by the sharing of oxygen atoms and derived from the deprotonation of a phosphoric acid.

The particular phosphate anions which may be used in the present invention are not particularly limited, and may include any anion which comprises phosphorus and oxygen atoms. Preferably, the phosphate anions are monophosphates or polyphosphates. Preferably, the phosphate anions have a linear, branched or cyclic structure. Preferably, the phosphate anions are derived, by removal of one or more hydrogen atoms, from a polyphosphoric acid having the general formula $HO(PO_2OH)_nH$ where n could be any integer but is typically from 1 up to several hundred, preferably 1-10, more preferably 1-6.

Even more preferably, the phosphate is selected from at least one of orthophosphate, pyrophosphate, triphosphate or hexametaphosphate. Metaphosphates, are particularly preferred, especially hexametaphosphate.

In some aspects, the antimicrobial MNP of the present invention comprises a sparingly soluble CHX salt. When the MNPs comprise such a salt which has low solubility, the release of CHX from the MNP into the surrounding liquid environment is prolonged. Additionally, when the salt is sparingly soluble in this way, the MNPs tend to form a colloidal suspension in water which is advantageous for deposition of the MNPs onto surfaces by dip-coating because it provides a more uniform distribution of the MNPs throughout the liquid and because the charge on the nanoparticles facilitates their adsorption to material surfaces.

In some aspects, the antimicrobial MNPs of the present invention demonstrate sustained release of soluble CHX in a liquid environment over a long time period. This may be at least 90 days. In other aspects, the antimicrobial MNPs of the present invention demonstrate release of CHX at higher levels than can be achieved by treatment of surfaces using a simple CHX solution. This may be over only a short period of time (such as periods up to 5 days, up to 1 day, up to 12 hours, up to 6 hours, up to 1 hour, up to 30 mins, up to 10 mins or up to 1 min), or may be sustained release over longer periods (such as periods up to 90 days, up to 60 days, up to 30 days, or up to 10 days).

Particularly preferably, the chlorhexidine salt is chlorhexidine hexametaphosphate (CHX-HMP). CHX-HMP is sparingly soluble and so forms a colloidal suspension of MNPs. These MNPs may then be used to coat an article, or may be incorporated into a composite material. The relative insolubility of CHX-HMP means that CHX is released slowly and steadily into the surrounding environment. CHX-HMP shows an extended release profile for the release of CHX.

Preferably, the antimicrobial MNP of the present invention shows extended and sustained release in a liquid environment (preferably an aqueous environment) of soluble CHX over a period of at least 7 days, preferably at least 20 days, more preferably at least 30 days, more preferably at least 50 days, more preferably at least 60 days, more preferably at least 100 days, and in some situations at least six months or at least twelve months. This extended and sustained release means that CHX is continuously released from the MNPs throughout the time period. Preferably the release rate is about constant throughout this time period although embodiments are envisaged in which the release rate alters, e.g. declines, with increasing time. This sustained release profile allows the antimicrobial properties of the MNPs to be exploited over a long period of time without the need for extra intervention.

Preferably, the antimicrobial MNP consists essentially of a CHX salt, wherein the anion in the salt is selected from at least one of phosphates, carbonate, nitrate or sulphate. By this is meant that a CHX salt is present in a particular MNP but that other components may also be present. Preferably, the CHX salt makes up at least 40 wt %, more preferably at least 60 wt %, more preferably at least 90 wt % of the antimicrobial MNP, and particularly preferably at least 99 wt %. In some situations the CHX salt may make up 100 wt % of the antimicrobial MNP. The other components in the MNPs may include one or more of polymers (such as polyethylene glycol), fillers, colourants, and agents (e.g. silanes or polylysine) which can facilitate bonding to surfaces or incorporation within composite materials. The higher levels of CHX salt in the MNPs provide enhanced (e.g. stronger and/or longer lasting) antimicrobial efficacy.

Combinations of the specified anions may also be used to produce the antimicrobial MNPs, for example by co-precipitation of the CHX cation with a mixture of different anions. For example anions which lead to MNPs which exhibit rapid, release of high levels of CHX may be combined with anions which lead to MNPs exhibiting CHX release at lower levels but over a more prolonged period. Such particles may be useful, e.g. in medical devices, especially those that are surgically implanted, where the initial high levels of CHX release would counter bacteria present due to the surgery itself and the longer, lower level release of CHX would maintain a clean site over an extended period. Preferably, the antimicrobial MNP comprises a salt of CHX and one anion selected from those listed above. For example the present proposals include a mixture of MNPs comprising CHX hexametaphosphate salt with MNPs comprising a CHX salt in which the anion is selected from orthophosphate, pyrophosphate, triphosphate, carbonate, and nitrate.

In some aspects, in addition to the CHX cation there may be present one or more additional cations in the antimicrobial MNP, for example one or more metal cations, e.g. Cu or Ag.

In some cases, the antimicrobial MNPs of the present invention are delayed release particles, i.e. the release of CHX is delayed for a period of time after applying the MNPs to the surface of a substrate or incorporating them into a composite. During this delay period, preferably no CHX is released from the MNPs or, in some cases, the release of CHX from the MNPs during this delay period is at a low rate, e.g. less than 10%, preferably less than 5%, more preferably less than 1% of the eventual release rate immediately following the delay period. In preferred cases, the MNPs are sensitive to changes in environmental conditions. In such cases, the MNPs may be said to show "smart" properties. Preferably, the release of CHX from the MNPs is triggered by a change in environmental conditions. For example a change in the pH, concentration of a certain trigger component, or temperature of the surrounding environment. Even more preferably, the MNP will exhibit a delayed release of CHX, with release of CHX being triggered by a change in the environment such as a drop in pH (i.e. an increase in acidity). Such a drop in pH may occur upon the formation of a bacterial biofilm so the MNPs release CHX in response to the presence of a bacterial biofilm. This may be achieved by, for example, inclusion of a component in the MNPs, or a coating on the MNPs which is responsive to changes in environmental conditions such as those mentioned above. Alternatively, the delayed release characteristics may be tailored by selection of an appropriate CHX salt, e.g. by selection of appropriate anion (s), which exhibit a change such as protonation or deprotonation upon the desired change in environmental conditions, e.g. reduction of pH. Preferably the MNPs show an inherent delayed release of CHX triggered by reduction in pH caused by the presence or formation of a bacterial biofilm.

In some cases the antimicrobial MNPs of the present invention have intrinsic antimicrobial properties. In other words, the MNPs demonstrate antimicrobial properties in addition to and augmenting the effect associated with release of soluble CHX into the environment. The observed antimicrobial efficacy is due not only to the CHX released into solution but is due to the presence of the MNPs themselves. For example, in some situations CHX hexametaphosphate MNPs appear to display inherent antimicrobial properties. In this manner, the antimicrobial MNPs of the present invention may offer antimicrobial properties over and above those of an aqueous solution of antimicrobial CHX or a composition which simply releases antimicrobial CHX into the environment without the releasing medium showing any antimicrobial efficacy.

The antimicrobial MNPs of the present invention may have various structural forms. They may be selected from particles, tubes (both single- and multi-walled), scrolls, rods, cones, hedgehog form, crystals and amorphous forms. Preferably the MNPs are particles or crystals.

The antimicrobial MNPs of the present invention have a size from 1 nm to 100 µm, preferably from 1 nm to 10 µm, preferably from 1 nm to 1 µm (i.e. nanoscale), more preferably from 5 nm to 500 nm, more preferably from 20 to 200 nm, even more preferably from 20 to 140 nm.

Colloidal Suspension of Antimicrobial Nanoparticles

According to another aspect of the invention, there is provided a colloidal suspension comprising an antimicrobial micro- or nanoparticle as described herein.

Preferably, the colloidal suspension of the present invention is a colloidal suspension in water. Water is a simple and safe solvent to work with and its biocompatibility makes the suspension safe to use in sensitive applications.

Even more preferably, the colloidal suspension of the present invention is a colloidal suspension in an aqueous solution. This may be an aqueous solution of CHX. The solution may also comprise other dissolved ions or additional components (e.g. surfactant, stabiliser, preservative etc.).

Preferably, the colloidal suspension of the present invention has an absolute value of zeta ($\zeta$) potential greater in magnitude than or equal to 15 mV, more preferably greater than or equal to 20 mV, even more preferably greater than or equal to 40 mV and particularly preferably greater than or equal to 50 mV. The zeta potential is a measure of the stability of colloidal dispersions and their tendency to form aggregates. A high absolute zeta potential value indicates a stable suspension which is less likely to coagulate or flocculate. This is a desirable property making coatings with higher uniformity easier to prepare by dip coating of a substrate.

When the absolute value or modulus of the zeta potential of the colloidal dispersion is at least 30 my, the dispersion demonstrates acceptable stability with regards to coagulation. When the absolute value of zeta potential is at least 40 mV the stability of the suspension is excellent, and the suspension would not be expected to coagulate and would only show sedimenting behaviour over a long period of time. Additionally, when the absolute value of the zeta potential is at least 20 my the MNPs exhibit desirable coating properties and may adhere to the surface of an article to provide a surface coating of antimicrobial MNPs.

Medical Article

In a further aspect of the present invention there is provided a medical article comprising antimicrobial MNPs as described herein.

The medical article of the present invention is not particularly limited and may be any article which is intended for contact with the body, either externally or internally, or for use in a medical environment such as in hospitals or doctors' surgeries. Such articles are well-known to those skilled in the art. In the present proposals, exemplary articles include various types of catheter; oral articles such as dental implants, dentures and mouthguards, wound dressings or medical packaging.

Preferably, the medical article of the present invention is a venous catheter, urinary catheter, dental implant, mouthquard, dentures, wound dressing or medical packaging. Such articles may advantageously be provided with additional antimicrobial properties by functionalisation with the antimicrobial MNPs described herein, e.g. by surface treatment to establish a surface coating comprising the MNPs on the article, or by incorporation of the MNPs into the material of the article itself.

Preferably, the medical article of the present invention is a catheter. In some aspects, the catheter is be functionalised with the antimicrobial MNPs by a surface coating. In other aspects, antimicrobial MNPs are incorporated within at least a part of the catheter during production of the materials used to make the catheter. The colonisation of catheter surfaces and surrounding tissues by bacteria such as methicillin-resistant *Staphylococcus aureus* (MRSA) is a major health problem. In catheters of the present invention which are functionalised with antimicrobial MNPs, colonisation by bacteria is prevented or reduced due to the antimicrobial activity of the MNPs.

Preferably, the medical article of the present invention is a dental implant. Dental implants are devices used to replace or augment natural bone in the mandible or maxilla (jaw bones). An abutment section of the implant protrudes from the gum and prosthetic tooth or teeth are attached to this. A problem associated with such implants is their failure in the medium to long term due to colonisation of the implant surface by bacteria and the formation of a pathogenic bacterial biofilm. In the dental implants of the present invention, the dental implant comprises antimicrobial MNPs (either as a surface coating or incorporated into the material of the dental implant itself) and this prevents or reduces the likelihood of the formation of a biofilm and makes successful incorporation of the implant without the risk of infection more likely.

Preferably, the dental implant comprises the antimicrobial MNPs in the form of a surface coating. Even more preferably, the surface of the dental implant is sparsely coated with antimicrobial MNPs. For example, area coverage of 25% or less is preferred, preferably 15% or less, more preferably 10% or less, even more preferably 5% or less. Titanium is often used to make dental implants because of the useful property of titanium to osseointegrate with bone (forming a junction between material and bone which is as strong as the bone itself). A sparse coating of MNPs on the titanium surface is advantageous because the ossecintegration can still occur to a significant extent, while still providing the antimicrobial properties associated with the MNPs. If too dense a coating is used then osseointegration is less complete and the junction between implant and bone is weaker. If too sparse a coating is used then the antimicrobial properties of the MNPs are less apparent.

The medical article may also be a wound dressing. A wound dressing comprising the antimicrobial MNPs of the present invention offers longer lasting antimicrobial efficacy than ordinary wound dressings and other known antimicrobial dressings. This is important in the dressing of wounds including acute and surgical wounds, and chronic or non-healing wounds. The antimicrobial MNPs of the present invention, particularly the CHX hexametaphosphate MNPs, are effective against *Pseudomonas aeruginosa* bacteria, the most common infectious agent in burn injuries and also against MRSA and *Streptococcus gordonii*. Functionalised wound dressings of the present invention helps to reduce the risk of infection when used to dress wounds including burn wounds and other similar wounds.

The medical article of the present invention may be a denture product including a denture or palatal obturator. A denture product or dentures is a device used in the oral cavity to replace missing teeth and/or sections of palate and restore dental function. The underside of dentures which abuts the palate is prone to infection, particularly by the yeast *Candida albicans*. In some aspects, the MNPs of the present invention, particularly the CHX hexametaphosphate MNPs, are effective against a wide variety of yeasts including *C. albicans*. When a denture product is used which comprises the antimicrobial MNPs of the present invention, there is a greatly reduced risk of infection.

The medical article of the present invention may be a mouthguard. Mouthguards are used in a variety of applications, including use in sports to protect the teeth and as a bruxism, or teeth grinding, prevention. These mouthguards are typically made of a polymer such as ethylene vinyl acetate (EVA) and are prone to the formation of bacterial biofilms on the surfaces. The mouthguards of the present invention comprise the antimicrobial MNPs described herein (either as a surface coating or incorporated into the EVA polymer) which are effective in preventing or slowing the formation of such biofilms, protecting the wearer from infection.

The medical article of the present invention may be a medical packaging, an operating theatre tray or a medical drape. Medical packaging is any kind of packaging used to enclose or protect medical equipment. Operating theatre trays are often made of stainless steel and are used to carry sterilised surgical equipment. Medical drapes may be any drapes, curtains or other textile used in a medical environment. According to the present invention, any of these may advantageously comprise antimicrobial MNPs as described herein to reduce or prevent colonisation by bacteria.

The antimicrobial MNPs may be incorporated into the medical article in various ways, which are not particularly limited.

In some situations the medical article includes a surface coating of antimicrobial MNPs. A surface coating can be easily applied by means of dip coating or spray coating. Surface coatings are effective in the protection of the external surfaces of articles which are often colonised by bacteria.

In some situations the MNPs are incorporated integrally within the article. Preferably, the medical article comprises antimicrobial MNPs embedded within at least an external surface portion of the article. The MNPs may be incorporated into the material used to make the article during manufacture, for example during the processing of a polymer for a catheter or the extrusion of the catheter tubing.

In some aspects, one or more materials that may make up a medical article may be provided with MNPs; for example, they may be dip-coated with MNPs. In some aspects, the material comprises: a polymer of medical and consumer relevance such as medical silicones, EVA, and polyurethane, an implant material such as titanium, glass, or a commercial wound dressing.

Composite Material

In a further aspect, the present invention provides a composite material comprising the antimicrobial MNPs as described herein. A composite material which comprises these antimicrobial MNPs can release CHX for an extended period as described above in relation to the MNPs themselves. This confers antimicrobial properties on these materials.

The composite material of the present invention is not particularly limited and may include any material which incorporates the antimicrobial MNPs in order to confer antimicrobial properties on that material. Exemplary materials include but are not limited to paints, pastes, polymers, hydrogels, and dental cements.

Preferably, the composite material of the present invention is a glass ionomer cement, a paint or an oral care composition. These materials may be advantageously provided with additional antimicrobial properties by including the antimicrobial MNPs within them. The following composites containing MNPs have been successfully created: glass ionomer cements, alginate films, carboxymethylcellulose films, paint, and oral care rinse/topical treatment.

Preferably, the antimicrobial MNPs are present in the composite material at up to 60 wt %, 50 wt %, 40 wt %, or 30 wt %. At levels greater than 60 wt % the composite may lose some of its intended functionality or structural properties due to the large content of MNPs. Preferably, the antimicrobial MNPs are present in the composite material at greater than or equal to 1 wt %, 5 wt %, or 10 wt %. At levels below about 1 wt % the antimicrobial properties due to the presence of the MNPs is significantly reduced but may still be adequate for some purposes.

Preferably, the composite material of the present invention is a glass ionomer cement (GIC). GICs are used in dentistry for many purposes including as a tooth-coloured filling material, as a luting and lining agent, in Atraumatic Restorative Treatment (ART), in restorations close to the gingival margin and as a fissure sealant. GICs are known to be capable of engaging in ion exchange with the oral environment. When the composite material comprising the antimicrobial MNPs described herein is a GIC, CHX leaches out of the GIC and the extended release of CHX from the MNPs may help prevent secondary caries in the area surrounding the GIC treatment. The CHX release is sustained for considerably longer than other GICs which incorporate soluble CHX salts such as CHX-diacetate or CHX-digluconate. In some aspects the GICs of the present invention may leach CHX into the environment for longer than 30 days, preferably longer than 60 days, more preferably longer than 90 days.

Traditional GICs lack antimicrobial efficacy, and secondary caries (the reoccurrence of tooth decay around or underneath the filling) is a common problem. When GICs comprise the antimicrobial MNPs of the present invention, the antimicrobial properties conferred onto the GIC can help to prevent secondary caries.

Preferably, the GIC of the present invention is able to absorb CHX from the environment. In this way, the GIC may be "recharged" with CHX to re-form the original CHX salt MNPs in the GIC when the existing supply is depleted. GICs are known to act in this way with respect to the uptake of fluoride from the oral cavity. In this manner, the antimicrobial efficacy of the GIC may continue indefinitely throughout the lifetime of the GIC, replenishing the supply of CHX salt MNPs when required. Use of the antimicrobial MNPs of the present invention means that the intervals between these replenishments can be relatively long, e.g. at least 60 or 100 days or even longer, due to the extended release of CHX.

Preferably, the antimicrobial MNPs are present in the GIC at from 1 wt % to 30 wt %, more preferably 1 wt % to 20 wt %, most preferably 1 wt % to 10 wt %. At MNP levels greater than 30 wt %, the handling properties and tensile strength of the GIC may be detrimentally affected and at levels below about 1 wt % the antibacterial action due to the presence of the MNPs is reduced.

The composite material of the present invention may be a paint. Antimicrobial paints may be used in operating theatres, dental and medical clinics, nurseries, care homes and other similar environments. Providing a paint with the long lasting antimicrobial properties demonstrated by the antimicrobial MNPs of the present invention would be highly advantageous. The antimicrobial MNPs of the present invention are efficacious against, a variety of microorganisms including methicillin-resistant *Staphylococcus aureus* (MRSA). A paint comprising the antimicrobial MNPs of the present invention offers resistance against MRSA among other infectious microbes, which is highly advantageous especially when used in the environments mentioned above.

The composite material of the present invention may be an oral care composition comprising the antibacterial MNPs as described herein. An oral care composition is a material intended for use in the oral cavity for reasons of general hygiene, or treatment of dental caries or a particular periodontal infection. Preferably, the oral care composition is a toothpaste, a protective paste, or a mouthrinse.

Method of Making an Antimicrobial Nanoparticle

In a further aspect of the present invention, there is provided a method of making an antimicrobial MNP as described herein comprising reacting an aqueous solution of CHX cations with an anion selected from one or more oxoanions and partially hydrogenated oxoanions of phosphorus, carbon, nitrogen, and sulphur. Preferably the anion is selected from oxoanions of phosphorus, carbon, nitrogen, and sulphur, and more preferably the anion is at least one selected from phosphates, carbonate, nitrate and sulfate. Mixing is preferably in a molar ratio of CHX cations: selected anion of from 1:100 to 100:1 to produce a colloidal suspension of micro- or nanoparticles.

Preferably, the two reactants are present at equimolar concentrations, i.e. 50:50. At equimolar reactant concentrations, the resultant colloidal suspension has satisfactory colloid size and zeta potential. Preferably, the concentration of the CHX cation in the reaction mixture is about 5 mM. Preferably, the concentration of the anion as described above in the reaction mixture is about 5 mM.

Preferably, the method comprises reacting an aqueous solution of CHX cations with a phosphate anion selected from orthophosphate, pyrophosphate, triphosphate and hexametaphosphate. Even more preferably, the method comprises reacting an aqueous solution, of CHX cations with hexametaphosphate anions. Using HMP produces a colloidal suspension with good zeta potential and size properties, and good solubility.

Preferably, the HMP reactant is freshly prepared HMP, e.g. prepared 60 minutes or less before use, to avoid risk of unwanted hydrolysis of the reagent before use. In some aspects, one or more additional anions may be present in the reaction mixture. In some aspects, one or more additional cations (in addition to CHX) may also be present in the reaction mixture.

Additional components may also be present in the reaction mixture. These may be components which are intended to be incorporated into the MNPs, or components which help to prevent agglomeration of the MNPs, e.g. by coating the MNPs after formation. Preferably, polyethylene glycol (PEG) is present in the reaction mixture as an agglomeration preventative agent. In some cases PEG is coated onto the surface of the MNPs after formation.

Preferably, the reaction mixture is rapidly stirred throughout the mixing and MNP formation processes.

In certain aspects, the MNPs are retrieved from the colloidal suspension in a further step. This may be achieved by centrifugation at around 21000 g for 60 mins followed by removal of the supernatant and drying at 40-60° C. for a few days. The resultant particles may then be removed and ground to a fine powder to give MNP aggregates.

Alternatively, KCl solution at around 1M concentration may be added to the suspension and left for around 15 mins. This creates charge layer compression, causing the MNPs to sediment. Removal of the supernatant followed by centrifugation at around 5000 g for 10 mins gives a paste after removal of the supernatant. This may optionally be dried to produce the MNPs.

Method of Using Antimicrobial Nanoparticle

According to a further aspect of the present invention, there is provided a method of forming a surface coating of the antimicrobial MNPs as described herein, comprising immersing the article in a colloidal suspension of the MNPs, removing the article from the suspension and optionally rinsing the article with deionised water and drying.

Preferably, during immersion of the article in the suspension, the suspension is rapidly stirred, e.g. at about 150 rpm.

Preferably, the article is immersed in the colloidal suspension for a period of from 1 s to 30 mins. The MNP coverage achieved is related to the immersion time, so if a denser coverage is required the immersion time should be extended accordingly.

Optionally, the article is rinsed with deionised water after immersion. Rinsing removes excess MNPs from the surface of the article. Preferably, the article is rinsed for a period of from is to 30 s. The MNP coverage achieved is related to the rinsing time, so if a denser coverage is required the rinsing time should be reduced accordingly or the rinsing step can be eliminated.

The CHX-HMP MNPs and/or materials functionalised with the CHX-HMP MNPs have efficacy against, a number of microbes, including MRSA, *E. coli, P. aeruginosa, K. pneumonia, A. baumanii, S. gordonii, P. gingivalis*, and *C. albicans*. A number of methods and assays have been used to assess the antimicrobial efficacy, such as total viable counts (colony-forming units), time-kill assays, zones of inhibition, live/dead viability testing, and imaging using a range of microscopy techniques.

In respect of numerical ranges disclosed in the present description it will of course be understood that in the normal way the technical criterion for the upper limit is different from the technical criterion for the lower limit, i.e. the upper and lower limits are intrinsically distinct proposals.

For the avoidance of doubt it is confirmed that in the general description above, in the usual way the general preferences and options described in respect of different features of the MNPs, articles, compositions and methods are independently described and may be combinable in other combinations of features insofar as they are compatible.

EXAMPLES

The following examples are illustrative of the present invention.

Examples 1-6; Comparative Examples 1-3: Elution of CHX from Functionalised Borosilicate Glass Surfaces Chlorhexidine based salts were prepared by combining, at room temperature and under rapid stirring, 100 mL chlorhexidine (as the digluconate salt in aqueous solution at a concentration of 10 mM) and 100 mL of one of a range of anions in aqueous solution, also at an initial concentration of 10 mM, to effect final total concentrations of 5 mM of each. The anions used are shown in Table 1.

TABLE 1

| Shorthand name | Reagent | Supplier |
|---|---|---|
| Orthophosphate | Disodium hydrogen orthophosphate | Fisher Scientific, Loughborough, UK |
| Pyrophosphate | Tetrasodium pyrophosphate pentabasic | Fisher Scientific |
| Triphosphate | Sodium triphosphate pentabasic | Sigma Aldrich, Gillingham, UK |
| Hexametapoosphate | Sodium hexametaphosphate | Sigma Aldrich |
| Carbonate | Calcium carbonate | Fisher Scientific |
| Nitrate | Calcium nitrate tetrahydrate | Sigma Aldrich |

The precipitate was then allowed to adhere on borosilicate glass coverslips. Coverslips (Agar Scientific, Stansted, UK) were cleaned by 10 minutes ultrasonication in acetone followed by 10 minutes ultrasonication in industrial methylated spirits and allowed to air dry. They were immersed in the 200 mL suspension described above while it was rapidly stirred using a magnetic stirring plate. Coverslips were immersed for 30 seconds, removed, immersed in deionised water for 10 seconds to rinse, blotted to remove excess liquid and allowed to dry in air.

The resultant glass surface with CHX-based deposits was investigated using scanning electron microscopy (SEM) and atomic force microscopy (AFM). A benchtop SEM (Phenom, Eindhoven, Netherlands) and an AFM (Nanoscope IIIa, Digitial Instruments, CA, USA) operating in tapping mode with silicon nitride cantilevers were used to examine the surface. Specimens were coated with a gold-palladium layer using a sputter coater prior to SEM.

The elution of soluble CHX from the functionalised glass surfaces was examined using ultraviolet spectrophotometry. 8 specimens of each type were placed in individually labelled cuvettes suitable for ultraviolet spectrophotometry. 2.5 mL deionised water was added to the cuvettes and they were sealed tightly using cuvette lids. These were agitated on an orbital shaker rotating at 150 rpm. The cuvettes were kept sealed and were sampled for chlorhexidine concentration at intervals over a 14-day period. Control sets were prepared where the specimens had been immersed only in deionised water and were they had been immersed only in a 25 µM or 5 mM CHX solution; 25 µM is the concentration of soluble CHX residual in the CHX-HMP suspension and 5 mM is the total concentration of (soluble and bound) CHX in the preparations.

Figure 2:
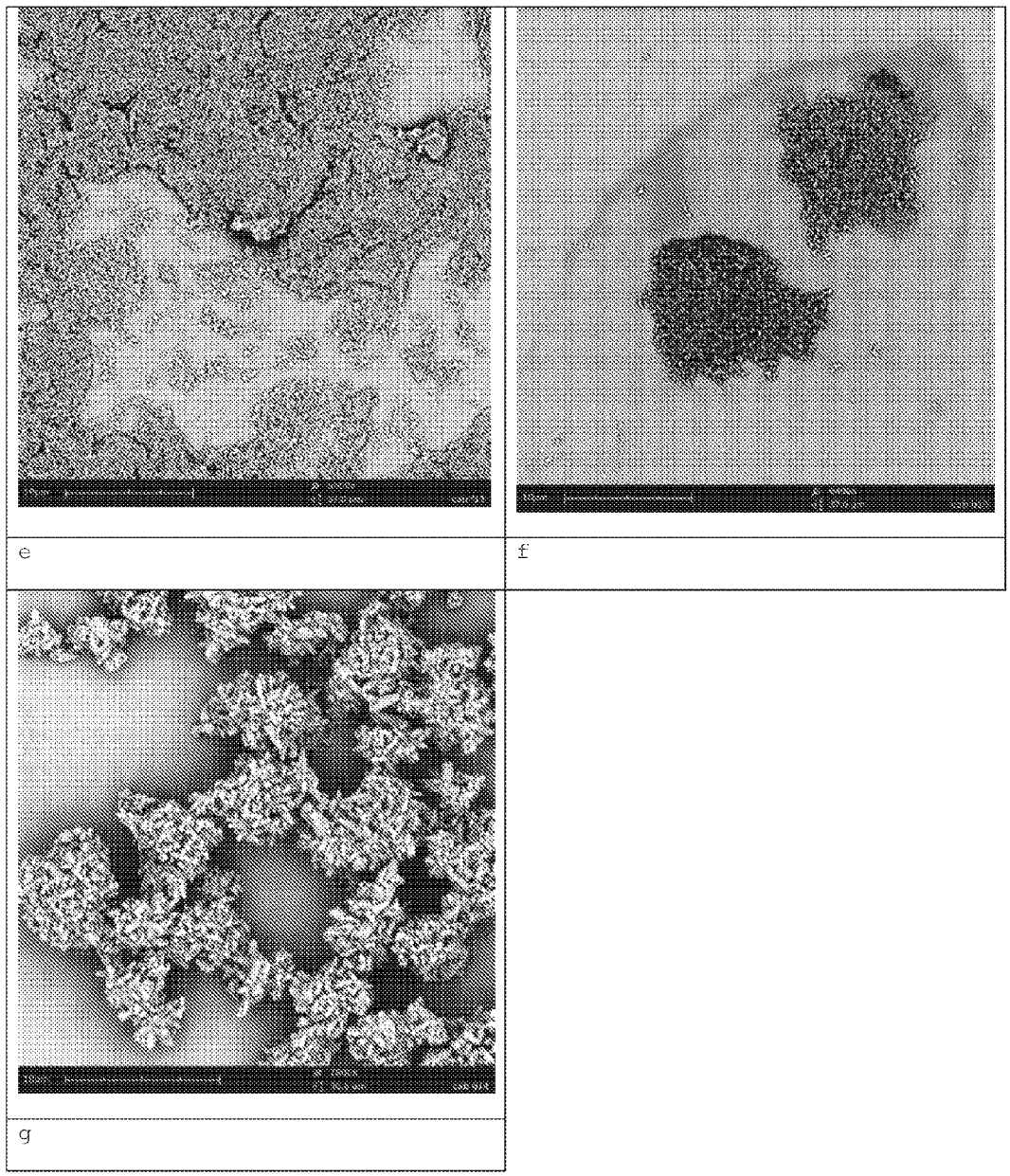
FIG. 2. shows SEM micrographs of borosilicate glass coverslips after immersion in the following compositions. (e) 5/5 CHX-HMP [10 $\mu$m, 6500×]; (f) 5/5 CHX-nitrate [10 $\mu$m, 6400×]; (g) 5/5 CHX-carbonate [10 $\mu$m, 7800×].
Figure 3:
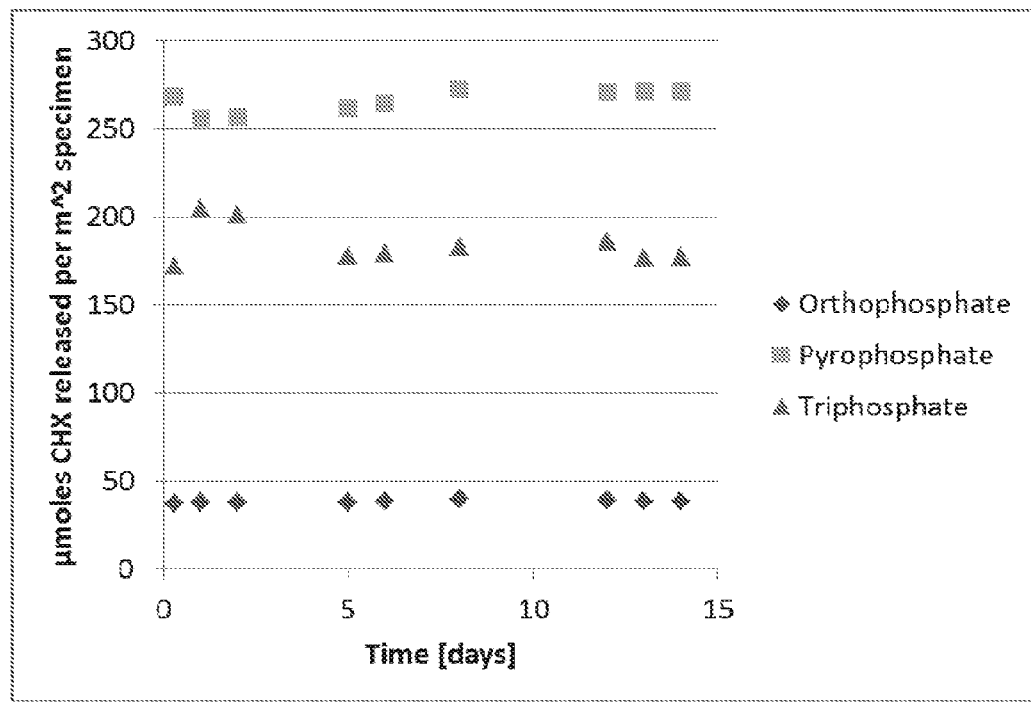
FIG. 3 shows CHX elution profiles of orthophosphate, pyrophosphate and triphosphate specimens.
Figure 4:
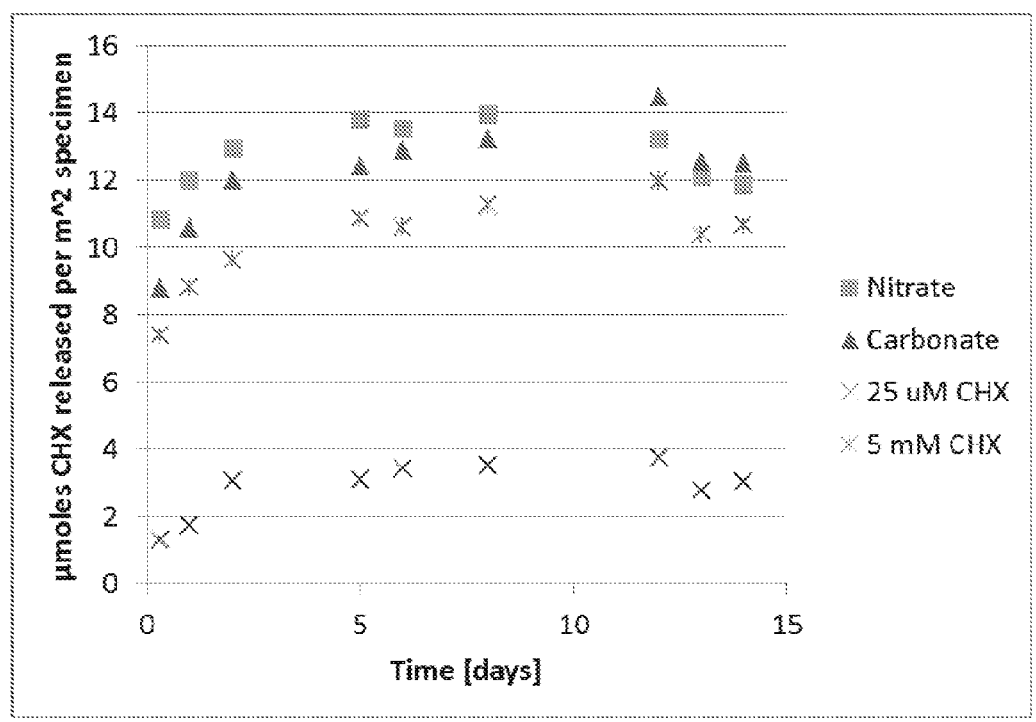
FIG. 4 shows CHX elution profiles of nitrate and carbonate specimens, along with control specimens which were exposed to 25 $\mu$M and 5 mM CHX solutions respectively.

SEM images of the specimens are shown in FIGS. 1-2. CHX elution profiles of the specimens are shown in FIGS. 3-4. All specimens released soluble CHX.

Table 2 shows the CHX release properties of the various CHX salts tested.

TABLE 2

| | Coating Medium | CHX Release Period |
|---|---|---|
| Example 1 | 5/5 CXH-orthophosphate | Immediate release only, no sustained release |
| Example 2 | 5/5 CHX-pyrophosphate | Immediate release only, no sustained release |
| Example 3 | 5/5 CHX-triphosphate | Immediate release only, no sustained release |
| Example 4 | 5/5 CHX-hexametaphosphate | >14 days |
| Example 5 | 5/5 CHX-carbonate | 48-72 hrs |
| Example 6 | 5/5 CHX-nitrate | 48-72 hrs |
| Comparative Example 1 | Deionised water | N/A |
| Comparative Example 2 | 25 µM CHX | 48-72 hrs |
| Comparative Example 3 | 5 mM CHX | 48-72 hrs |

Example 1—CHX-Orthophosphate

The CHX-orthophosphate (CHX-OP) functionalised specimens displayed some areas with a self-assembled porous matrix deposit, but also the unusual structures seen in FIG. 1b and FIG. 3a. These were composed of arrangements of elongated crystallites which originate from a central point and extend radially from this point ("hedgehog" forms). These structures were typically 30-50 µm in diameter and the individual crystallites were approximately 0.50-1 µm wide. The crystallites were often slightly curved.

Example 2—CHX-Pyrophosphate; Example 3—CHX-Triphosphate; Example 4—CHX-Hexametaphosphate The specimens functionalised with CHX-pyrophosphate (CHX-PP), CHX-triphosphate (CHX-TP) and CHX-HMP all exhibited similar deposits of a self-assembled porous matrix. This appeared dense and a more widespread coverage on the CHX-PP and CHX-TP than the CHX-HMP.

The orthophosphate, pyrophosphate and triphosphate salts of CHX exhibited the highest CHX release. These were able to effect a very large release of CHX over a short time, which was much greater and faster than the release observed with those specimens exposed simply to a CHX solution. The highest release was seen from pyrophosphate, an intermediate level from triphosphate and the lowest, from orthophosphate, although even this was around 4× the magnitude of CHX release seen from other specimens tested. The release in all cases occurred at the initial time with no evidence of sustained release. These particles could be used in materials for which a large dose of antimicrobial is required topically. An example might be a decontamination treatment for a medical device such as a palatal obturator or denture.

The hexametaphosphate salts of CHX exhibited the lowest total release of any of the anions, but this was sustained for the duration of the experiment (14 days) and was still ongoing at the conclusion of the measurements. In another, longer, experiment the CHX hexametaphosphate salts showed release over at least a 90 day period. These particles might find application in those materials which are required to have antimicrobial efficacy over longer periods, such as indwelling catheters, cannulas and implants.

Example 5—CHX-Carbonate; Example 6—CHX-Nitrate

The specimens exposed to the CHX-carbonate preparation exhibited spontaneously formed nanotube structures arranged in roughly spherical formations (FIG. 2g). They were predominantly single-wall tubes but in some areas double-wall nanotubes, or nanotubes-within-nanotubes, could be seen.

The deposits observed on the CHX-nitrate functionalised specimens were sparsely distributed and most areas appeared featureless in the SEM.

The nitrate and carbonate salts of CHX exhibited a lower release of CHX than the orthophosphate, pyrophosphate and triphosphate and the release continued over a few days. Nitrate and carbonate specimens released CHX and this release was sustained for around 48-72 h; after this time the concentration of CHX stabilised and the release can be considered to have come to completion. These might find application in a product which requires antimicrobial efficacy over this period, such as a wound dressing or suture.

Comparative Examples 1-3

The glass surfaces treated with water or aqueous CHX solutions appear featureless and flat (FIG. 1a). Both CHX treated specimens released CHX and this release was sustained for around 48-72 h; after this time the concentration of CHX stabilised and the release can be considered to have come to completion (FIG. 4).

Examples 7-14; Comparative Examples 4-7: Elution of CHX from CHX-HMP Functionalised Materials Synthesis and Characterisation of Nanoparticles CHX-HMP nanoparticles (Nips) were prepared by combining, at room temperature and under rapid stirring, CHX (as the digluconate salt in aqueous solution) and HMP (as the sodium salt in aqueous solution) to effect final total concentrations of 5 and 5 or 0.5 and 0.5 mM of each. These will henceforth be referred to as CHX-HMP-5 and CHX-HMP-0.5.

Mixing the two reagents resulted in the formation of a colloidal suspension. The particle size and zeta potential of the nanoparticles in the colloidal suspensions were characterised using dynamic light scattering (DLS) as a function of time and electrophoretic mobility (Malvern Zetasizer, Malvern, UK).

Preparation and Characterisation of Nanoparticle-Functionalised Materials

Specimens of a range of materials were coated with the nanoparticles. The materials used are shown in Table 3.

TABLE 3

| Example | Shorthand name | Description | Preparation | Supplier |
|---|---|---|---|---|
| 7, 8 | Glass | 12 mm diameter circular borosilicate glass coverslips | 10 min ultrasonication in acetone, 10 min ultrasonication in industrial methylated spirits, air dry | Agar Scientific, Stansted, UK |
| 9, 10 | Alginate wound dressing | 10 × 7 mm sections of a commercially available wound dressing containing alginate fibres | Used as supplied | "Savlon Alginate Dressings", Novartis Consumer Health, Horsham, UK |
| 11, 12 | EVA polymer | 7 × 7 × 3 mm ethylene vinyl acetate sections | 10 min ultrasonication in industrial methylated spirits, air dry | Data Plastics, Witney, UK |
| 13, 14 | Titanium | 10 × 10 × 1 mm square sections of grade 2 commercially pure titanium, | Polished using 80 grit silicon carbide paper, 10 min ultrasonication in acetone, 10 min ultrasonication in industrial methylated spirits, air dry | Titek, Sutton Coldfield, UK |

200 mL of the colloidal suspension was prepared using freshly-prepared reagents (to prevent hydrolysis of the HMP). The specimen was immersed in the rapidly stirred colloid for 30 s, then removed and immersed in deionised water for 10 s to rinse, and then blotted to remove excess liquid and allowed to dry in air.

The nanoparticle-functionalised surfaces were examined using atomic force microscopy (ATM; Nanoscope IIIa, Digital Instruments, CA, USA) for those with suitable surfaces (glass, titanium) but not for those with very rough or uneven surfaces (alginate dressing, EVA polymer). All specimens were examined using scanning electron microscopy (SEM) (Phenom, Eindhoven, Netherlands) after coating with gold-palladium alloy using a sputter coating unit (SC7620, Emitech, Taiwan). Since neither glass nor titanium were atomically flat surfaces it was difficult to distinguish between small (<20 nm) surface features and small nanoparticles; for this reason the CHX-HMP-5 and CHX-HMP-0.5 nanoparticles were also deposited on freshly cleaved mica to resolve the smallest among them.

8 specimens of each material coated with CHX-HMP-5 and CHX-HMP-0.5 nanoparticles were placed in individually labelled cuvettes suitable for ultraviolet spectrophotometry. Deionised water was added to the cuvettes and they were sealed tightly using cuvette lids. These were agitated on an orbital shaker rotating at 150 rpm. The cuvettes were kept sealed and were sampled for chlorhexidine concentration at intervals over a 60-90 day period. Control sets were prepared where the specimens were immersed in deionised water and where they were immersed in a 25 µM CHX solution, which is the concentration of aqueous CHX residual in the CHX-HMP-5 colloidal suspension.

Optional Retrieval of NPs from Colloidal Suspension

Optionally, NPs may be retrieved from the suspension after the reaction has been carried out. This was not done in the case of the present. Examples, however it may be achieved by one of the following options:

1) Place in high-g centrifuge tubes or Eppendorfs and centrifuge at 21000 g for 60 min. This gives a moderate separation; there is still evidence of NPs remaining in the supernatant seen as a slightly cloudy liquid. Remove the supernatant and discard then either use the NP paste or dry in an oven at 40-60 degrees over a few days, scrape out and grind to a fine white powder, giving aggregates of NPs. These can be added for example to dental cements or other materials.

2) Alternatively to 250 mL 5/5 colloidal suspension add 25 mL 1 M KCL, leave for 15 min and the bulk of the NPs will sediment at the bottom of the vessel owing to charge layer compression. Decant and discard the supernatant and gather the densely populated liquid at the bottom into centrifuge vessels. Centrifuge at 5000 g for 10 min. This gives a much more effective separation owing to the compression of the charge layer around the NPs and can be used to process larger quantities of NPs with more typical laboratory equipment. The paste can be scraped out after the supernatant is discarded and can be used for instance to add to paints or other materials. Alternatively the paste can be dried and used as described above.

The dominant particle size and zeta potential of the CHX-HMP-0.5 and CHX-HMP-5 suspensions are shown in Table 4.

TABLE 4

| Nanoparticle preparation | Particle size [nm] (standard deviation) | Zeta potential [mV] (standard deviation) |
| --- | --- | --- |
| CHX-HMP-0.5 | 122 (47) | −39.6 (3.2) |
| CHX-HMP-5 | 141 (44) | −47.5 (6.5) |

Figure 9:
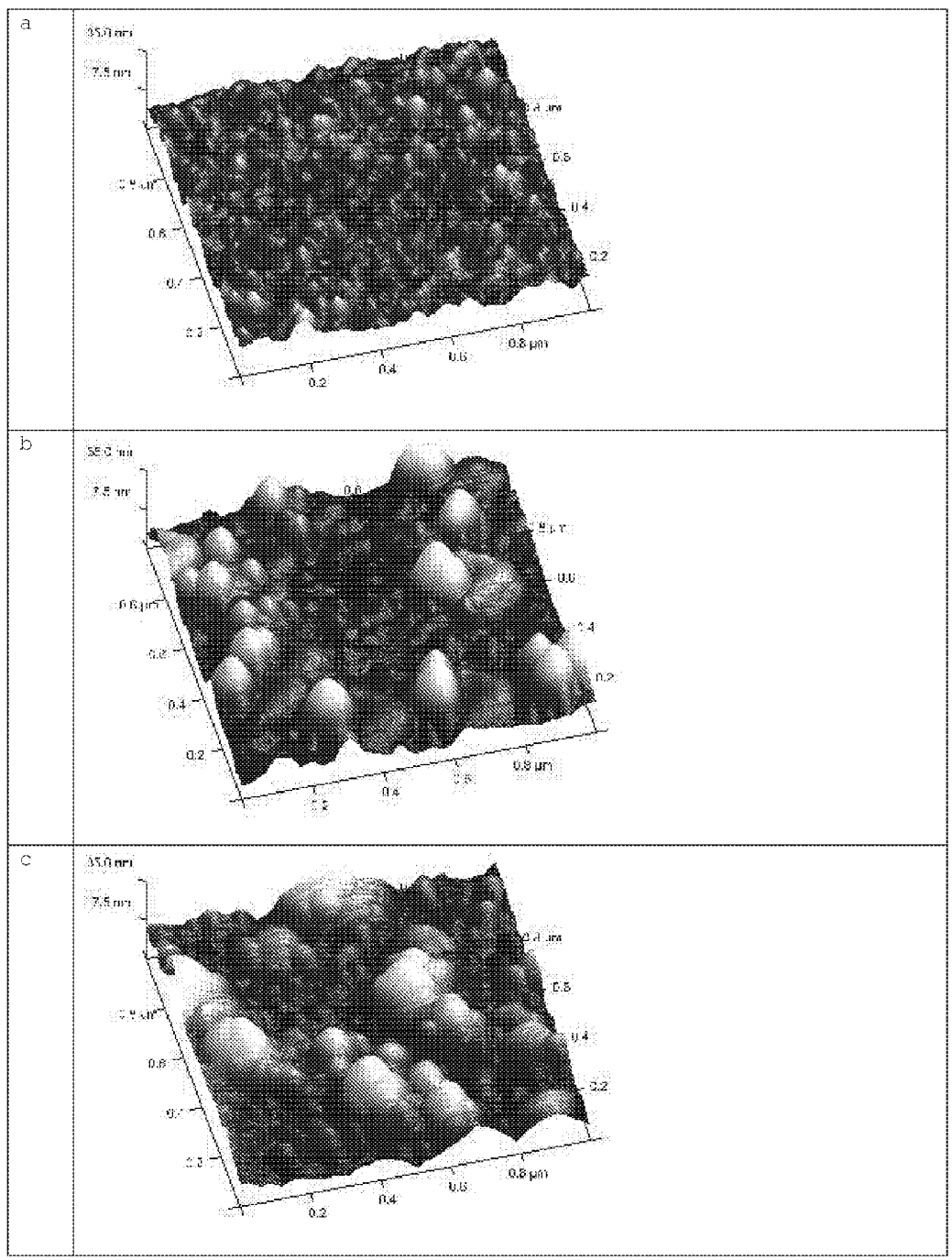
FIG. 9 shows AFM images of the following titanium surfaces some of which have been treated with MNPs (horizontal scale 1 $\mu$m, vertical scale 55 nm). (a) polished Ti surface; (b) CHX-HMP-0.5 MNPs; (c) CHX-HMP-5 MNPs.
Figure 10:
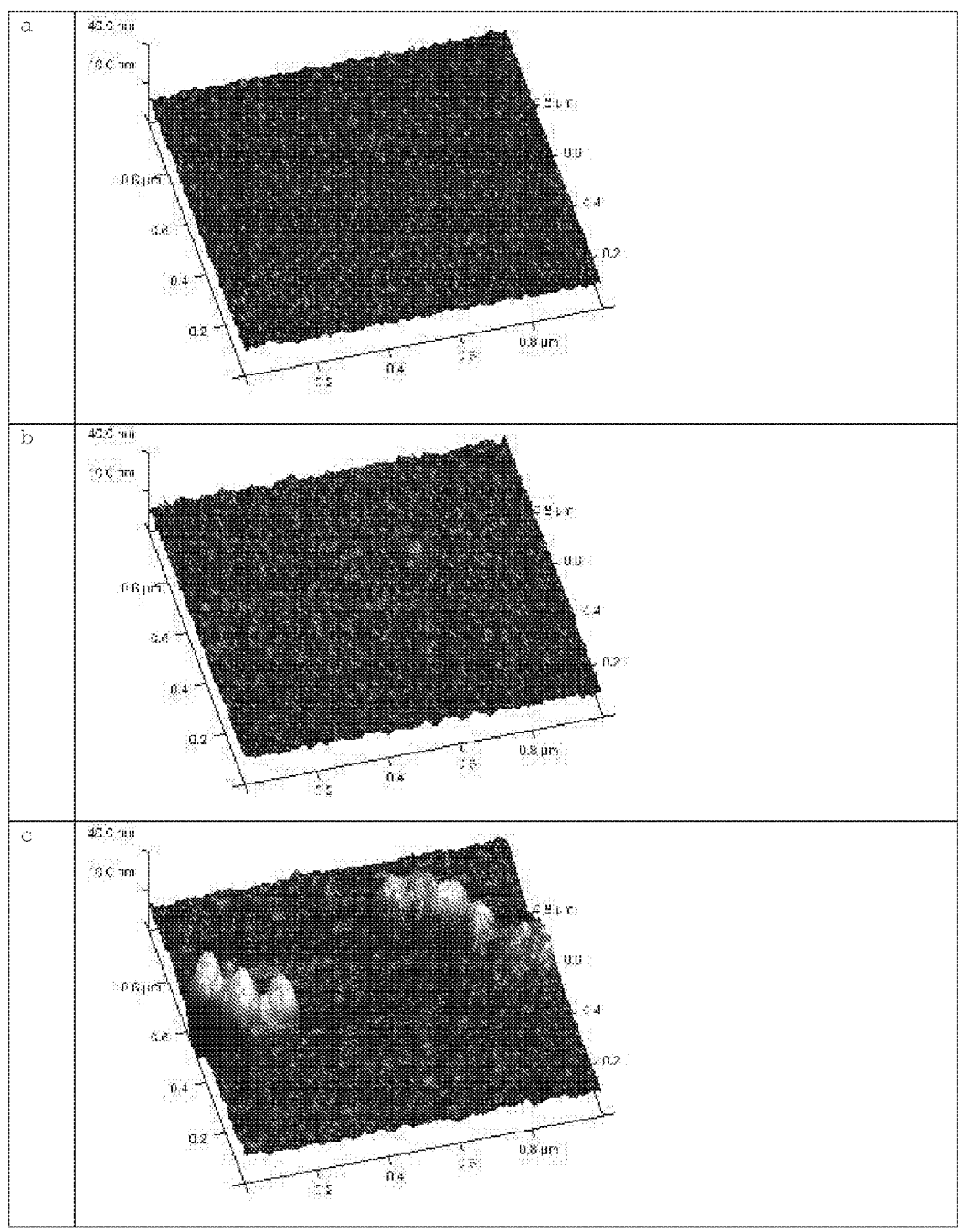
FIG. 10 shows AFM images of the following glass surfaces some of which have been treated with MNPs (horizontal scale 1 $\mu$m, vertical scale 60 nm). (a) cleaned untreated glass; (b) CHX-HMP-0.5 MNPs; (c) CHX-HMP-5 MNPs.
Figure 11:
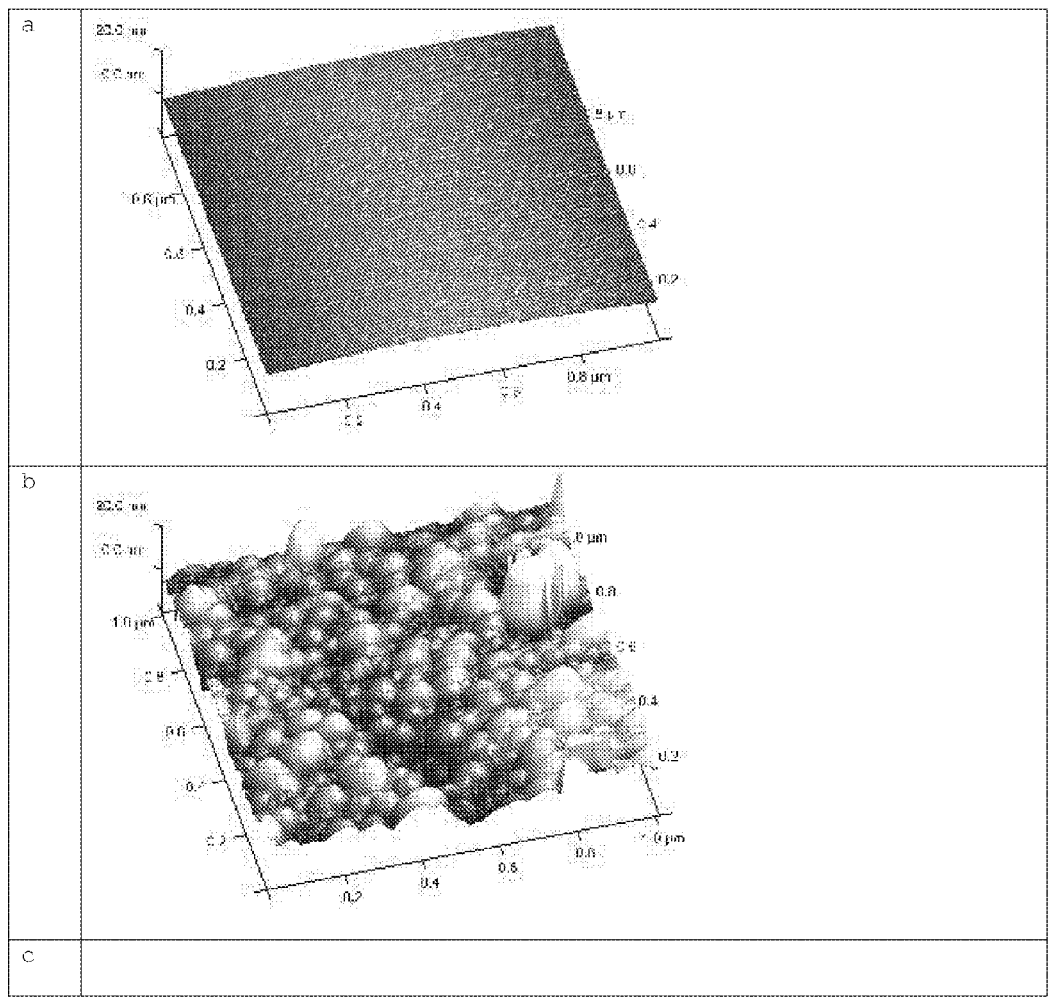
FIG. 11 shows AFM images of the following mica (ultraflat) surfaces some of which have been treated with MNPs (horizontal scale 1 $\mu$m, vertical scale 20 nm). (a) cleaned untreated glass; (b) CHX-HMP-0.5 MNPs.

The DLS indicated a bi-modal size distribution with some specimens in which a second peak of much smaller diameter was observed at around 20-60 nm. SEM images of the nanoparticle-functionalised surfaces are shown in FIGS. 5-8 and AFM of functionalised glass, titanium and mica surfaces are shown in FIGS. 9-11. The titanium and glass specimens exhibit nanoscale roughness which makes it impossible to distinguish the substrate surface from nanoparticles with diameter less than around 40 nm, but the control mica surface is atomically flat and these images give clear indications of a confluent layer of nanoparticles with diameters of typically 20-100 nm.

Chlorhexidine elution from the nanoparticle-functionalised surfaces is shown in FIGS. 12-15.

The different material specimens investigated were successfully functionalised with CHX-HMP antimicrobial nanoparticles, and exhibited a gradual leaching of soluble CHX over a period of up to 90 days. The SEM and AFM images in FIGS. 5-11 give a clear visualisation of individual nanoparticles and spontaneously self-assembled porous nanoparticle aggregates on most surfaces.

Table 5 shows the CHX release periods for the different functionalised materials. For CHX release quantities, see FIGS. 12-15.

TABLE 5

| | Material | Coating Medium | CHX Release Period |
| --- | --- | --- | --- |
| Example 7 | Glass | CHX-HMP-5 | >90 days |
| Example 8 | Glass | CHX-HMP-0.5 | 20-25 days |
| Example 9 | Alginate Dressing | CHX-HMP-5 | >50 days |
| Example 10 | Alginate Dressing | CHX-HMP-0.5 | >50 days |
| Example 11 | EVA Polymer | CHX-HMP-5 | >80 days |
| Example 12 | EVA Polymer | CHX-HMP-0.5 | ~20 days |
| Example 13 | Titanium | CHX-HMP-5 | >60 days |
| Example 14 | Titanium | CHX-HMP-0.5 | 5 days |
| Comparative Example 4 | Glass | 25 µM CHX solution | No release |
| Comparative Example 5 | Alginate Dressing | 25 µM CHX solution | >60 days |
| Comparative Example 6 | EVA Polymer | 25 µM CHX solution | No release |
| Comparative Example 7 | Titanium | 25 µM CHX solution | Little or no significant release |

Example 7—Glass Functionalised with CHX-HMP-5

Example 8—Glass Functionalised with CHX-HMP-0.5

Comparative Example 4—Glass Exposed to Control 25 µM CHX Solution

Figure 6:
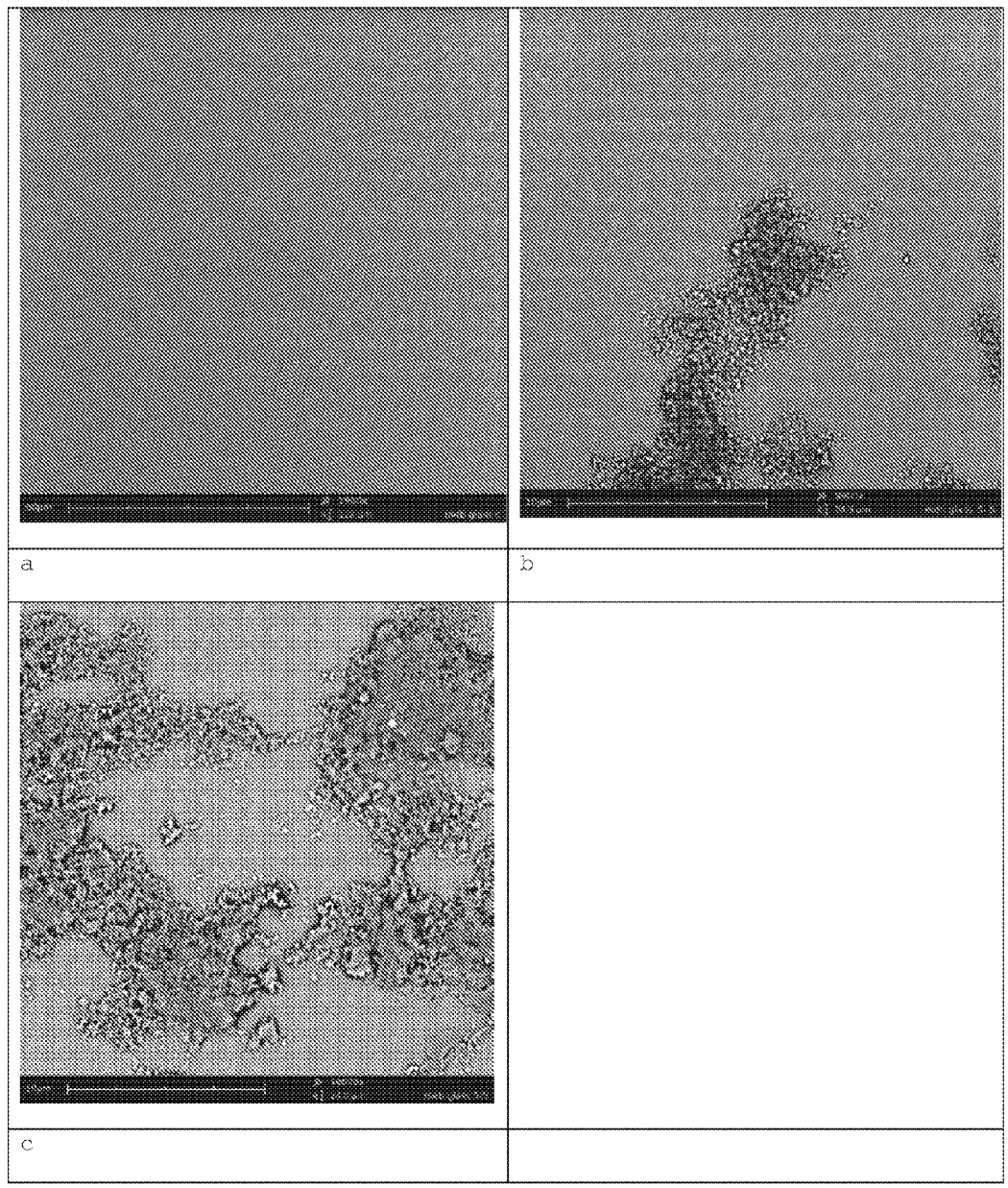
FIG. 6 shows the following SEM micrographs of borosilicate glass covers lips. (a) control specimen, no MNPs [60 $\mu$m, 1980×]; (b) CHX-HMP-0.5 MNPs [10 $\mu$m, 9900×]; (c) CHX-HMP-5 MNPs [10 $\mu$m, 10000×].

The nanoparticle functionalised glass surfaces released CHX over the experimental period (FIG. 13), and the CHX released related to the initial density of the nanoparticles and nanoparticle aggregates, with the more densely coated CHX-HMP-5 surfaces exhibiting a higher, and more prolonged, release than the less densely coated CHX-HMP-0.5 surfaces (FIG. 6). For the CHX-HMP-0.5 specimens, the release of soluble CHX ceased after approximately 20-25 days, whereas for the CHX-HMP-5 specimens the release was still continuing at the 90 day point. The control group treated with 25 µM CHX did not show any CHX release indicating that the soluble CHX was fully removed by the rinsing step and therefore that the CHX release observed with the nanoparticle-functionalised specimens was owing to the presence of these nanoparticles. This development may find application in glass-containing and glass-like biomedical and consumer products which would benefit from a prolonged antimicrobial functionality such as glass ionomer cements, a dental filling material which comprises glass particles embedded in a cement matrix.

Example 9—Alginate Wound Dressing Functionalised with CHX-HMP-5

Example 10—Alginate Wound Dressing Functionalised with CHX-HMP-0.5

Figure 5:
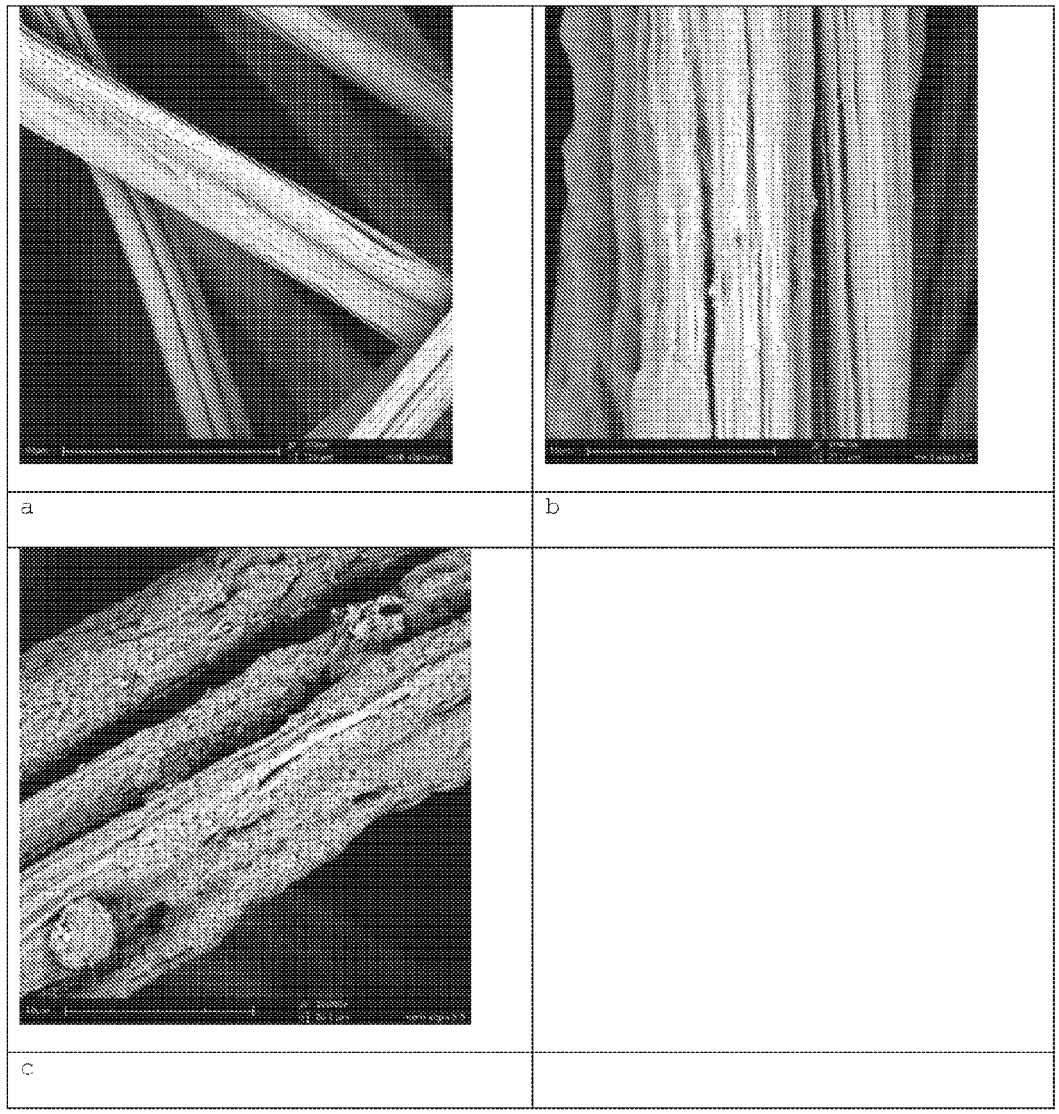
FIG. 5 shows the following SEM micrographs of alginate wound dressing. (a) control specimen, no MNPs [60 $\mu$m, 2000×]; (b) CHX-HMP-0.5 MNPs [10 $\mu$m, 10400×]; (c) CHX-HMP-5 MNPs [10 $\mu$m, 10000×].
Figure 12:
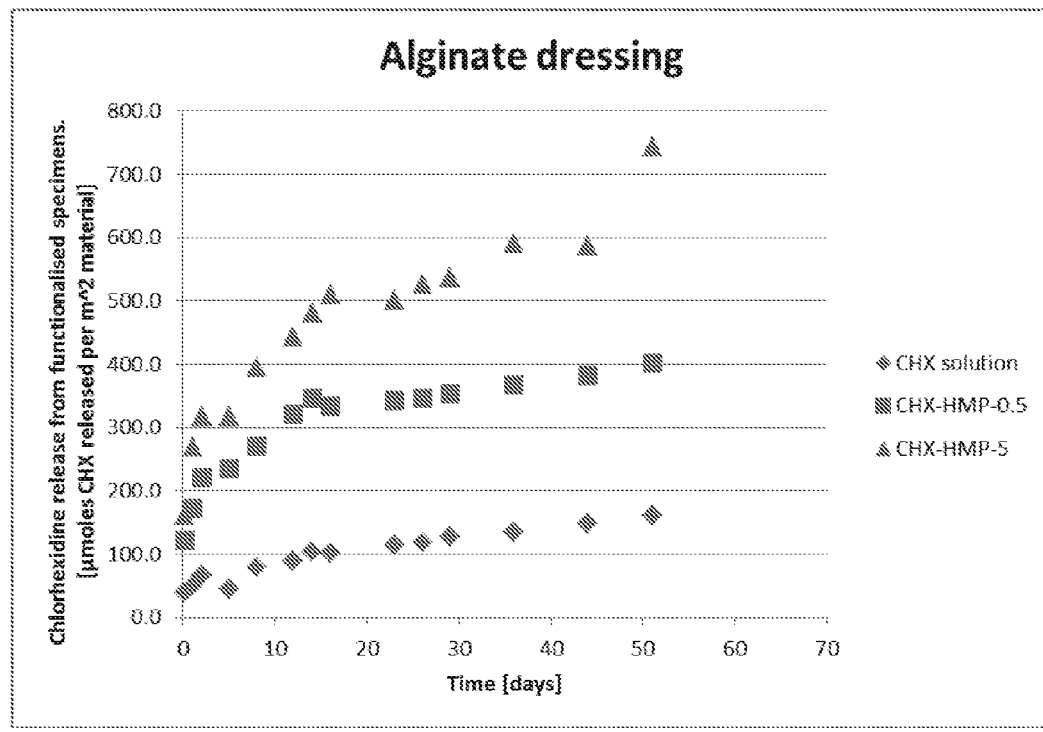
FIG. 12 shows the CHX elution profiles from alginate dressings treated with control (25 $\mu$M CHX) solution, CHX-HMP-0.5 and CHX-HMP-5.
Figure 13:
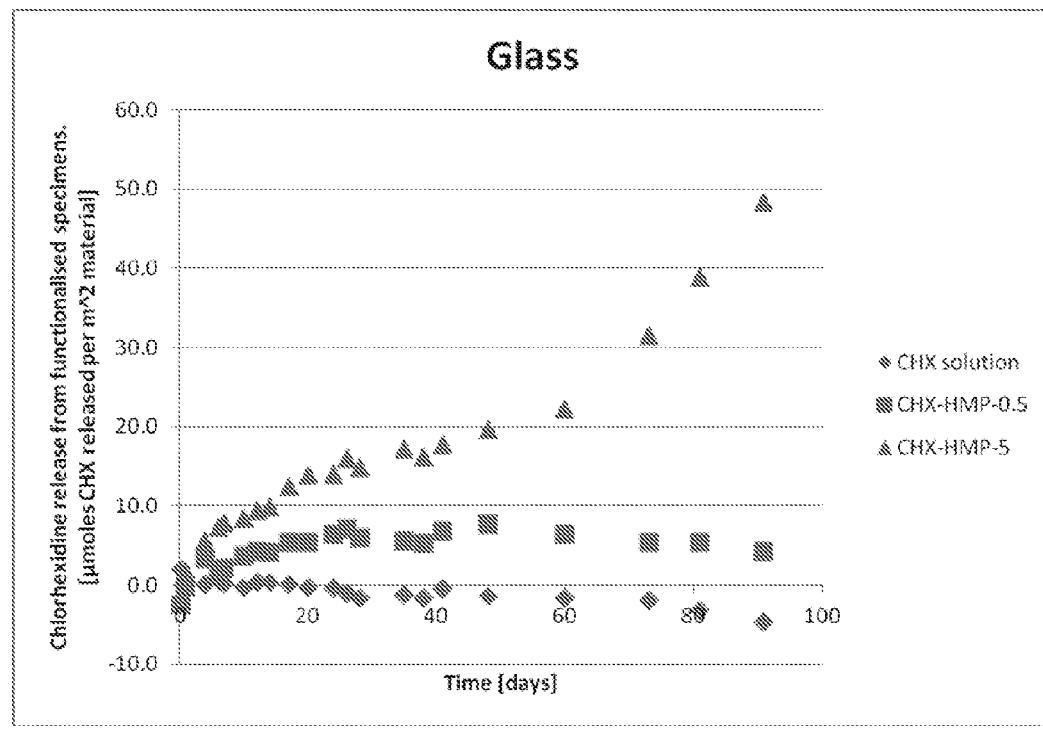
FIG. 13 shows the CHX elution profiles from glass treated with control (25 $\mu$M CHX) solution, CHX-HMP-0.5 and CHX-HMP-5.
Figure 14:
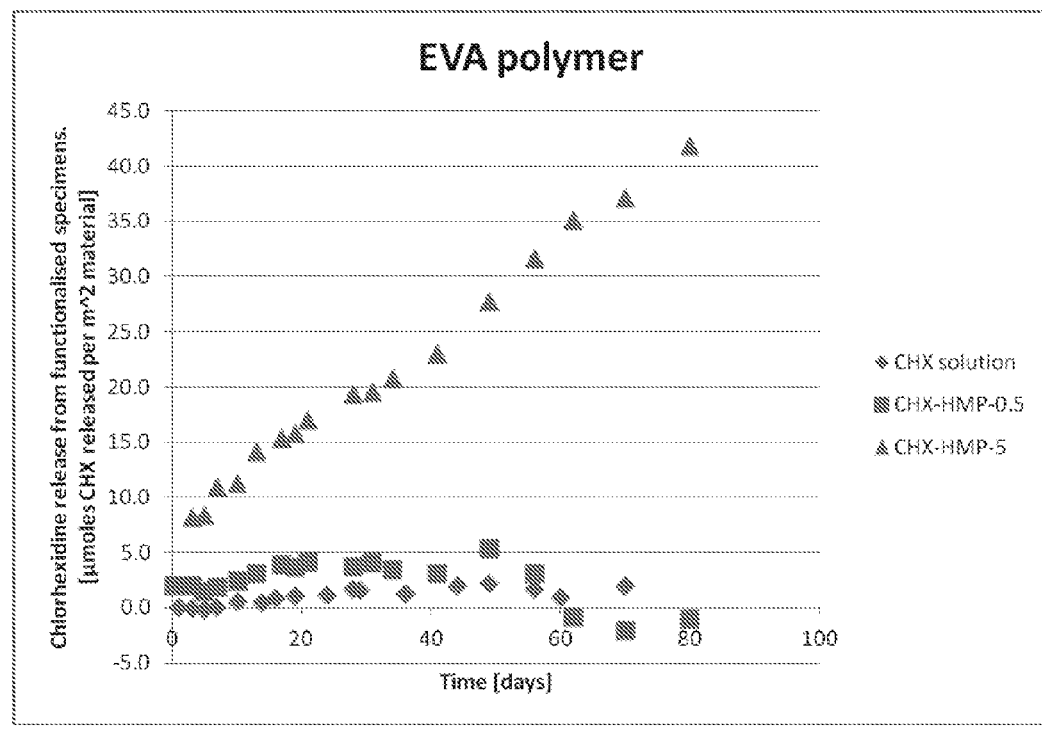
FIG. 14 shows the CHX elution profiles from EVA polymer treated with control (25 $\mu$M CHX) solution, CHX-HMP-0.5 and CHX-HMP-5.
Figure 15:
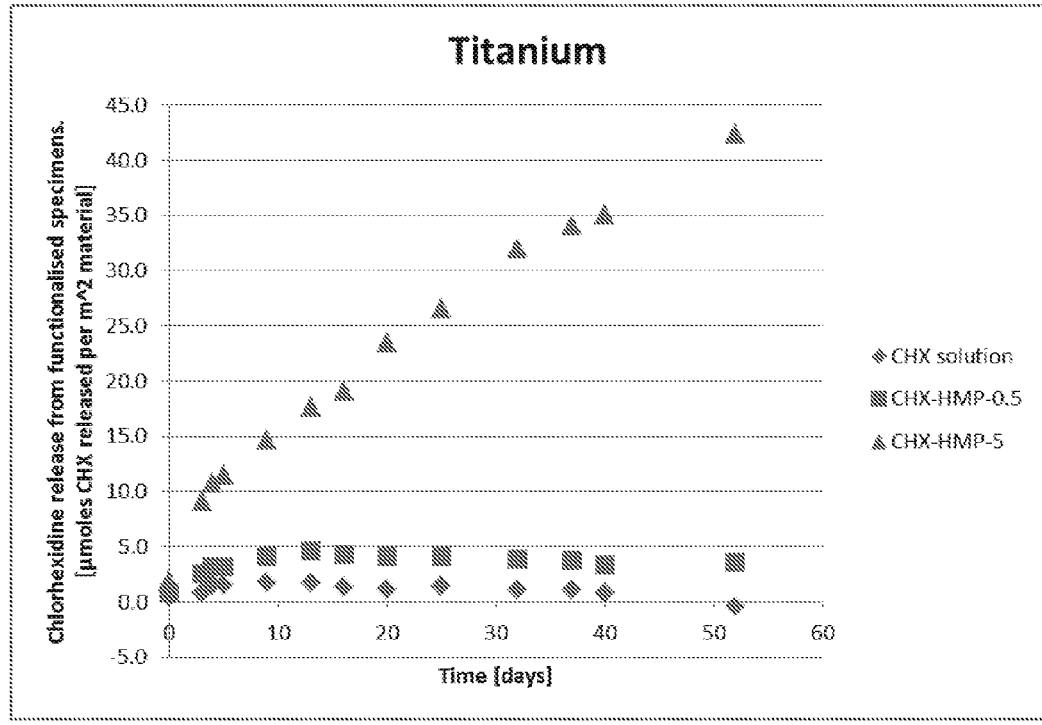
FIG. 15 shows the CHX elution profiles from titanium treated with control (25 $\mu$M CHX) solution, CHX-HMP-0.5 and CHX-HMP-5.

Comparative Example 5—Alginate Wound Dressing Exposed to Control 25 µM CHX Solution The highest CHX release, when normalised to surface area, was from the alginate wound dressing (FIG. 12). The SEM images clearly show a dense coating of nanoparticle aggregates on almost all fibres with the CHX-HMP-5 nanoparticles, and a sparser distribution on the specimens coated with CHX-HMP-0.5 nanoparticles (FIG. 5). There was some release of CHX from the specimen treated with the control 25 µM CHX solution, indicating that the material absorbed some soluble CHX from the solution, but the amount of CHX released from the control specimens was much smaller than that seen from the nanoparticle-functionalised specimens (FIG. 12). There was a dose-response relationship whereby the CHX-HMP-5 specimens exhibited a larger release than the CHX-HMP-0.5 specimens, and this correlated with a more widespread coverage of nanoparticles with the CHX-HMP-5 preparation (FIG. 5). For both the CHX-HMP-5 and CHX-HMP-0.5 specimens the release was still ongoing at the conclusion of the experiment indicating that the nanoparticles were not depleted at this time. These findings may be useful in developing wound dressings that protect chronic or non-healing wounds from infection.

Example 11—EVA Polymer Functionalised with CHX-HMP-5

Example 12—EVA Polymer Functionalised with CHX-HMP-0.5

Comparative Example 6—EVA Polymer Exposed to Control 25 µM CHX Solution

Figure 7:
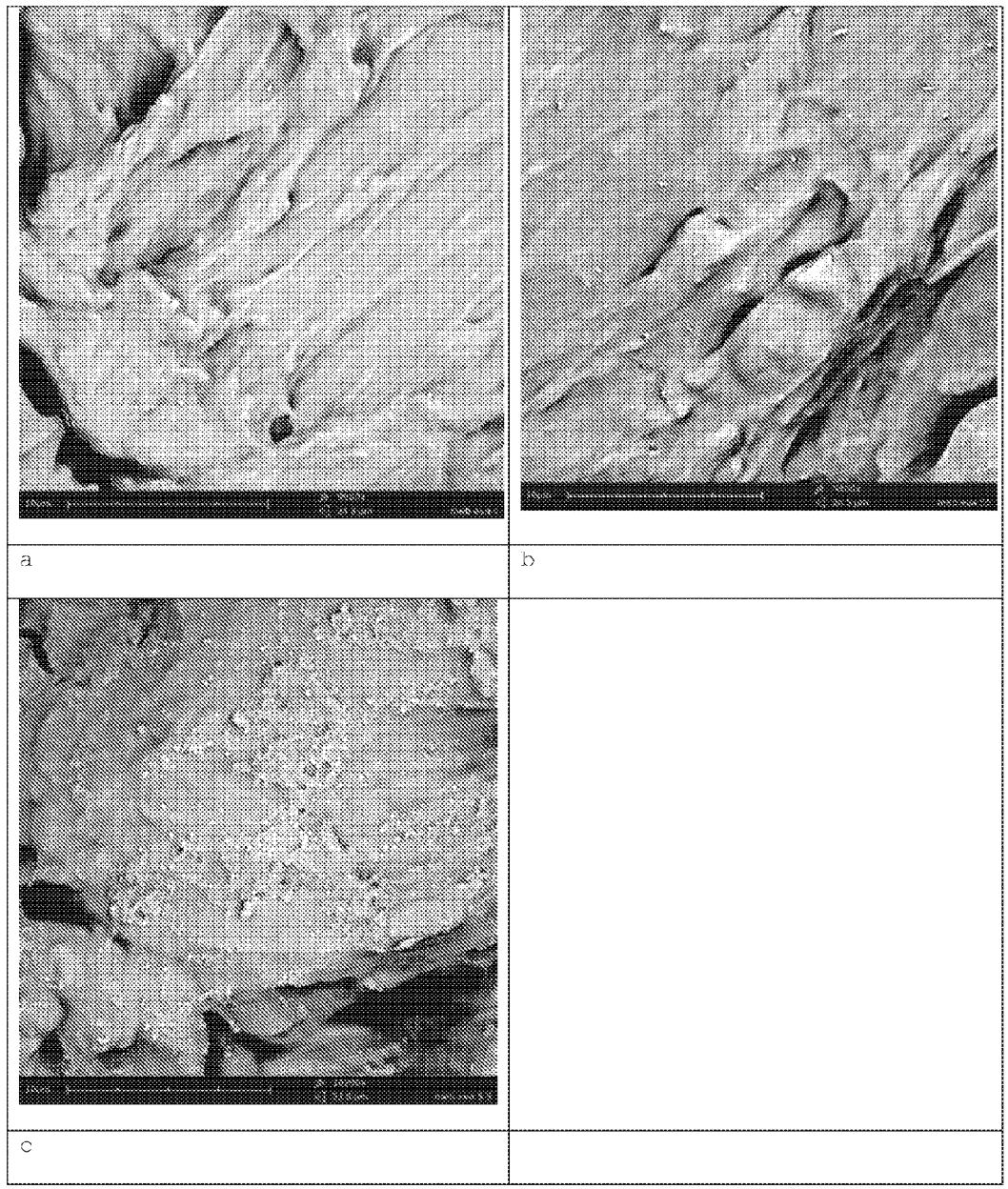
FIG. 7 shows the following SEM micrographs of an ethylene vinyl acetate (EVA) polymer some of which incorporate MNPs. (a) control specimen, no MNPs [10 $\mu$m, 9900×]; (b) CHX-HMP-0.5 MNPs [10 $\mu$m, 9800×]; (c) CHX-HMP-5 MNPs [10 $\mu$m, 10200×].

The EVA polymer surfaces coated with CHX-HMP-5 nanoparticles showed the same characteristic nanoparticle aggregates as observed on glass and the alginate wound dressing, although the coverage was typically somewhat less dense than that on the other substrates (FIG. 7). The EVA CHX-HMP-0.5 specimens showed a very low and short-lived release of soluble CHX. The CHX-HMP-5 specimens, however showed a prolonged release of CHX up to at least 80 days (FIG. 14), and this was comparable but slightly higher than the release seen from the glass specimens when normalised to surface area. These findings may find application in the developments of antimicrobial polymer-based medical devices such as venous and urinary catheters, and in periodic topical applications of antimicrobial coatings for removable polymer products such as sports and bruxism mouthguards.

Example 13—Titanium Functionalised with CHX-HMP-5

Example 14—Titanium Functionalised with CHX-HMP-0.5

Comparative Example 7—Titanium Exposed to Control 25 µM CHX Solution

Figure 8:
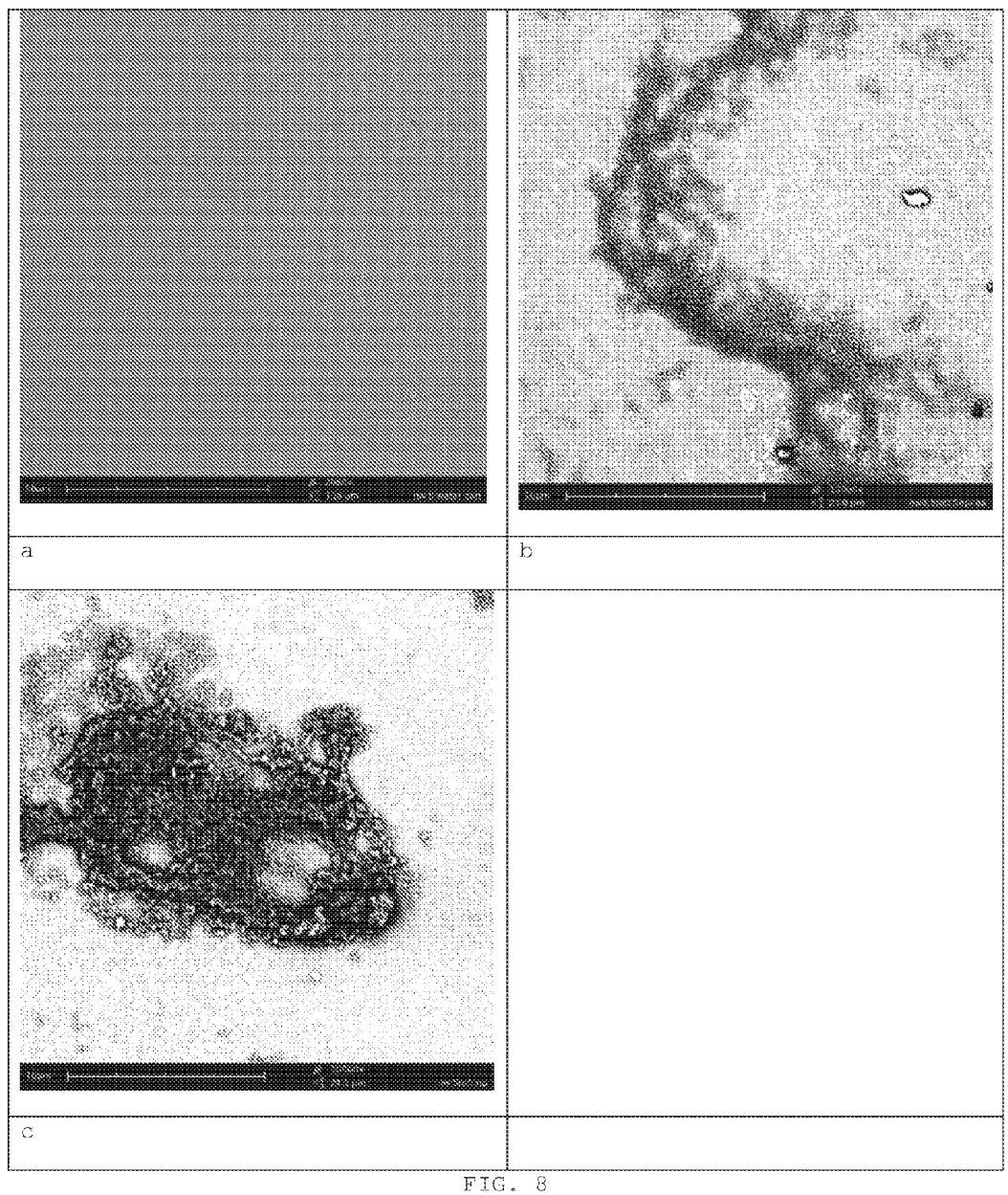
FIG. 8 shows the following SEM micrographs on titanium surfaces some of which have been treated with MNPs. (a) control specimen, no MNPs [50 $\mu$m, 2080×]; (b) CHX-HMP-0.5 MNPs [10 $\mu$m, 10000×]; (c) CHX-HMP-5 MNPs [10 $\mu$m, 10000×].

The titanium surfaces showed clear evidence of aggregations of CHX-HMP nanoparticles, as seen in FIG. 8. The CHX-HMP-5 functionalised specimens showed a continuous and sustained release of soluble CHX over the duration of the experiments; numerically this release was about double that seen from glass and polymer surfaces. The CHX-HMP-0.5 functionalised surfaces released little CHX and this release ceased after approximately 5 days. The CHX-HMP-5 nanoparticles might find application in the development, of antimicrobial coatings for dental and orthopaedic implants fabricated from titanium or titanium alloy, and offer the advantage over traditional antimicrobial coatings that the nanoparticles generate a discontinuous coating with plenty of titanium still exposed and available for colonisation by osteoblast cells.

Examples 15-18; Comparative Examples 8-10: Microbiology Studies

Microbiology: Bacterial Strains

Methicillin-resistant *Staphylococcus aureus* (MRSA; NCTC13142) was cultured in Mueller-Hinton media. *Pseudomonas aeruginosa* NCIMB 8626 (ATCC 9027) was cultured in nutrient broth (NB) or nutrient agar (NA). All cultures were incubated at 37° C. aerobically throughout the study.

Microbiology: Minimum Inhibitory Concentrations

The minimum inhibitory concentration (MIC) for the control aqueous 25 µM chlorhexidine and the CHX-HMP-5 colloid against planktonic bacteria was determined by serial doubling dilution (0-25 µM) in a total volume of 100 µL appropriate media in a 96 well microtitre plate (according to British Society for Antimicrobial Chemotherapy methodology for determining MIC). Cultures were incubated for 16 h at 37° C. in aerobic conditions, optical density (OD) readings were measured at 620 nm ($A_{620}$) using a standard microtitre plate reader (SpectroStar Nano; BMG Labtech).

Microbiology: Total Viable Counts

Samples were taken from wells of the microtitre plate and serially diluted ($10^{-1}$-$10^{-6}$) in phosphate buffered saline (PBS); 10 µl aliquots were enumerated using the total viable cell (TVC) counting method of Miles and Misra (see Hyg (Lond), vol. 38, pp. 732-749, 1936) with MH or NA as a non-selective medium. The numbers of recovered cells were calculated as cfu ml$^{-1}$.

Microbiology: Static Biofilm Model

Bacterial strains were initially grown for 16 h and these stationary phase cultures were harvested by centrifugation, and adjusted to $OD_{650}$=0.1. Biofilms were grown in 50 µL appropriate media at 37° C. for 48 h, aerobically then the media was removed and discarded. Loosely adherent bacteria were removed by washing the biofilms twice with 100 µl PBS. Chlorhexidine or chlorhexidine nanoparticles diluted in PBS were added to the biofilms using a doubling dilution as described above (0-25 µM). The plates were incubated for 2 h at 37° C.; to estimate biomass, unattached cells were gently aspirated and discarded, and adherent cells were washed twice with PBS and stained with crystal violet (0.25% w/v) for 10 min; following a further two washes with PBS, cell-bound crystal violet was re-solubilized with 7% acetic acid, and absorbance measured at 595 nm ($A_{595}$).

Microbiology: Biofilms on Nanofunctionalised EVA Polymer Specimens

Pre-cultures of MRSA and *P. aeruginosa* were grown initially for 16 h in appropriate media at 37° C., aerobically. Assays for growth on polymer pieces was determined by placing each cube into the well of a 24-well MTP and adding 1 ml of appropriate liquid media (enough to cover the polymer specimen). Polymer specimens were EVA polymer as specified in Table 3 which had been cleaned by 10 min ultrasonication in IMS followed by either no treatment (control), 30 s immersion in stirred CHX-HMP-5 followed by 10 s in deionised water (low NP) and 30 s immersion in stirred CHX-HMP-5 without a rinse (high NP). Each well was inoculated with 10 µl of either the MRSA or *P. aeruginosa* pre-cultures and then incubated for 24 h at 37° C. Polymer specimens were removed from the wells using sterile forceps and transferred to microcentrifuge tubes containing 1 ml PBS. The tubes were vortexes for 1 min to remove adherent bacteria, and cell suspension was serially diluted ($10^{-1}$-$10^{-6}$) and bacteria were enumerated using the Miles Misra method.

Table 6 shows the MIC for control and CHX-HMP media.

TABLE 6

| | Medium | MIC, total CHX conc (soluble CHX conc) |
|---|---|---|
| Example 15 | CHX-HMP-5 suspension | MRSA: 0.625 mM (3.12 µM); P.a.: 0.312 mM (1.56 µM) (minimum tested) |
| Comparative Example 8 | 25 µM CHX | MRSA: Not established (not efficacious) P.a.: (25 µM) |

Table 7 shows the effects of different media on static bacterial biofilms of MRSA and P. aeruginosa.

TABLE 7

| | Medium | Effect on biofilm |
|---|---|---|
| Example 16 | CHX-HMP-5 | MRSA: severe disruption P.a.: severe disruption |
| Comparative Example 9 | 25 µM CHX | MRSA: slight disruption P.a.: slight disruption |

Table 8 shows the antimicrobial effects of nanofunctionalised EVA polymer specimens.

TABLE 8

| | Specimen | Result |
|---|---|---|
| Example 17 | High NP CHX-HMP-5 on EVA | MRSA: No bacteria P.a.: No bacteria |
| Example 18 | Low NP CHX-HMP-5 on EVA | MRSA: No bacteria P.a.: High levels of bacteria, low turbidity liquid medium |
| Comparative Example 10 | Untreated EVA | MRSA: $5 \times 10^5$ cfu ml$^{-1}$ recovered P.a.: High levels of bacteria recovered, high turbidity liquid medium |

Figure 19:
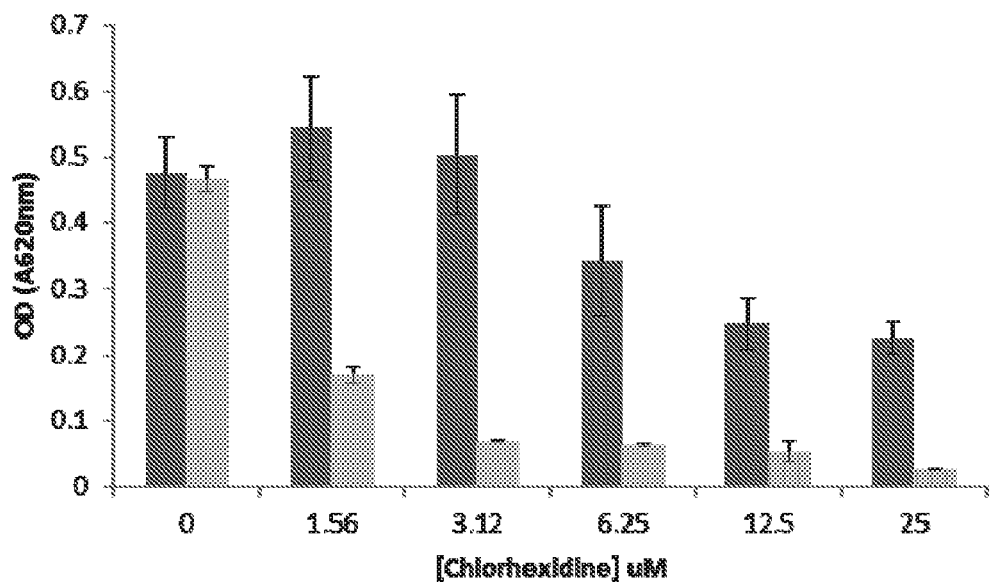
FIG. 19 shows Optical Density (OD) measurements at 620 nm of CHX and CHX-HMP-5 against MRSA. From these minimum inhibitory concentrations can be calculated. Dark grey bars: 25 μM CHX; light grey bars: CHX-HMP-5.
Figure 20:
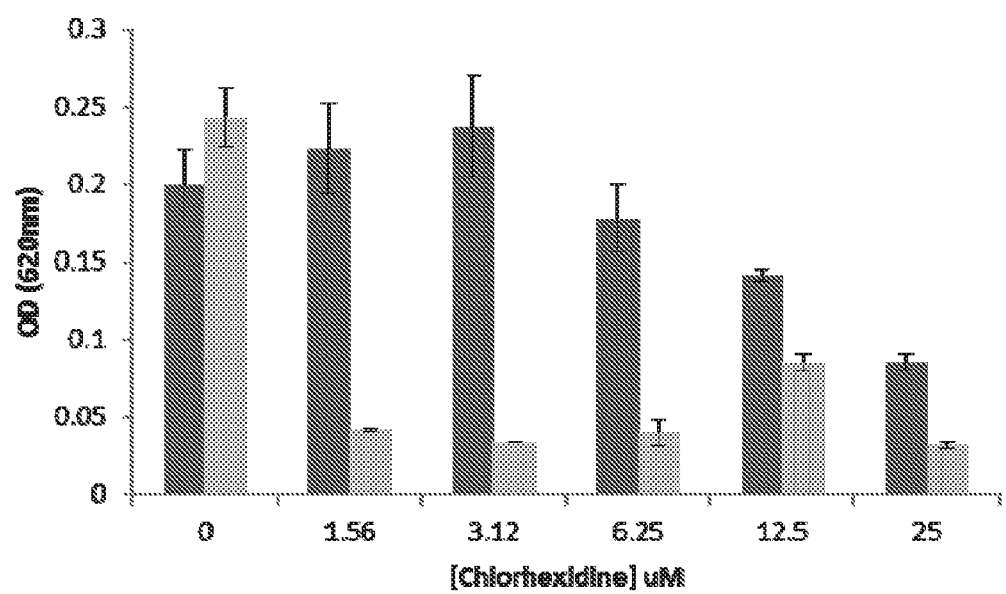
FIG. 20 shows Optical Density (OD) measurements at 620 nm of CHX and CHX-HMP-5 against P. aeruginosa. From these minimum inhibitory concentrations can be calculated. Dark grey bars: 25 μM CHX; light grey bars: CHX-HMP-5.

The MIC for MRSA for CHX-HMP-5 colloidal suspension was found to be an 8× dilution of the colloid, which corresponds to a total (soluble and bound) CHX concentration of 0.625 mM and a soluble CHX concentration of 3.12 µM. The MIC for MRSA could not be established for 25 µM chlorhexidine indicating that this solution was not efficacious against MRSA (FIG. 19). For P. aeruginosa the MIC for CHX-HMP-5 was found to be a 16× dilution of the colloid, which was the minimum concentration tested; this corresponds to a total CHX concentration of 0.312 mM and a soluble CHX concentration of 1.56 µM. The MIC for the 25 µM chlorhexidine concentration was the undiluted solution, i.e. 25 µM, indicating that P. aeruginosa was more susceptible to the nanoparticles than MRSA (FIG. 20). TVCs confirmed the MIC data, with $1.5 \times 10^{12}$ cfu ml$^{-1}$ recovered for the MRSA untreated control and no bacteria recovered from samples grown with 8× and 4× dilutions of the CHX-HMP-5 colloid suggesting that the MIC was also bactericidal. Similarly, for P. aeruginosa no bacteria could be recovered from samples grown at 16× and 8× dilution of the CHX-HMP-5 colloid, compared to $1.34 \times 10^9$ cfu ml$^{-1}$ recovered for the untreated control.

Figure 21:
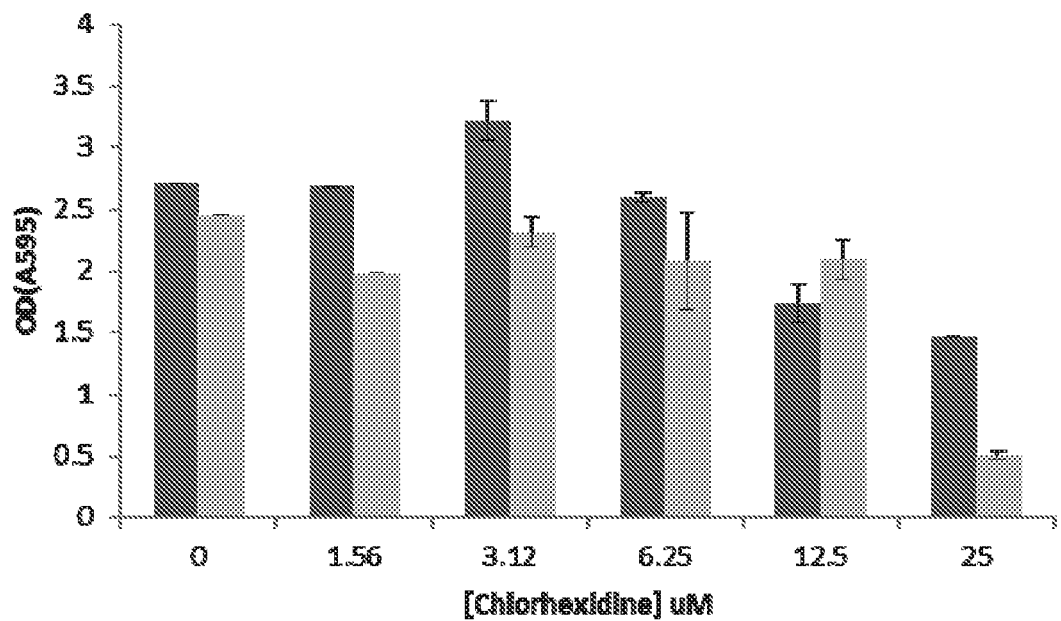
FIG. 21 shows optical Density (OD) measurements at 595 nm following treatment with CHX or CHX-HMP-5 against MRSA. From these biofilm inhibition can be gauged. Dark grey bars: 25 μM CHX; light grey bars: CHX-HMP-5.
Figure 22:
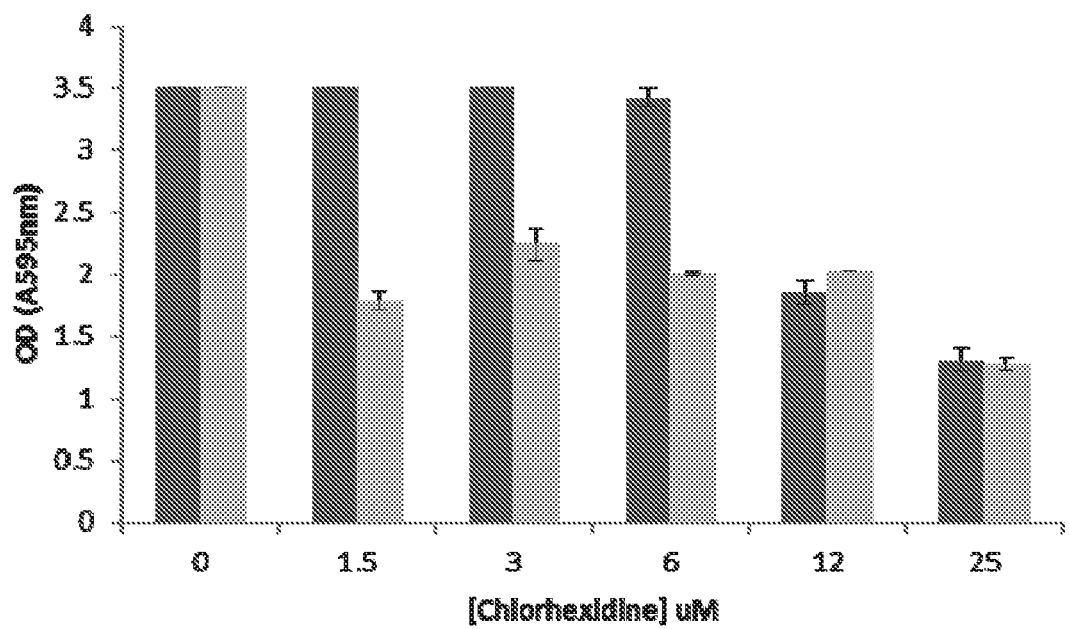
FIG. 22 shows optical density (OD) measurements at 595 nm following treatment with CHX or CHX-HMP-5 against P. aeruginosa. From these biofilm inhibition can be gauged. Dark grey bars: 25 μM CHX; light grey bars: CHX-HMP-5.

Biofilms of MRSA were disrupted by the CHX-HMP-5 colloid and to a lesser extent by the aqueous 25 µM chlorhexidine (FIG. 21). The CHX-HMP-5 colloid also disrupted biofilms of P. aeruginosa (FIG. 22) more effectively than aqueous 25 µM chlorhexidine at dilutions of between 16× and 4× at 2× and undiluted levels 25 µM chlorhexidine and the nanoparticles were equally effective. Regarding biofilm growth on nanofunctionalised EVA polymer, for the control polymer P. aeruginosa bacterial cells recovered from the specimens were too numerous to count at all of the dilutions used; MRSA was recovered at $5 \times 10^5$ cfu ml$^{-1}$. For the polymer pieces coated with a low concentration of nanoparticles bacterial cells were too numerous to count at all dilutions for P. aeruginosa but no cells were recoverable for MRSA. It should be noted that for P. aeruginosa the surrounding liquid media was less turbid than the control (indicating less growth) despite high numbers of bacteria being recovered and that for MRSA the surrounding media was clear, indicating no growth. For the polymer pieces coated with a high concentration of nanoparticles no bacteria were recoverable for either MRSA or P. aeruginosa and the surrounding media was clear in both instances.

The microbiology experiments indicated that the CHX-HMP-5 colloid was efficacious against planktonically grown MRSA and P. aeruginosa in vitro and that this effect was not due to the residual 25 µM soluble CHX present in the solution bathing the colloid. Furthermore, the biofilm studies indicated that the CHX-HMP-5 colloid was efficacious against biofilms of MRSA and P. aeruginosa in vitro. Furthermore, the EVA polymer specimens coated with CHX-HMP-5 nanoparticles exhibited efficacy against biofilms of MRSA and P. aeruginosa.

Examples 19-24; Comparative Example 11: Glass Ionomer Cements Substituted with CHX-HMP NPs Synthesis and Preparation of CHX-HMP Nanoparticles Aqueous stock solutions of chlorhexidine digluconate and sodium hexametaphosphate (both Sigma Aldrich) were mixed in deionised water such that the final concentration was 4 mM CHX and 5 mM. The resulting colloidal suspension was mixed thoroughly and then centrifuged at 21000 g for 60 min. The supernatant was removed and discarded and the NP pellet dried for at least 48 h at 40° C. The pellet was then removed from the centrifuge tubes and ground to a fine white powder using a mortar and pestle. This powder was added to the GIC by substitution for the glass powder.

Nanofunctionalised Glass Ionomer Cements

A commercially available GIC (Diamond Carve™, Kemdent, Purton, UK) was used as the starting material. Cylindrical GIC specimens with nominal dimensions of 6 mm diameter and 3 mm height were formed by mixing the GIC according to the manufacturers' instructions and packing into Perspex molds coated with a thin layer of petroleum jelly to aid removal. The mixing was carried out by individuals with extensive experience of GIC preparation. The precise dimensions of each specimen were measured using callipers and recorded. The NP powder was mixed with aliquots of the GIC glass powder at substitutions of 0, 1, 2, 5, 10, 20 and 30 wt %. Ten specimens of each substitution were created giving a total of 70 specimens. They were removed from the mold within 60 minutes and placed in individual small, sealed plastic vessels that contained wet tissue paper not in direct contact with the specimen, to achieve an atmosphere of 100% humidity but prevent the specimen being in contact with liquid water which could result in dissolution during the critical early phases of setting. These were stored at 37° C. for 7 days.

After this time the specimens were divided into two sets of 5 specimens each. One set of each substitution was set aside for tensile strength and morphology testing and the other set was used to investigate the chlorhexidine and fluoride leaching from the cement.

For the investigations of chlorhexidine and fluoride release, each specimen was immersed in 1 mL artificial saliva in individually labelled vials at 37° C. The artificial saliva was composed of $CaCl_2 \cdot 2H_2O$ 0.103 $gL^{-1}$, $MgCl_2$ 0.019 $gL^{-1}$, $KH_2PO_4$ 0.544 $gL^{-1}$, $C_8H_{18}N_2O_4S$ (HEPES buffer acidic form) 4.77 $gL^{-1}$, KCl 2.24 $gL^{-1}$, 1.80 mL 1M HCl, KOH titrated to obtain a pH of 6.8. Specimens were periodically removed and placed in duplicate tubes containing fresh artificial saliva such that the artificial saliva the specimen had been incubated in could be sampled for chlorhexidine and fluoride concentrations. A pilot study was conducted to establish the saturation limit of fluoride concentration within the vessels to ensure that the sampling periods were selected appropriately and erroneous readings owing to saturation of the eluent by a fluoride salt were not obtained by leaving too large a gap between readings. Using the findings from this pilot study, the sampling occurred at hourly intervals during the first day, followed by intervals of 4 hours, then daily and then weekly. Controls containing only artificial saliva without a GIC specimen were sampled in the same way.

Chlorhexidine Measurements

Chlorhexidine concentration in the artificial saliva was measured using ultraviolet (UV) spectrophotometry. The 1 mL artificial saliva was placed into a semi-micro cuvette transparent under UV wavelengths and absorption was measured at 255 nm using a spectrophotometer. The reading was converted to chlorhexidine concentration with reference to calibration standards at 5, 10, 20, 30, 40, 50 $\mu mol \cdot l^{-1}$ chlorhexidine which were measured at the beginning and end of each measurement cycle. The concentration was converted to moles of chlorhexidine released per unit surface area of the GIC specimen with reference to the individual dimension measurements for each specimen.

Fluoride Measurements

Fluoride concentration in the artificial saliva was measured using an ion selective electrode by mixing 0.5 mL artificial saliva with 0.5 mL TISAB solution. The data output was converted to mg/L fluoride ion with reference to calibration standards of 0.1, 0.5, 1, 2 and 5 mg/L $F^-$, also diluted with equal quantities of TISAB.

Tensile Strength Measurements

Indirect tensile strength was measured by applying a compressive diametric force to the cylindrical specimen until fracture occurred, recording the load at fracture and using this to calculate tensile strength.

Statistical Analysis

Cumulative CHX and fluoride release at time points of 1 h, 24 h, 6 days, 15 days and 33 days, and indirect tensile strength, were compared using one-way ANOVAs with a Tukey honestly significant difference post-hoc test.

Morphology and Structure

Specimens which had been tested for tensile strength were coated with a thin layer of gold-palladium (SC7620, Emitech, Taiwan) and examined in a scanning electron microscope (Phenom, Eindhoven, Netherlands). Images were obtained at nominal magnifications of 400, 1000 and 5000×.

Table 9 shows properties of the substituted and unsubstituted GICs.

TABLE 9

|  | NP Content (wt %) | Handling Properties | CHX Release Period | F Release Period | Diametral Tensile Strength (MPa) (standard deviation in parentheses) |
|---|---|---|---|---|---|
| Example 19 | 1 | Good | >33 days | >33 days | 14.3 (4.9) |
| Example 20 | 2 | Good | >33 days | >33 days | 15.7 (4.3) |
| Example 21 | 5 | Good | >33 days | >33 days | 15.5 (1.1) |
| Example 22 | 10 | Good | >33 days | >33 days | 11.5 (2.8) |
| Example 23 | 20 | Good | >33 days | >33 days | 9.4 (2.6) |
| Example 24 | 30 | Poor (discarded) | N/A | N/A | N/A |
| Comparative Example 11 | 0 | Good | >33 days | >33 days | 14.1 (3.7) |

Table 10 shows cumulative CHX release. Within each timepoint, letters indicate statistically homogeneous groups, so figures with different letters are statistically significantly different to a 95% confidence level at that time.

TABLE 10

| | Cumulative CHX release [nmol · mm-2] (standard deviation in parentheses) | | | | |
|---|---|---|---|---|---|
| | 1 h | 24 h | 8 days | 15 days | 33 days |
| Example 19 | 0.16 (0.08)a,b | 0.20 (0.09)a,b | 0.48 (0.15)a,b | 0.56 (0.16)a,b | 0.65 (0.17)a,b |
| Example 20 | 0.66 (0.18)b | 0.70 (0.19)b | 1.04 (0.21)b | 1.17 (0.22)b | 1.30 (0.24)b |
| Example 21 | 1.30 (0.24)c | 1.39 (0.25)c | 2.03 (0.34)c | 2.30 (0.36)c | 2.51 (0.38)c |
| Example 22 | 2.52 (0.38)d | 2.65 (0.40)d | 3.40 (0.43)d | 3.73 (0.44)d | 4.01 (0.45)d |
| Example 23 | 4.02 (0.48)e | 4.20 (0.50)e | 5.09 (0.55)e | 5.46 (0.59)e | 5.94 (0.67)e |
| Comparative Example 11 | 0.01 (0.003)a | 0.01 (0.02)a | 0.11 (0.06)a | 0.12 (0.07)a | 0.16 (0.08)a |

Table 11 shows cumulative fluoride release. Within each timepoint, letters indicate statistically homogeneous groups, so figures with different letters are statistically significantly different to a 95% confidence level at that time.

TABLE 11

| | Cumulative fluoride release [ng · mm-2] (standard deviation in parentheses) | | | | |
|---|---|---|---|---|---|
| | 1 h | 24 h | 8 days | 15 days | 31 days |
| Example 19 | 2.61 (1.11)b | 18.59 (3.12)a,b | 70.72 (8.40)a | 106.9 (14.1)a | 148.1 (16.6)a |
| Example 20 | 1.68 (0.73)b | 17.10 (2.33)b | 64.30 (7.68)a | 101.1 (12.2)a | 147.5 (15.7)a |
| Example 21 | 1.74 (0.70)b | 19.31 (4.32)a,b | 82.67 (7.49)a | 124.2 (9.2)a | 181.4 (14.0)a,b |
| Example 22 | 1.83 (0.96)b | 18.73 (9.50)a,b | 81.73 (30.22)a | 122.8 (39.3)a | 184.4 (49.8)a,b |

TABLE 11-continued

| | Cumulative fluoride release [ng · mm-2] (standard deviation in parentheses) | | | | |
|---|---|---|---|---|---|
| | 1 h | 24 h | 8 days | 15 days | 31 days |
| Example 23 | 2.09 (0.34)b | 23.74 (5.89)a,b | 81.73 (13.15)a | 134.6 (19.2)a | 204.4 (23.4)b |
| Comparative Example 11 | 7.38 (1.69)a | 27.65 (0.85)a | 85.82 (5.68)a | 119.9 (11.0)a | 154.5 (14.3)a,b |

Overview

GIC specimens with substitutions of 1, 2, 5, 10 and 20 wt % CHX-HMP nanoparticles for glass powder were successfully created and compared with unmodified GICs (0 wt % substitution). Those with 30 wt % substitution of CHX-HMP nanoparticles were more crumbly and difficult to handle and were discarded.

Chlorhexidine Release

Figure 16:
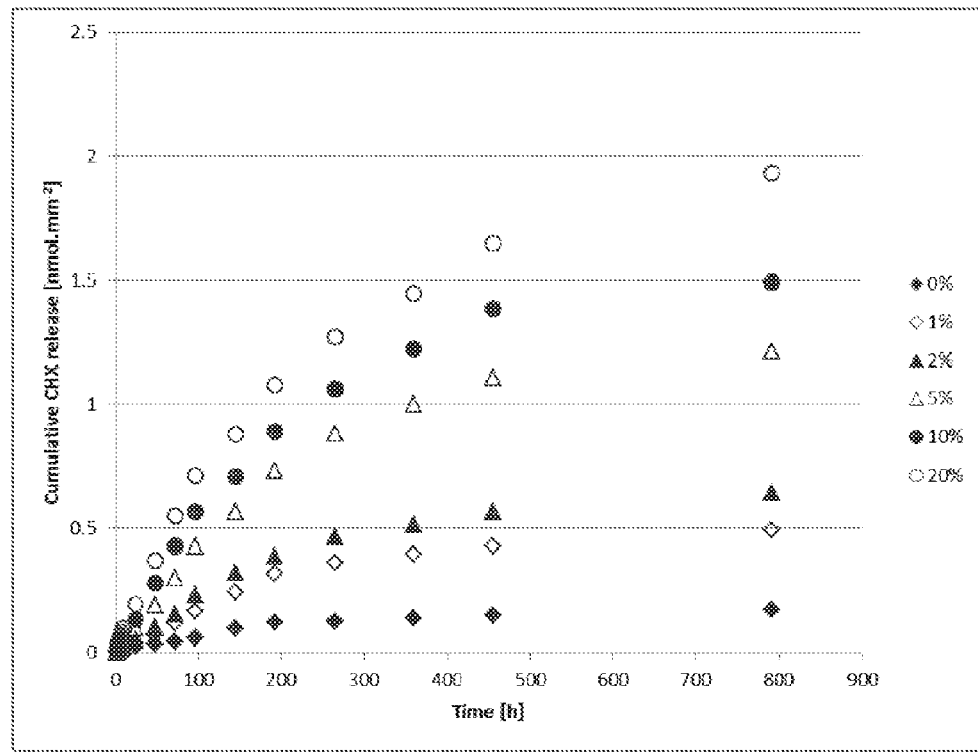
FIG. 16 shows cumulative CHX release profiles from glass ionomer cement (GIC) specimens with varying levels of treatment with CHX-HMP MNPs.

CHX release over 791 h (33 days) normalised to surface area can be seen in FIG. 16. CHX release persisted for the duration of the study and had not reached a clear plateau at the final measurement timepoint. A dose-response was evident in that specimens with a higher substitution of CHX-NPs exhibited a larger CHX release, although the relationship was not directly proportional.

Cumulative CHX release at 1 and 24 h and 8, 15 and 33 days for the 6 specimen groups and the outcome of the statistical analyses are shown in Table 10. The outcome was the same for each time point in that 0 wt % and 1 wt % were not statistically significantly different from one another, and 1 wt % and 2 wt. % were not statistically significantly different from one another, but all other pairings were significantly different indicating a clear increase in chlorhexidine release correlated with an increase in nanoparticle substitution at all measured times.

Fluoride Release

Figure 17:
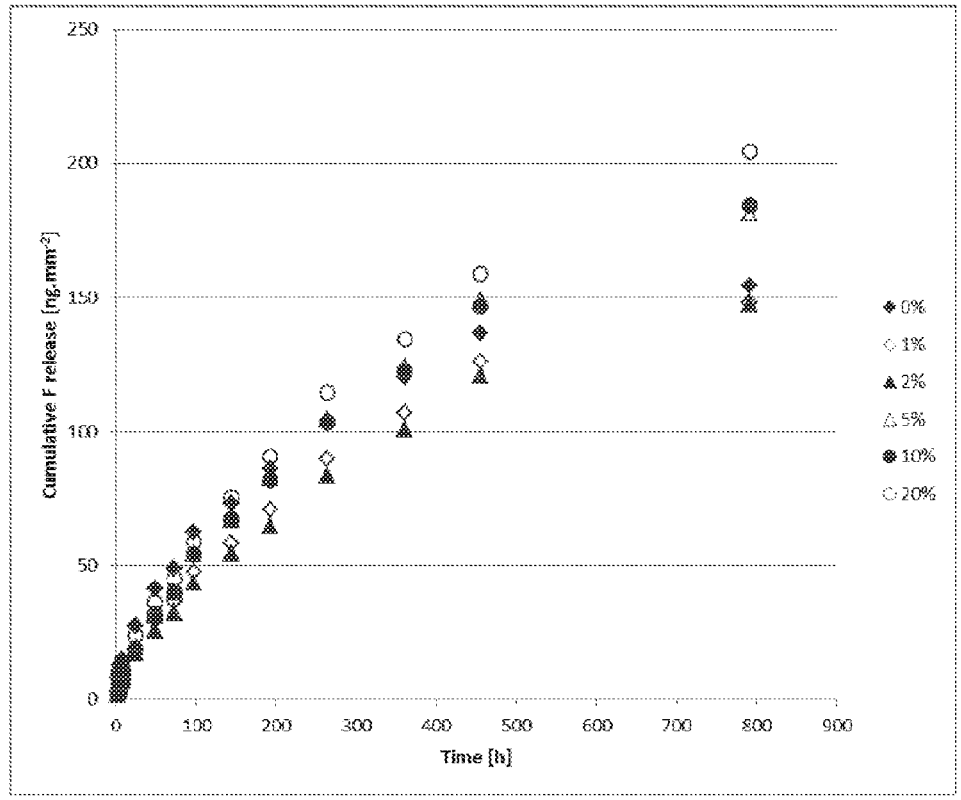
FIG. 17 shows cumulative fluoride release from GIC specimens with varying levels of treatment with CHX-HMP MNPs.

Fluoride release over 791 h (33 days) normalised to surface area can be seen in FIG. 17. All of the GIC specimens released fluoride continually over the duration of the experiment. The initial release rate was the most rapid and this gradually slowed over the experimental period.

Cumulative fluoride release at 1 and 24 h and 8, 15 and 33 days for the 6 specimen groups and the outcome of the statistical analysis are shown in Table 11. At 1 h, unmodified GIC released significantly more fluoride than substituted fluoride but there were no statistically significant differences between the different substitutions. At later times there were few differences and fluoride release was very similar for all GIC specimens and did not vary as a function of nanopartjcie substitution.

Tensile Strength

Diametral tensile strength of the 6 specimen groups are shown in Table 3. The ANOVA gave a p value of 0.054 indicating that, although there was a numerical trend towards lower tensile strength for 10 and 20 wt % substitution cements, there was no statistically significant difference between these values and those of the other GICs.

Morphology and Structure

Figure 18:
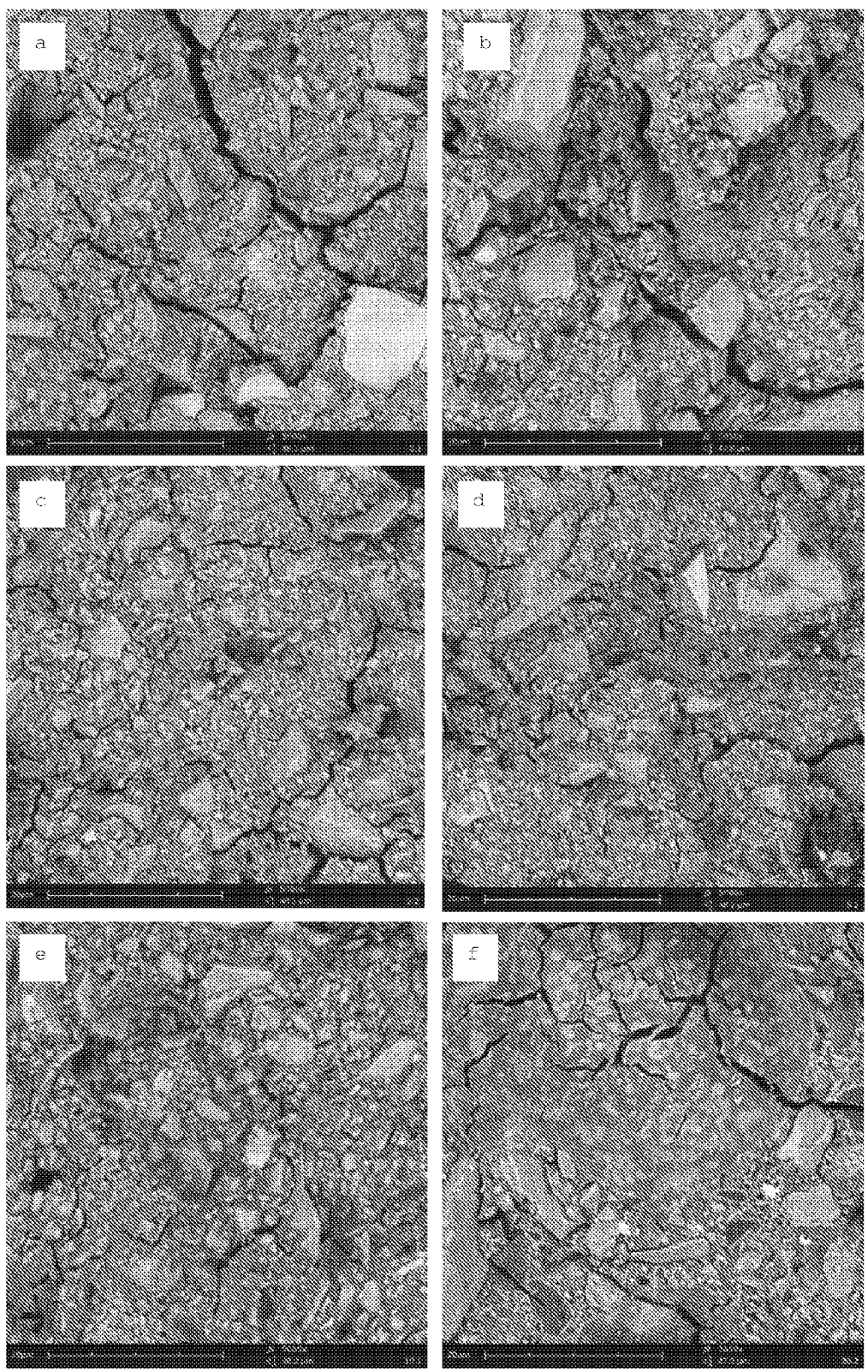
FIG. 18 shows the following SEM micrographs showing fracture surfaces of GIC specimens. (a) unmodified GIC [20 μm, 5000×]; (b) 1 wt % MNPs [20 μm, 5050×]; (c) 2 wt % MNPs [20 μm, 5000×]; (d) 5 wt % MNPs [20 μm, 5000×]; (e) 10 wt % MNPs [20 μm, 5000×]; (f) 20 wt % MNPs [20 μm, 5050×].

Scanning electron micrographs of representative GIC specimens are shown in FIG. 18. The appearance of the GIC specimens with different substitutions of nanoparticles were indistinguishable, with the glass filler particles and surrounding matrix clearly visible. Only the 20 wt % nanoparticle substitution exhibited a slightly different appearance (FIG. 18f), with evidence of more smaller particles or nanoparticle aggregates.

Conclusion

By adding CHX-HMP nanoparticles to a commercial GIC, it has proven possible to create a material which releases CHX for an extended period in a dose dependent manner. Since CHX is efficacious against a wide range of bacteria and yeasts, this confers antimicrobial and anticaries properties on these novel nanofunctionalised dental filling materials. Substitutions up to 5 wt % appeared to have no significant deleterious effect on the tensile strength (Table 9) of the cements. Higher substitutions may lead to a reduction in tensile strength although this was not statistically significant; at 20 wt % it was possible to see some different morphologies within the cement structure (FIG. 18) indicating the presence of nanoparticles and nanoparticle aggregates. These higher substitutions could lead to a reduction in strength since they cannot be presumed to interact with the polyacid in the same way as the glass filler particles. The nanofunctionalised GICs showed the same fluoride release profile as the unmodified cements.

The use of the CHX-HMP nanoparticles described herein, as opposed to other approaches such as using ground up CHX diacetate or an aqueous solution of CHX digluconate, offers the advantage that the CHX release is sustained for considerably longer with the GICs (FIG. 16). Composite resins supplemented with pulverised CHX diacetate showed CHX release which reached a plateau after around 7 days (Dent Plater, vol. 28, pp. 573-583, 2012), compared to a continued release of at least 33 days seen here.

GICs supplemented with CHX diacetate powder or CHX digluconate solution have been reported (J Esthet Rector Dent, vol. 20, pp. 29-44; discussion 45, 2008), and these inhibited the growth of several oral microorganisms. CHX release from these GICs was not measured directly. Most specimens showed no antimicrobial behaviour after 60-90 days. The peak of efficacy in these known GICs was the first 24 h for all GIC specimens, suggesting that most CHX is released during this initial period. The more extended CHX release observed in the GICs incorporating MNPs of the present proposals lead to a more prolonged antimicrobial efficacy.

Example 25—Microbiology on EVA Samples Functionalised with CHX Nanoparticles

EVA specimens were functionalised by 30 s immersion in a colloidal suspension of CHX-HMP-5 in water followed by 10 s immersion in deionised water ("low concentration") or without subsequent immersion in deionised water ("high concentration"). These samples were then exposed to cultures of MRSA bacteria. They were then immersed in 1 mL, growth medium and incubated for 18 h. According to the release experiments in this time the EVA specimen should release around 6 µM per m$^2$ material. Surface area of the specimen was 0.000182 m$^2$ so the expected total release should be 1.1 nM CHX into 1 mL giving a resultant concentration of 1.1 µM CHX.

These specimens, which resulted in a CHX concentration of around 1.1 µM, had no recoverable MRSA. However, similar treatment using a 25 µM CHX solution (as opposed to CHX-HMP-5 suspension) was not efficacious against MRSA. These results indicate that the nanoparticles were efficacious against MRSA and that the nanoparticles themselves may exhibit some additional antibacterial effect over and above that attributable to the released CHX. This may be due to a localised much higher concentration of CHX which is highest close to the surface of the material; and/or the nanoparticles having inherent antimicrobial activity.

Example 26—Microbiology on Titanium Samples Functionalised with CHX Nanoparticles Titanium specimens functionalised with CHX-HMP-5 were also exposed to cultures of Streptococcus gordonii bacteria. The samples were immersed in 2 mL growth medium and incubated for a maximum of 48 h. According to the release experiments this should result in a release of around 7 μM per m². The surface area of specimen was 0.00024 m² so the expected release should be 1.7 nM CHX into 2 mL giving a resultant concentration of 0.8 μM CHX.

The nanoparticle-functionalised titanium surface eliminated the bacteria in the sample.

The MIC for S. mutans (a similar gram positive Streptococcus bacteria to S. gordonii also implicated in dental caries) has been reported as 0.125% CHX digluconate by mass which corresponds to around 1.4 mM, i.e. four orders of magnitude higher than the CHX concentration effected by the present specimens.

These results are suggestive that the nanoparticles themselves exhibit some inherent antimicrobial effect over and above the release of soluble CHX into the bulk solution.

Example 27—CHX-HMP MNP Properties

Provided herein is direct evidence regarding the composition and stoichiometry and size and aggregation properties of CHX-HMP MNPs.

Figure 23:
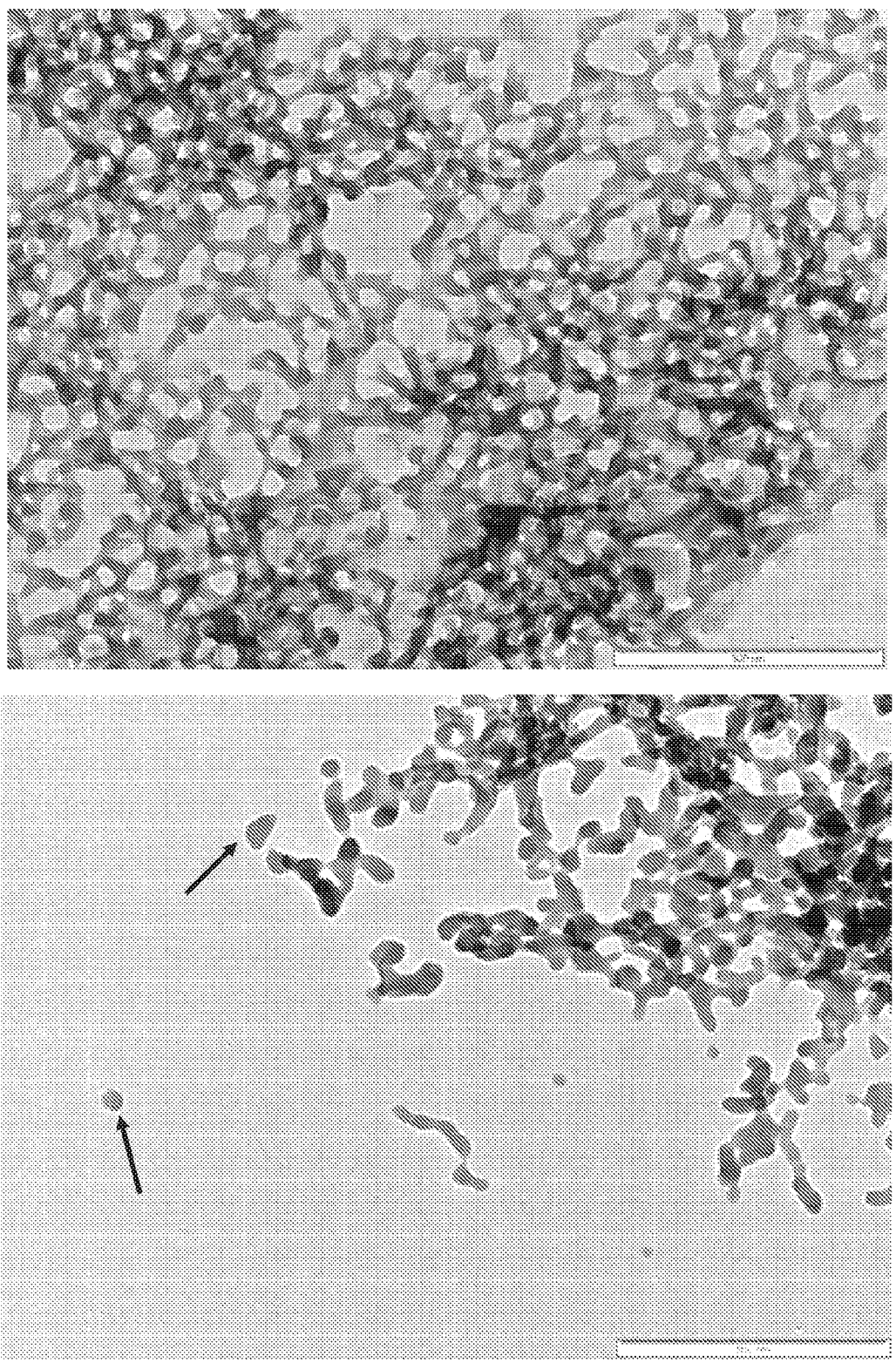
FIG. 23 shows TEM micrographs of (upper) CHX-HMP-0.5 and (lower) CHX-HMP-5 NPs. Examples of individual NPs are indicated by arrows. Scale bars=500 nm.

TEM analysis of the MNPs, specifically the CHX-HMP-5 and CHX-HMP-0.5 compositions, has been carried out (FIG. 23). CHX-HMP-5 and CHX-HMP-0.5 NPs were deposited on carbon-coated copper grids (Agar Scientific Ltd., Essex, UK) and subjected to TEM and EDX (Jeol 120 kv 1200 Mk2; Jeol, Tokyo, Japan). TEM grids were immersed in NP suspensions for 2 s, rinsed in deionised water for 2 s and allowed to dry in air.

The MNPs were often found in aggregates of widely ranging size. FIG. 23 shows an example of a CHX-HMP-0.5 sample on the left and a CHX-HMP-5 sample on the right. The image of the higher concentration sample shows that MNPs can be seen at the periphery of an aggregate (top right of the image), with good visibility of individual nanoparticles. Two examples of separate, individual nanoparticles are indicated by arrows. TEM suggests that the MNPs are often fused together, and not just held electrostatically (see especially the image for the lower concentration sample). Some very small aggregates were also observed.

EDX was carried out CHX-HMP MNPs on TEM grids to investigate the composition of the MNPs Both Cl (from CHX) and P (from HMP) were observed in the spectra, confirming that the MNPs are composed of CHX and HMP. Signals from Cu and Au are attributed to the TEM grid on which the MNPs were deposited.

Figure 24:
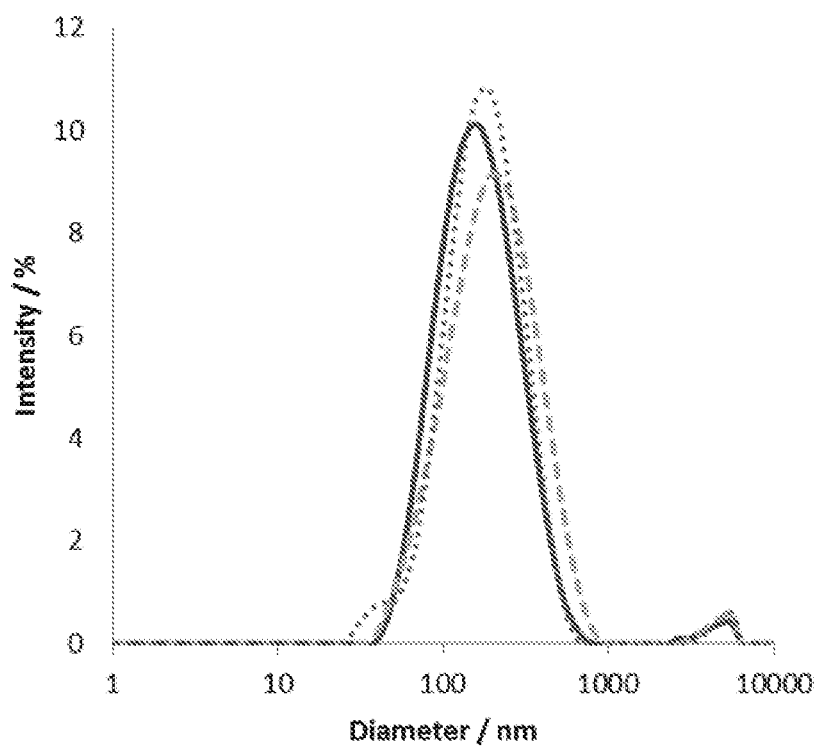
FIG. 24 shows DLS data showing size distributions of (upper) CHX-HMP-5, and (lower) CHX-HMP-0.5. The three data sets indicate measurements made in triplicate at each concentration.
Figure 24:
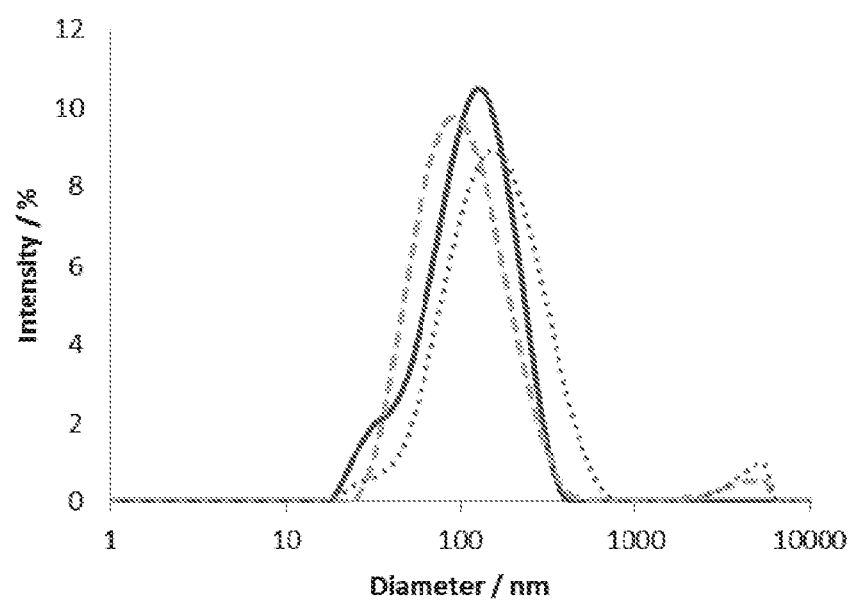
Figure 25:
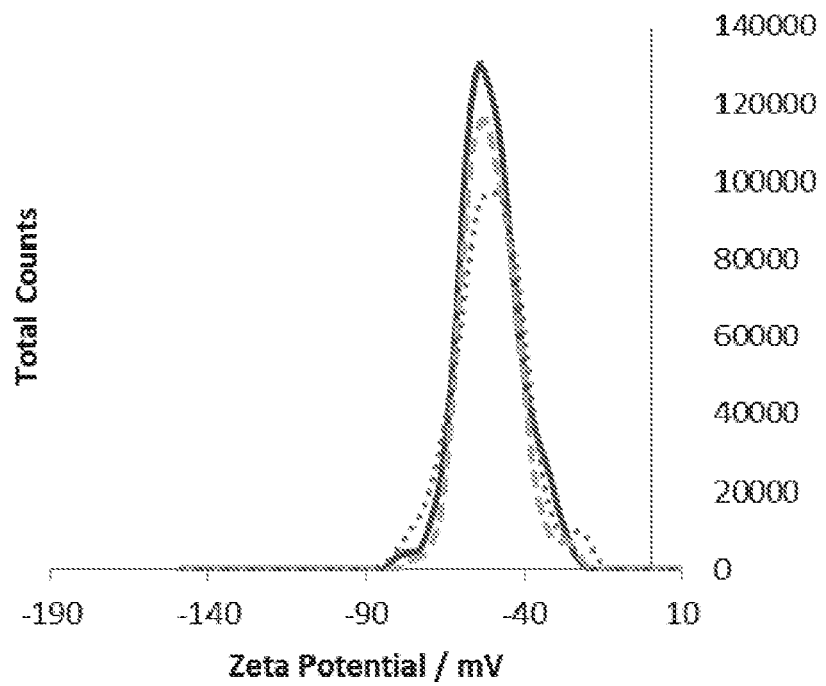
FIG. 25 shows zeta potential data showing the charge distribution of (upper) CHX-HMP-5, and (lower) CHX-HMP-0.5 NPs. The three data sets indicate measurements made in triplicate for each concentration.
Figure 25:
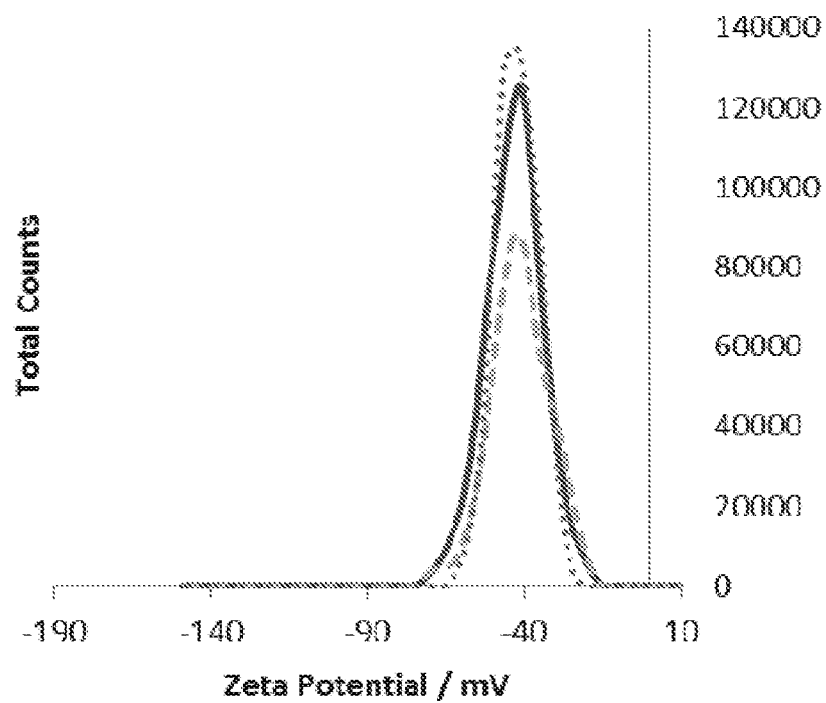

Dynamic light scattering (DLS) and zeta potential measurements (Zetasizer NanoZS; Malvern Instruments Ltd, Malvern, UK) have been conducted (FIG. 24 and FIG. 25, respectively). CHX-HMP-5 suspensions contained some sedimenting aggregates, so the specimen was allowed to settle before the supernatant was analysed. Each numerical value reported is the average of the 3 measurements represented graphically; each measurement was carried out on a different nanoparticle suspension. The particle sizes measured using DLS were different for CHX-HMP-5 and CHX-HMP-0.5, giving average values of 202 and 140 nm, respectively. The values obtained by DLS were slightly larger than that revealed by TEM (TEM analysis suggested values of approximately 40-80 nm), which is thought to be a result of aggregation observed by TEM (discussed above). This is supported by the observation that the particles typically formed larger aggregates in the higher concentration suspension. Zeta potential measurements revealed that both concentrations of MNP5 were negatively charged; CHX-HMP-5 had a larger net charge than CHX-HMP-0.5 (−50.8 and −42.2 mV, respectively).

Elemental analysis of the CHX-HMP-5 precipitate indicated that the nanoparticles are composed of a ratio of 3 ions of CHX to 1 ion of HMP.

Examples 28-29 and Comparative Examples 12-13—Composite Materials: Wound Dressing Films Films of the natural polysaccharides CMC (comparative example 12) and alginate (comparative example 13) have been created. Into equivalent films, CHX-HMP-5 nanoparticles have been incorporated at different doses (examples 28-29). These films show promise for use in novel antimicrobial wound dressings.

A 5 wt % aqueous solution of alginate was made up by adding dry alginate (Protanal LF 10/60 FT, FMC Biopolymers) to a rapidly stirring aqueous suspension of chlorhexidine hexametaphosphate nanoparticles equivalent to 6 wt. %, 3 wt % or 0 wt %. These solutions were poured into petri dishes (Φ=90 mm) and the water allowed to evaporate at room temperature for 3 days. $CaCl_2$ (30 mL, 2 wt % aq.) was added to the petri dishes and cross-linking allowed to occur for 25 min. The cross-linked alginate films were then removed from the petri dishes, washed with distilled water and air dried on parafilm.

A 5 wt % aqueous solution of carboxymethyl cellulose (CMC) was made up by adding dry CMC (three types: $M_w$=90,000, 250,000 and 700,000 with 0.7, 0.7 & 0.9 CM groups per anhydroglucose unit respectively) to a rapidly stirring aqueous suspension of chlorhexidine hexametaphosphate nanoparticles equivalent to 6 wt %, 3 wt % or 0 wt %. These solutions were poured into petri dishes (Φ=90 mm) and the water allowed to evaporate at room temperature for 4 days. 15 mL ethanol was added to cover each film and left to evaporate at room temperature. A second cover of 15 mL ethanol was added to the petri dishes which allowed the films to be removed. They were subsequently placed on parafilm and air dried.

3.32 mm² (alginate) or 5.00 mm² (CMC) sections of films were placed in semi-micro cuvettes, covered with water (2.2 mL) and the cuvettes sealed with lids and parafilm. The cuvettes were agitated by an orbital shaker (150 rpm), and the absorbance (255 nm) was measured once per 24 h and compared with that of chlorhexidine digluconate standards according to standard protocols. CHX-HMP NPs were shown to survive the cross-linking process within the alginate films, confirmed by FT-IR by the presence of a peak at 1492 cm$^{-1}$ and a shoulder at 1530 cm$^{-1}$ corresponding to the two main peaks in the CHX-HMP spectrum.

Figure 26:
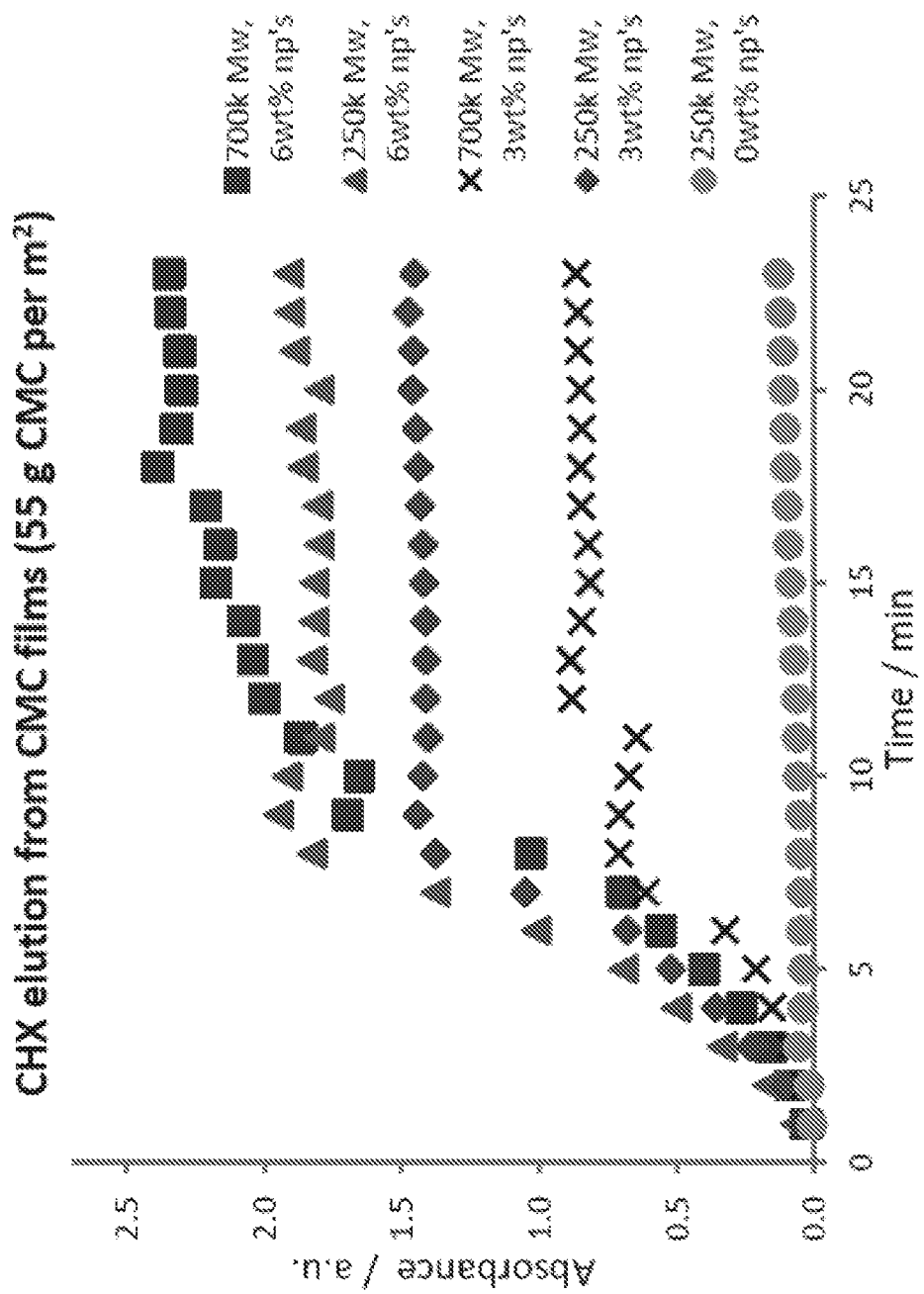
FIG. 26 shows CHX elution profiles from CMC films (55 g CMC per m$^2$) containing particular amounts of CHX-HMP-5 NPs. Squares indicate a CMC Mw of 700 kDa and 6 wt % NPs; triangles indicate a CMC Mw of 250 kDa and 6 wt % NPs; crosses indicate a CMC Mw of 700 kDa and 3 wt % MNPs; diamonds indicate a CMC Mw of 250 kDa and 3 wt % NPs; circles indicate a CMC Mw of 250 kDa and 0 wt % NPs.

CMC was found to dissolve rapidly on immersion in water, disintegrating and releasing all of the CHX over a period of approximately 10 minutes. CHX release reached completion within minutes and was dose dependent, with the higher wt % MNP-containing films showing a longer time to complete release (FIG. 26).

Figure 27:
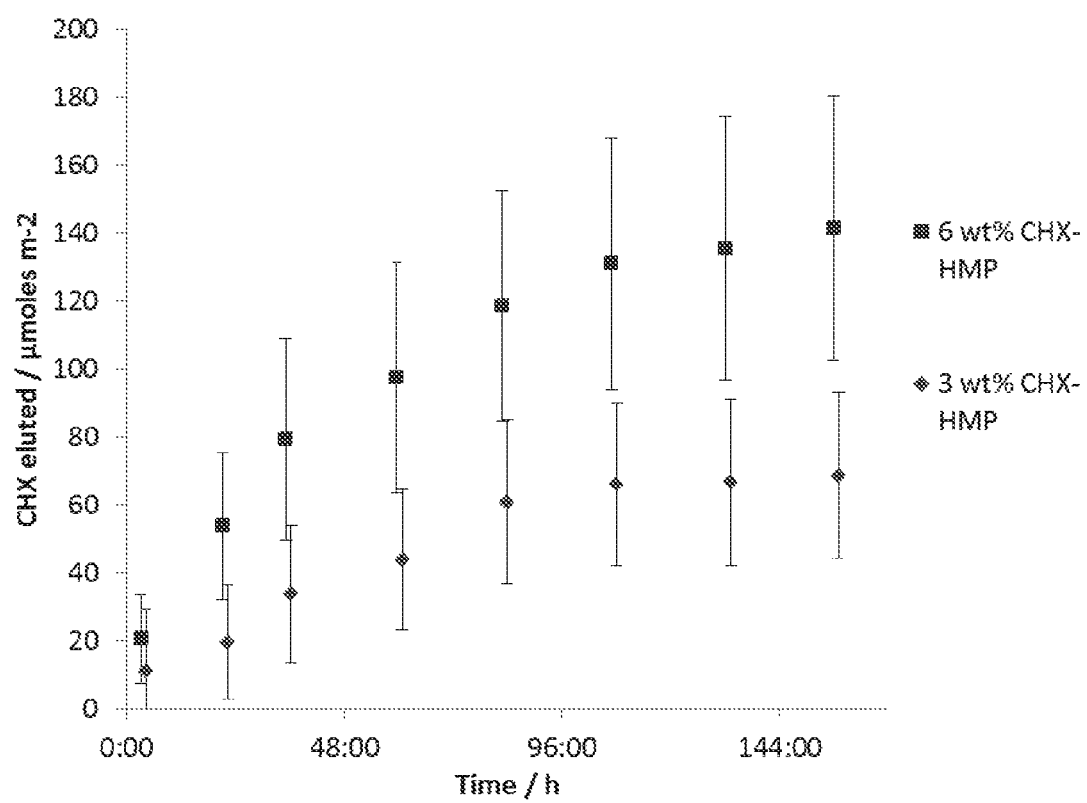
FIG. 27 shows CHX elution profiles from alginate films containing particular amounts of CHX-HMP-5 MNPs. Squares indicate 6 wt % MNPs; diamonds indicate 3 wt % MNPs.

Alginate by contrast did not disintegrate and released CHX over a period of 7 days (FIG. 27). CHX release continued over a period of 5-7 days and was dose dependent in that incorporating more MNPs released in a higher CHX release. This offers the possibility to control the release by selecting an appropriate dose of MNPs.

Example 30 and Comparative Example 14—Antimicrobial Efficacy of Wound Dressings The alginate MNP films of example 28 have been tested in antimicrobial assays. The test microorganisms are considered to be very relevant to wound infection: MRSA, Escherichia coli, Pseudomonas aeruginosa, Klebsiella pneumoniae and Acenitobacter baumanii. [Acenitobacter baumanii is the first microbe reported to have a resistance against CHX by means of an ion transport channel in the cell membrane. It is not a widespread pathogen but is found particularly in hospitals of the armed forces.]

The films were also tested against sections of a commercially available dressing containing silver nanoparticles (comparative example 14).

Table 12 shows zones of inhibition for experimental CHX-HMP MNP alginate composite dressings for 5 wound-associated pathogens compared with a commercial silver-based dressing, and indicate that for MRSA, E. coli, P. aeruginosa and K. pneumoniae the MNP dressings inhibit bacterial growth to a greater extent than the commercial dressing.

The silver dressing has a larger zone of inhibition than the MNP dressings for A. baumanii, but it is considered encouraging that the NP films inhibit growth of this microbe at all given that it has a recognised resistance to CHX.

TABLE 12

|  | MRSA | E. coli | P. aeruginosa | K. pneumoniae | A. baumanii |
|---|---|---|---|---|---|
| 0 wt % MNP | 0 | 0 | 0 | 0 | 0 |
| 3 wt % MNP | 21.0 | 18.4 | 13.5 | 15.6 | 13.0 |
|  | (0.9) | (1.5) | (0.4) | (0.7) | (0.7) |
| 6 wt % MNP | 22.6 | 19.9 | 14.2 | 16.5 | 14.9 |
|  | (1.9) | (1.6) | (0.4) | (0.6) | (1.0) |
| Ag dressing | 15.4 | 12.1 | 12.1 | 11.9 | 16.1 |
|  | (0.5) | (0.7) | (0.7) | (0.7) | (2.4) |

Example 31—Composite Materials: Glass Ionomer Cements

Glass ionomer cements containing the CHX-HMP MNPs have been produced. Two methods for sequestering the MNPs and rendering them suitable for inclusion in the GIC have been developed:
(i) a wet method whereby the MNPs are caused to sediment out of the colloid and centrifuging is used to allow the operator to decant the supernatant leaving a thick white paste, and
(ii) drying followed by ball-milling to yield a white powder. The products of both of these methods have been incorporated into a commercial GIC for measurement of various properties.

Figure 28:
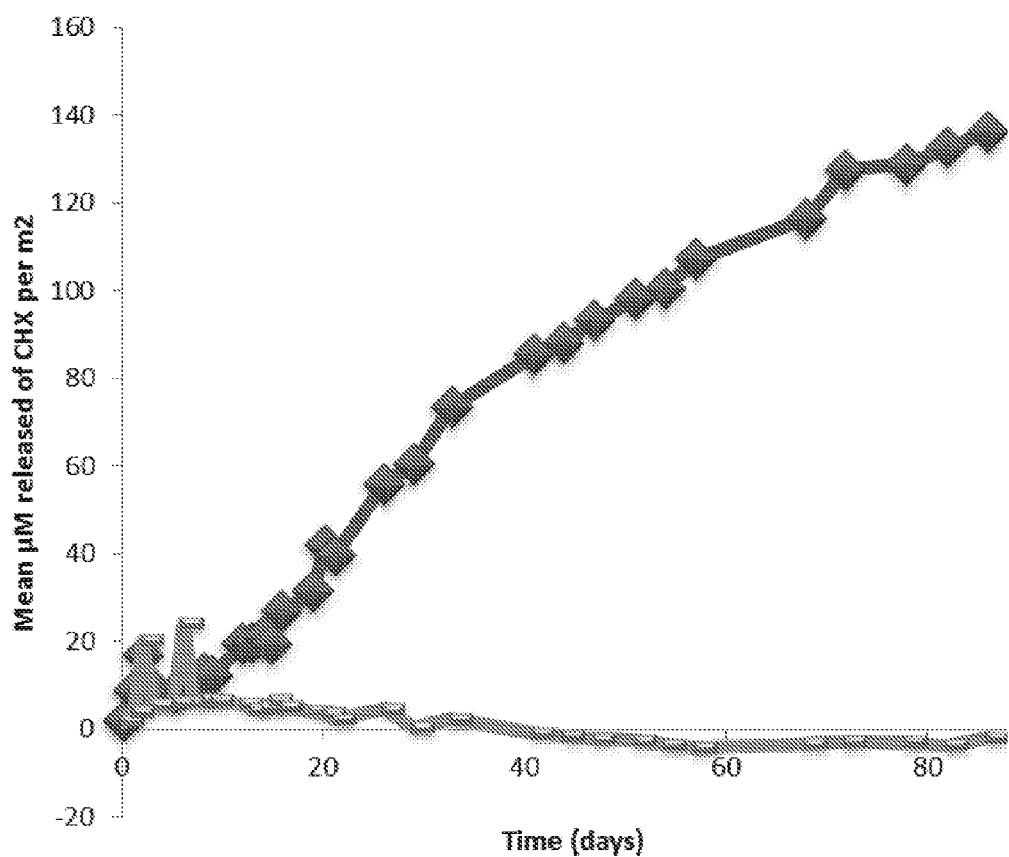
FIG. 28 shows CHX elution profiles for (diamonds) polyurethane coated with CHX-HMP-5 NPs at 1 dip coat, and (dashes) polyurethane treated with a 25 μM aqueous solution of CHX.

Example 32—Surface-Coated Materials: Polyurethane Catheters Polyurethane Substrates and Catheters Have Been Coated With CHX-HMP-5 MNPs It is desirable for this application to demonstrate long-term (>3 months) release of CHX. CHX release of at least 85 days has been demonstrated (FIG. 28).

Figure 29:
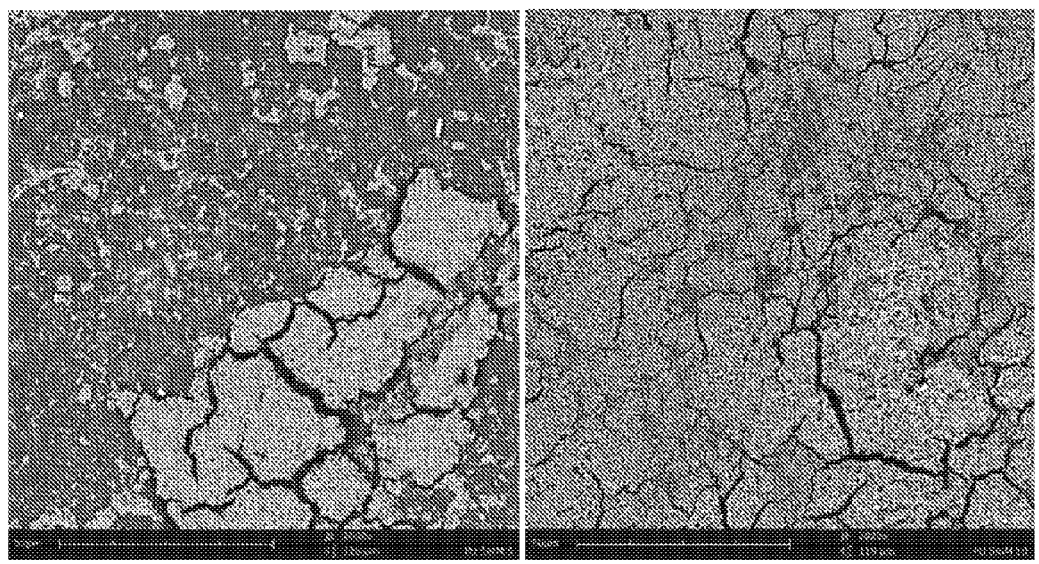
FIG. 29 shows SEM images showing polyurethane coated with CHX-HMP-5 NPs using (left) 5 repeats [50 μm, 2000×], and (right) 10 repeats [50 μm, 2020×] of the dip-coating method. Light areas show NP deposition.

Coating density has been investigated by changing the reagent concentration (50 mM of CHX and HMP) and the dip-coating regime (1, 5 and 10 dip repeats). It has been found that longer dip-times result in more release, and that 50 mM NP concentration in most cases releases more than a 5 mM concentration. More dips yield a greater coating density (FIG. 29). Initial data suggests that in some cases a lower release of CHX has been observed for more densely coated specimens, which may be explained, without wishing to be bound by theory, by noting that it is possible that heavier coated specimens may be less porous thus presenting less surface area of active material to the environment, or it may be related to the coating flaking off, although this has not been directly observed.

It appears that repeated dip coats and/or changing the time of dip coating allows control of MNP dose.

Examples 33-36 and Comparative Examples 15-22—Microbe Inhibition Efficacy for Polyurethane-Containing Specimens Extensive microbiology work has also been completed. Table 13 shows growth of microorganisms on polyurethane specimens with different surface treatments after 24 h incubation in bacteria growth medium. Key: −complete inhibition; +slight growth (growth observed at dilutions between $10^{-1}$-$10^{-3}$); ++ moderate growth (growth observed at dilutions between $10^{-4}$-$10^{-6}$); +++ high growth (growth at dilutions between $10^{-7}$-$10^{-12}$). The polyurethane specimens coated with CHX-HMP-50 exhibited no growth of MRSA, E. coli and P. aeruginosa and a reduction in growth of K. pneumoniae (examples 33-36) compared to controls treated with water (comparative examples 15-18) or an aqueous CHX solution (comparative examples 19-22).

TABLE 13

|  | MRSA | E. coli | P aeruginosa | K. pneumoniae |
|---|---|---|---|---|
| Control | ++ | ++ | +++ | +++ |
| CHX-HMP-50 coated PU | − | − | − | ++ |
| 80 µM CHX | ++ | ++ | ++ | ++ |

Example 37-44 and Comparative Examples 23-26—Live-Dead Staining

Live-dead staining has also been carried out using the microorganisms listed in examples 33-36 above. Polyurethane sections were first coated with NPs (CHX-HMP-5 and CHX-HMP-50) by dip-coating for 30 s and rinsing for 10 s, and then immersed in the relevant bacterial suspension for 24 h. SYTO 9 and propidium iodide live/dead stains were used for the staining.

Figure 30:
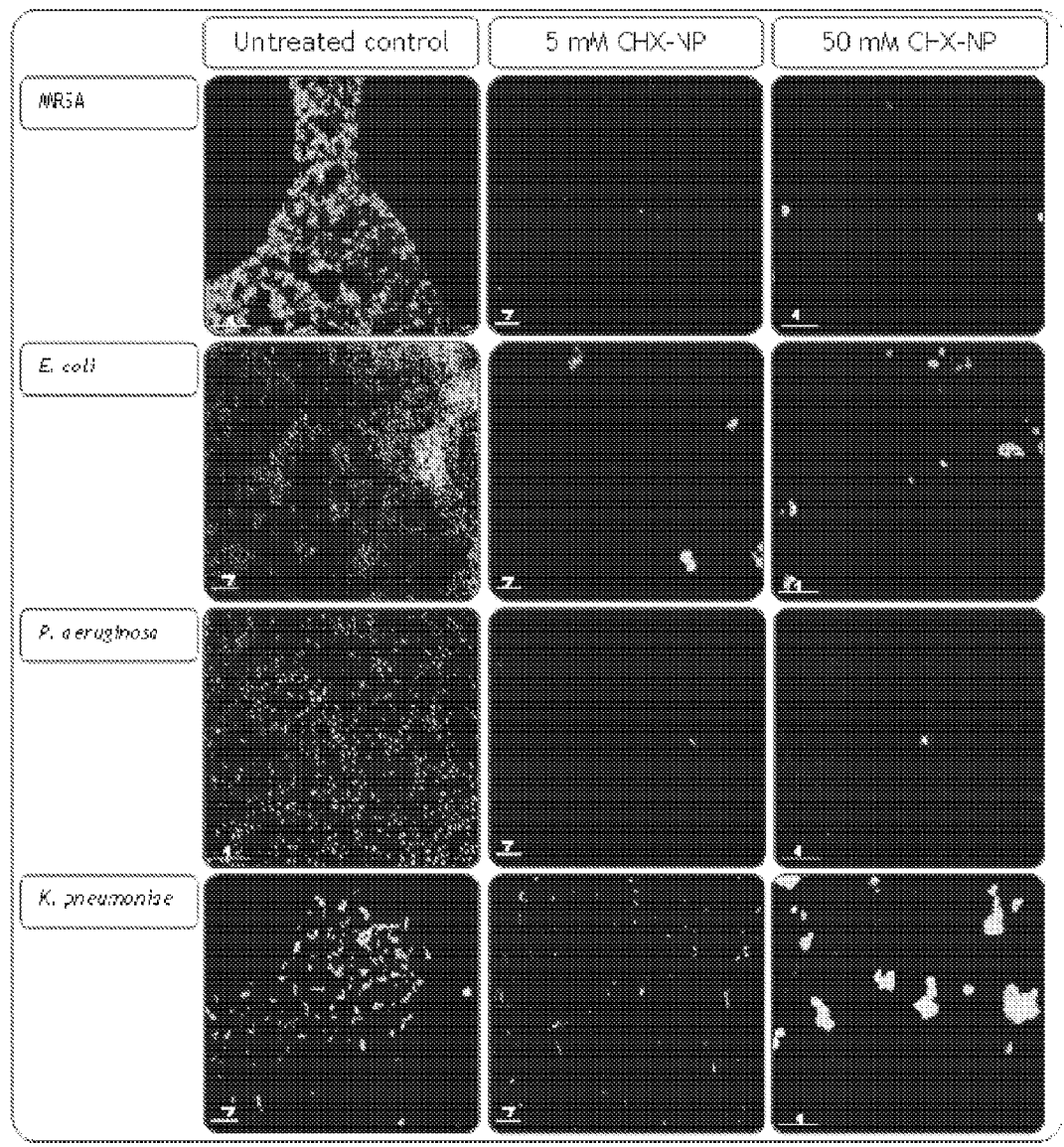
FIG. 30 shows live dead staining images of four microbes grown on polyurethane substrates: (from top to bottom) MRSA; E. coli; P. aeruginosa; and K. pneumonia treated with (from left to right) no MNPs (untreated); CHX-HMP-5 MNPs; and CHX-HMP-50 MNPs.

The lighter areas of FIG. 30 indicate areas of microbe growth. So, high levels of microbe growth are seen in the untreated control (comparative examples 23-26, leftmost column of FIG. 30). These images show the effect of the MNPs on microbial growth (middle and right columns of FIG. 30) and indicate that microbial growth is radically reduced by the presence of the MNPs at either concentration (examples 37-44). Note that the MNPs themselves take up some of the fluorescent dye, which can be seen as bright areas in the CHX-HMP-50 images (examples 41-44).

Examples 45-50 and Comparative Examples 27-32—Surface-Coated Materials: Medical Silicones Silicones are used as prostheses and other biomaterial devices throughout the body. The particular focus of this example is silicones used in the oral cavity, in the construction of palatal obturators (devices used to correct defects in the palate owing to surgery or developmental anomalies) and dentures.

These silicones become readily colonised by pathogenic microbes and yeasts, particularly *Candida albicans*. The adhesion of CHX-X MNPs to a medical silicone has been investigated. The microbial load on these devices is particularly high and for this reason, higher doses of CHX may be necessary. So, formulations other than CHX-HMP have been developed.

The CHX release from three formulations (CHX-HMP-5, CHX-TMP-5 and CHX-TP-5) has been investigated following dip-coating oral silicones for a range of times from 1 minute to 6 hours. Body (B) and sealant (S) represent two different kinds of silicone as supplied. The elution medium was refreshed at 8 weeks to account for any saturation.

Specifically, specimens of a 'body' and 'sealant' silicone used during denture soft lining and obturator construction (Mucopren Soft; Kettenbach, Eschenburg, Germany), were created using silicone molds measuring 5×8×2.5 mm. The molds were greased using petroleum jelly, the silicone was packed into the molds and allowed to cure at room temperature for 15 minutes. The specimens were then removed from the molds and ultrasonicated in 70% ethanol for 10 minutes, dried in air for 15 minutes and stored dry in sealed containers.

The CHX release from three formulations (CHX-HMP-5, CHX-TMP-5 and CHX-TP-5) was investigated following dip-coating of oral silicones for a range of times from 1 minute to 6 hours. Specimens were immersed in stirred NP suspensions (with the exception of TMP, which forms a viscous, sticky substance which cannot be stirred) for the allotted time, rinsed in deionised water for 10 s and dried in air. Further groups of n=10 specimens were immersed in 25 µM chlorhexidine digluconate solution (the residual concentration of chlorhexidine in aqueous solution following nanoparticle formation) for 6 hours to provide a positive control. This is denoted. CHX-C.

Figure 31:
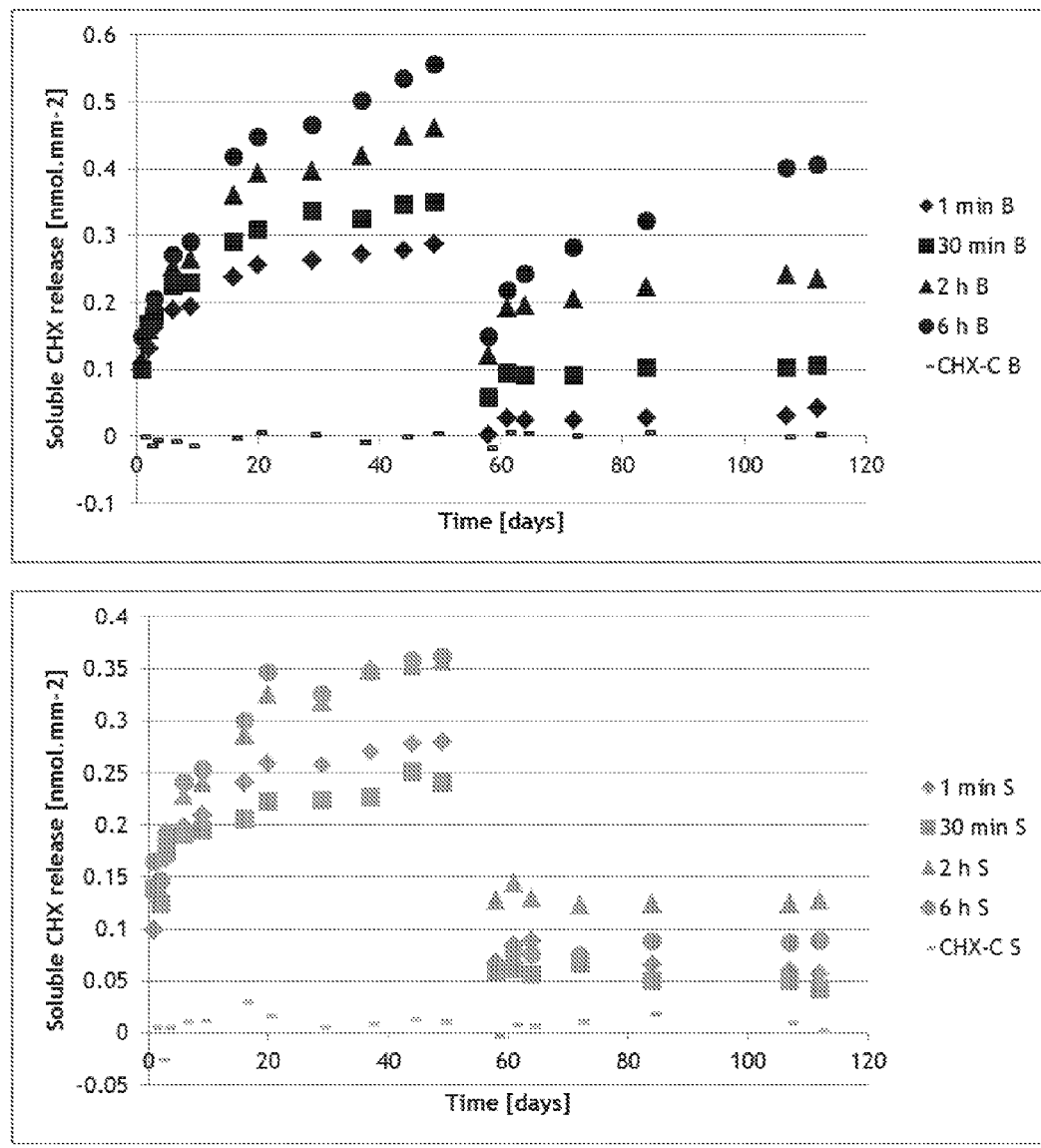
FIG. 31 shows CHX release from silicones coated with CHX-HMP-5 BPs with dip coating times of 1 min (diamonds), 30 mins (squares), 2 hours (triangles) or 6 hours (circles) and a control CHX solution (dashes) for (upper) a body (B) silicone and (lower) a sealant (S) silicone. The medium was refreshed at 8 weeks to account for any saturation.

As shown in FIG. 31, CHX-HMP MNP coated specimens exhibited a gradual release of CHX over the experimental period. The rate of release decreased with time, but when the artificial saliva was replaced the rate was increased again, suggesting that the degree of saturation of the artificial saliva with respect to the CHX salt was hindering release of CHX before the artificial saliva was refreshed. The release of CHX was sustained, in contrast to the other two salts, discussed below. Release of CHX from CHX-HMP coated specimens varied according to the coating time, with an increase in CHX being observed with longer coating time (but the relationship was not linear). More CHX release was observed from body silicone than sealant silicone.

Figure 32:
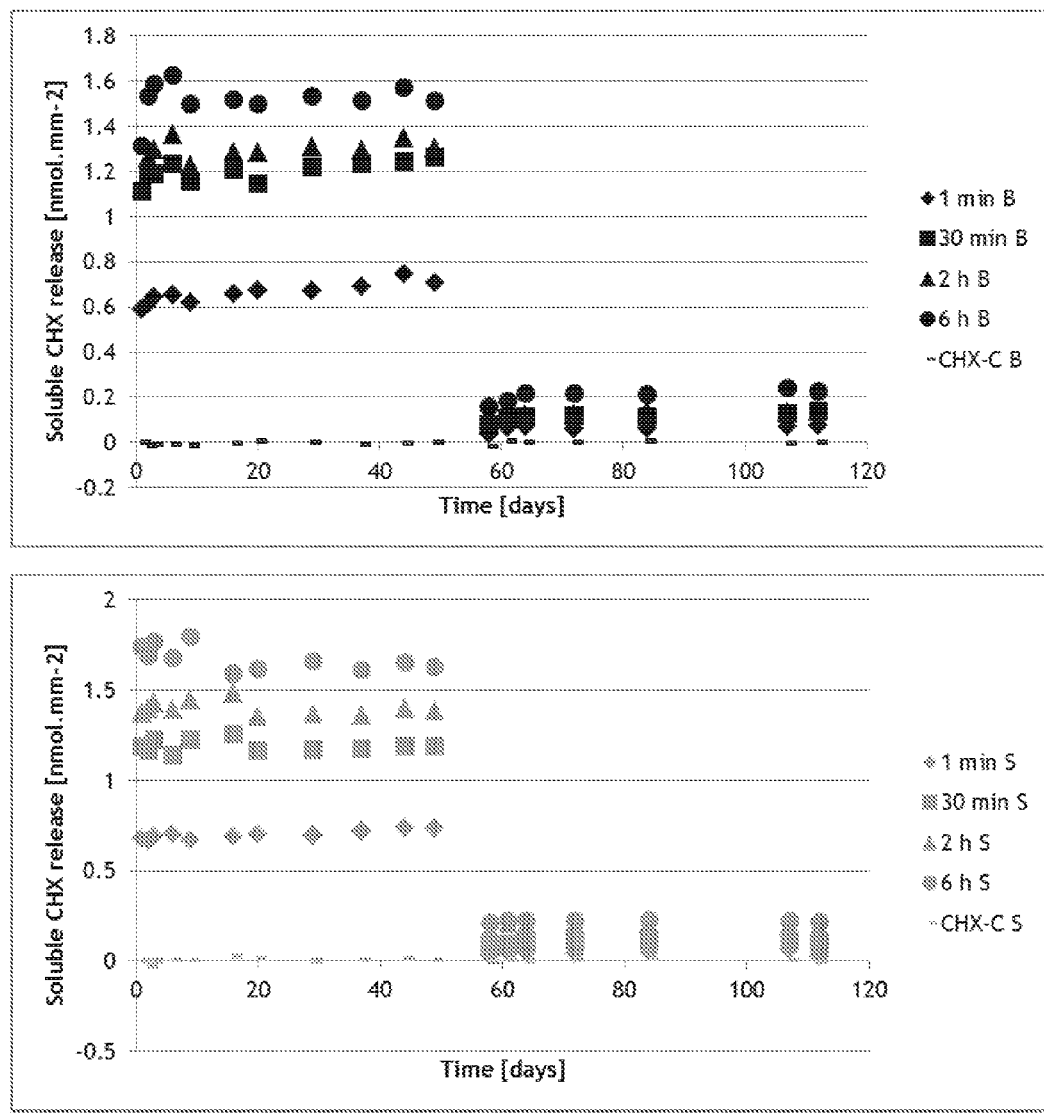
FIG. 32 shows CHX release from silicones coated with CHX-TP-5 NPs with dip coating times of 1 min (diamonds), 30 mins (squares), 2 hours (triangles) or 6 hours (circles) and a control CHX solution (dashes) for (upper) a body (B) silicone and (lower) a sealant (S) silicone. The medium was refreshed at 8 weeks to account for any saturation.

As shown in FIG. 32, CHX-TP MNP coated specimens exhibited quite a different CHX release profile from CHX-HMP MNP, with most or all of the CHX release observed in the first 24 h period. A small additional CHX release was observed following artificial saliva change, but again this small release reached completion within the first 24 h after the artificial saliva was introduced. Thus this formulation of the MNPs showed a higher release than CHX-HMP with approximately 3× the CHX release, but this release was short-lived. Release of CHX from CHX-TP coated specimens varied according to the coating time, with an increase in CHX with longer coating time (but again the relationship was not linear). The release of CHX was similar from body and sealant silicones.

Figure 33:
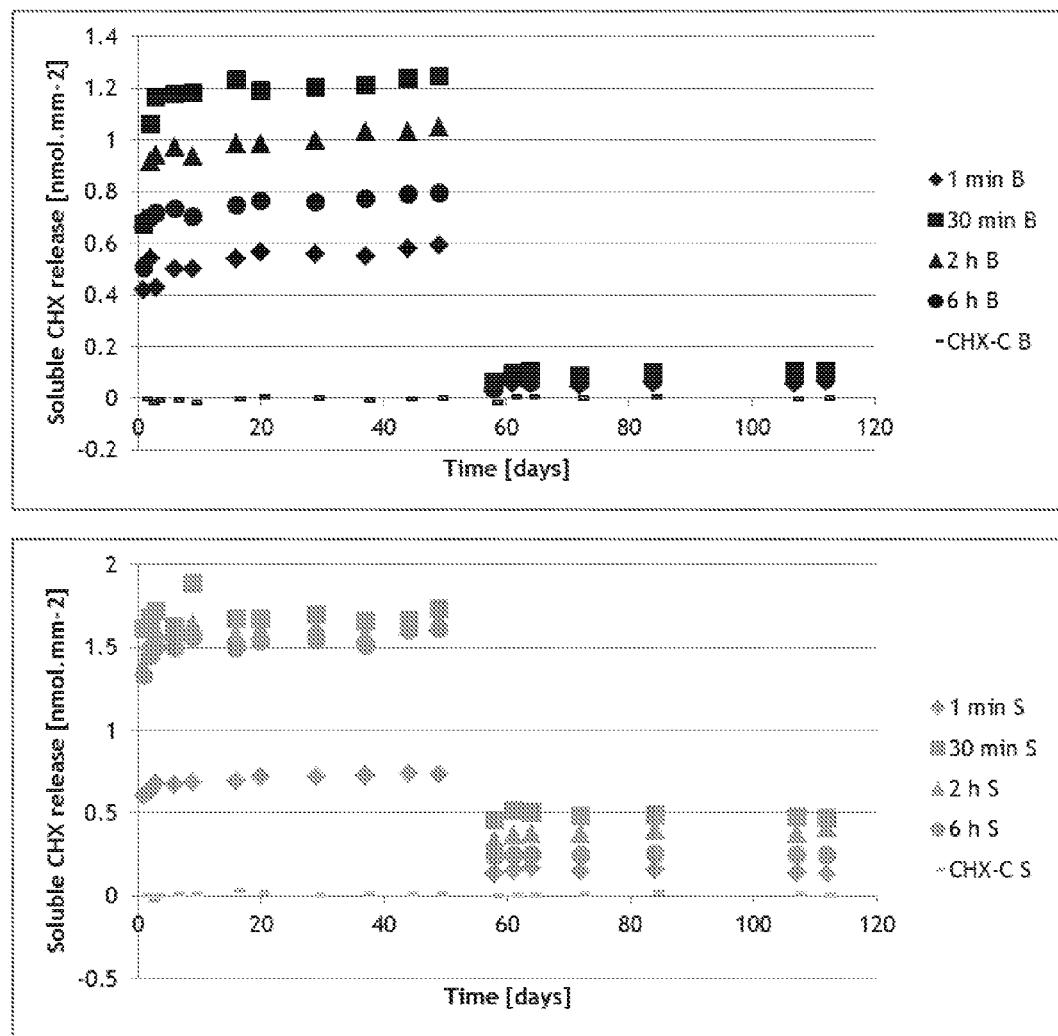
FIG. 33 shows CHX release from silicones coated with CHX-TMP-5 BPs with dip coating times of 1 min (diamonds), 30 mins (squares), 2 hours (triangles) or 6 hours (circles) and a control CHX solution (dashes) for (upper) a body (B) silicone and (lower) a sealant (S) silicone. The medium was refreshed at 8 weeks to account for any saturation.

As shown in FIG. 33, CHX-TMP MNP coated specimens, like those coated with CHX-TP MNP, exhibited most or all of their CHX release within the first 24 h of exposure to artificial saliva, both at the outset and after the artificial saliva was refreshed. Coating time effected CHX release but in a different manner from the other salts: the greatest. CHX release was observed for those specimens coated for 30 minutes, while 2 h and 6 h coated specimens showed intermediate CHX release and 1 min coated specimens had the smallest CHX release. More CHX release was observed from sealant silicone than body silicone.

It is notable that there appears to be scope to control the dose and duration of CHX release by selecting different anions (HMP, TMP, TP) and dip time. It was also noted that coating the silicones with MNPs did not significantly increase their water uptake; water uptake is detrimental to the performance of these silicones and has been observed as a side-effect of other attempts to confer upon them antimicrobial properties. This is a further advantage demonstrated by the MNPs of the invention.

The antifungal properties of the MNPs have been investigated. Initial experiments have consistently shown a dose-dependent inhibition of growth of *C. albicans* following seeding with the CHX-HMP MNPs, with a reduction in fungal growth seen at 1 h and no growth at 4 h.

Example 51 and Comparative Example 33—Surface-Coated Materials: Titanium Implants CHX-HMP MNPs have been used to coat titanium to develop antimicrobial coatings for implants.

Figure 34:
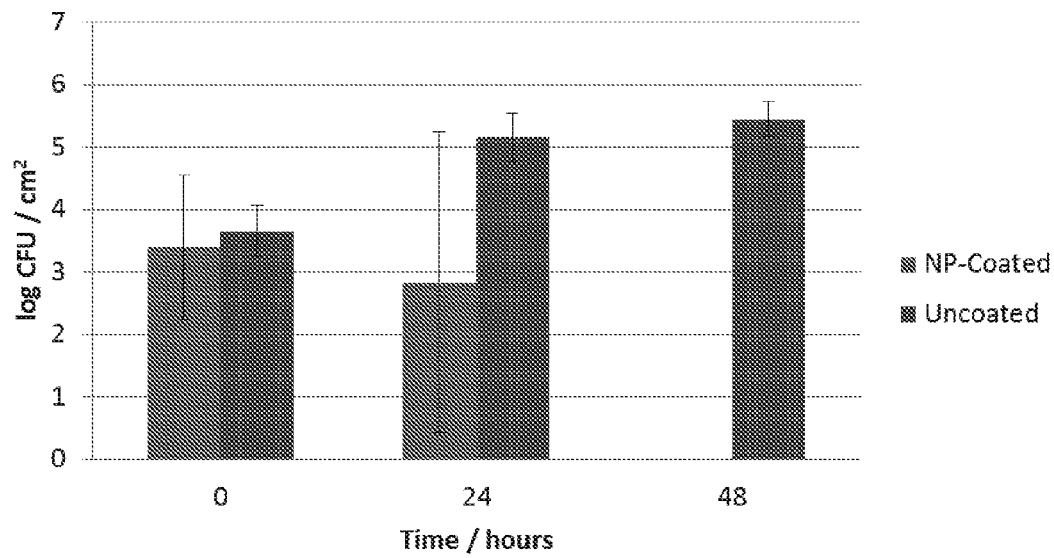
FIG. 34 shows growth of S. gordonii on a titanium surface with a coating of CHX-HMP-5 NPs (left-hand, light grey bar) and without a coating of CHX-HMP NPs (right-hand, dark grey bar).

The CHX-HMP-5 MNP-coated titanium substrates (prepared by immersion in CHX-HMP-5 suspension for 30 s, rinsed in deionised water for 10 s, then dried) have been shown to inhibit growth of *Streptococcus gordonii* and *Porphyromonas qingivalis*. Furthermore, when the titanium substrates are coated with a salivary pellicle, a proteinaceous film that coats any material placed in the mouth, the antimicrobial effect is not hampered. Representative data of colony-forming units of *S. gordonii* on titanium surfaces with (example 51) and without (comparative example 33) CHX-HMP MNPs are shown in FIG. 34.

Examples 52-54 and Comparative Examples 34-36—Oral Care Products and Topical Treatments CHX in aqueous solution is in already in use in dentistry. It is available in supermarkets and pharmacies as a 2.2 mM oral rinse suitable for controlling plaque and periodontal disease/gum irritation. It is also used as a topical antimicrobial agent in many applications such as more advanced periodontal disease, during oral surgery, during endodontic treatment.

This example shows that delivering CHX as CHX-HMP MNPs, rather than in aqueous solution, changes the release of CHX.

Figure 35:
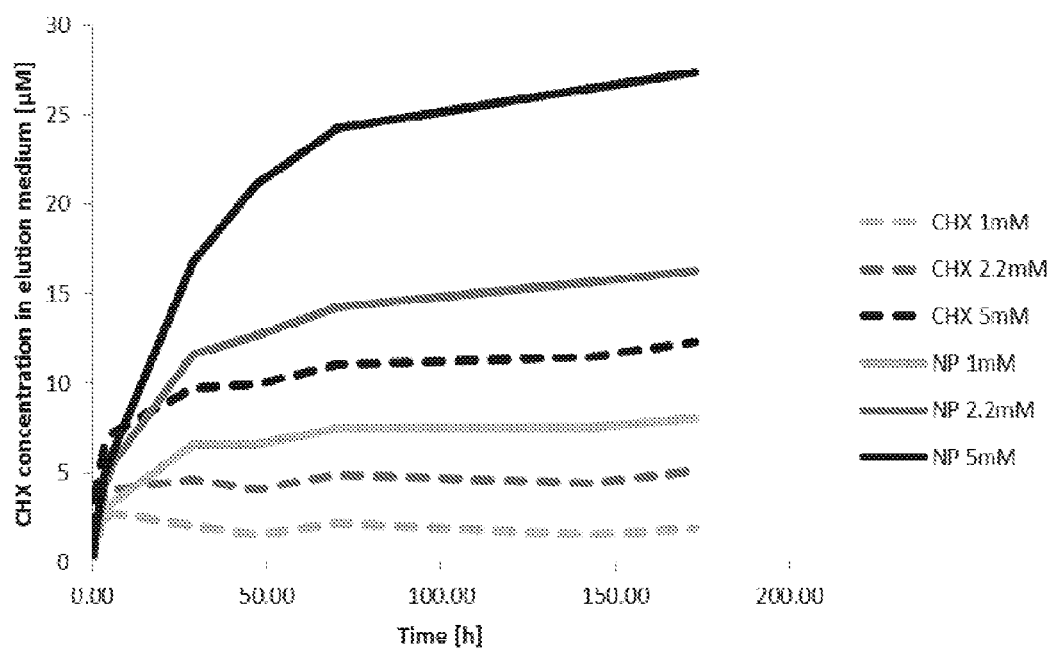
FIG. 35 shows CHX release from hydroxyapatite discs treated with solutions of aqueous CHX or suspensions of CHX-HMP MNPs of equivalent concentration into deionised water. Aqueous CHX data are shown as dashed lines, while NP suspension data are shown as solid lines. Concentrations of 5 mM are shown in black; 2.2 mM: concentrations are shown in mid-grey; and concentrations of 1 mM are shown in light grey. From lower to upper: aqueous CHX 1 mM; aqueous CHX 2.2 mM; NP suspension 1 mM; aqueous CHX 5 mM; NP suspension 2.2 mM; NP suspension 5 mM.

Hydroxyapatite discs (n=6 per group) were used as a substitute for tooth tissue. Three aqueous solutions of CHX digluconate were prepared, 1, 2.2 and 5 mM (comparative examples 34-36, respectively). Three CHX-HMP MNP suspensions were prepared with matched total concentrations, so with 1, 2.2, 5 mM of CHX and HMP (examples 52-54, respectively). Hydroxyapatite discs were immersed in the preparation for 15 s, rinsed, and the CHX release observed as a function of time (FIG. 35).

A more prolonged, and overall larger, release of CHX was observed from discs treated with MNP suspensions than aqueous solutions. The CHX-HMP MNP treated discs displayed a more prolonged, and greater, release of CHX, indicating that more CHX was retained when in MNP form than when delivered in solution. This has potential in the development of over-the-counter oral care products and/or topical agents for professional use to confer a much longer lasting antimicrobial oral environment.

Example 55 and Comparative Example 37—Antimicrobial Paints

Methods of sequestering the MNPs as a suitable paste for use in antimicrobial paints have been carried out and prototypes have been created with 25% by mass MNP paste in an emulsion paint, and compared with a market leading antimicrobial paint (Dulux Sterishield).

The NP paste was created by preparing 400 mL CHX-HMP-5 by mixing 200 mL 10 mM CHX digluconate with 200 mL 10 mM sodium HMP at room temperature and pressure during vigorous mixing. Approximately 50 mL 1M KCl was added, and then the stirring was ceased. The resulting mixture was allowed to sediment and the top ~300 mL clear supernatant discarded. The remaining liquid was centrifuged for 20 minute at 5000 rpm in a benchtop centrifuge, which resulted in separation of supernatant and a viscous white paste with a consistency between paint and toothpaste. The supernatant was again discarded and the paste removed from the tubes and used.

Figure 36:
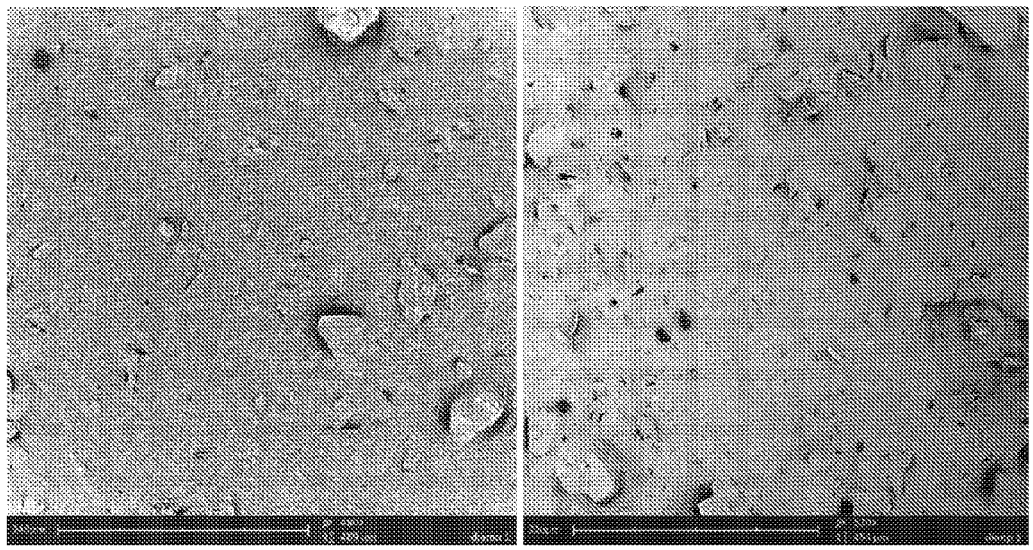
FIG. 36 shows SEM images of the surface of (left) diamond matt emulsion paint. [240 μm, 490×] and (right) diamond matt emulsion paint [220 μm, 530×] containing 25% by mass CHX-HMP-5 NP paste.

The experimental paint was viable (example 55, FIG. 36, right image), drying apparently normally by eye) an with a similar surface finish to the unmodified paint (comparative example 37, FIG. 36 left image).

Examples 56-57 and Comparative Examples 38-41—Microbe Inhibition Efficacy in Antimicrobial Paints Growth of MRSA and *E. coli* were investigated on the negative control (unmodified emulsion, comparative examples 38-39), experimental (NP doped) and positive control (Sterishield, comparative examples 40-41) paints after 24 h incubation in the bacterial cultures. Glass coverslips were coated on both sides with a single coat of the paints and allowed to dry.

Figure 37:
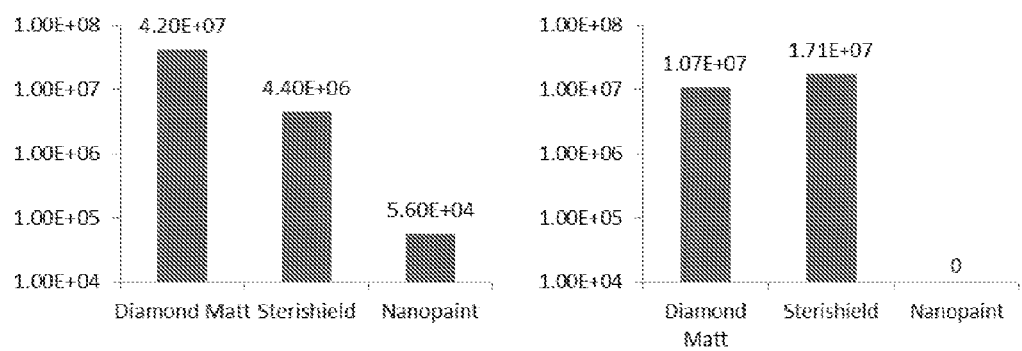
FIG. 37 shows growth of (left) MRSA, and (right) E. coli on Diamond Matt paint (negative control, left-hand bars), Sterishield paint (positive control, middle bars), and "Nanopaint" (paint containing CHX-HMP MNPs, right-hand bars) after 24 h incubation. The y axis units are in colony forming units (cfu).

For MRSA, Sterishield effected a 10-fold reduction in growth of MRSA, but the MNP paint effected a 1000-fold reduction in the same (FIG. 37).

For *E. coli*, Sterishield had no effect on bacterial growth whereas the MNP paint eliminated *E. coli* growth with no recoverable bacteria (FIG. 37).

The invention claimed is:

1. An antimicrobial micro- or nanoparticle comprising a chlorhexidine salt, wherein the anion in the salt is selected from:
    phosphates chosen from the homologous series of cyclic metaphosphates which begins with trimetaphosphate, and the homologous series of polyphosphates which begins with pyrophosphate.

2. An antimicrobial micro- or nanoparticle of claim 1, wherein the anion in the salt is either:
    selected from pyrophosphate, triphosphate, hexametaphosphate; or
    selected from the homologous series of cyclic metaphosphates.

3. An antimicrobial micro- or nanoparticle according to claim 1, wherein the salt is chlorhexidine hexametaphosphate.

4. An antimicrobial micro- or nanoparticle according to claim 1, wherein at least one dimension of the micro- or nanoparticle is from 20 to 200 nm.

5. A colloidal suspension comprising the antimicrobial micro- or nanoparticle of claim 1.

6. A colloidal suspension of claim 5, wherein the colloids are dispersed in water or an aqueous solution.

7. A colloidal suspension of claim 5, wherein the absolute value of the zeta ($\zeta$) potential is at least 20 mV.

8. A medical article comprising an antimicrobial micro- or nanoparticle of claim 1.

9. A medical article of claim 8, wherein the article is a venous catheter, urinary catheter, dental implant, mouthguard, dentures, wound dressings or medical packaging.

10. A composite material comprising antimicrobial micro- or nanoparticle of claim 1.

11. A composite material of claim 10 which is a dental cement, a paint or an oral care composition.

12. A composite material of claim 10 which comprises antimicrobial micro- or nanoparticles in an amount of from 1 wt % to 60 wt % of the overall composite.

13. A composite material of claim 10 which is a glass ionomer cement (GIC).

14. A method of making an antimicrobial micro- or nanoparticle comprising
    reacting an aqueous solution comprising chlorhexidine cations with an anion selected from:
    phosphates chosen from the homologous series of cyclic metaphosphates which begins with trimetaphosphate, and the homologous series of polyphosphates which begins with pyrophosphate; and
    in a ratio of from 1:100 to 100:1 to produce a colloidal suspension of micro- or nanoparticles.

* * * * *